(12) United States Patent
Goetschi et al.

(10) Patent No.: US 7,378,417 B2
(45) Date of Patent: May 27, 2008

(54) PYRAZOLO-PYRIMIDINE DERIVATIVES

(75) Inventors: Erwin Goetschi, Reinach (CH); Juergen Wichmann, Steinen (DE); Thomas Johannes Woltering, Weil am Rhein (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 400 days.

(21) Appl. No.: 11/156,974

(22) Filed: Jun. 20, 2005

(65) Prior Publication Data

US 2005/0282827 A1 Dec. 22, 2005

(30) Foreign Application Priority Data

Jun. 21, 2004 (EP) ................... 04102837

(51) Int. Cl.
*A61K 31/5355* (2006.01)
*A61K 31/496* (2006.01)
*A61K 31/519* (2006.01)
*C07D 413/10* (2006.01)
*C07D 487/04* (2006.01)

(52) U.S. Cl. ............... 514/234.2; 514/252.16; 544/281; 544/117

(58) Field of Classification Search ........ 544/281, 544/117; 514/259.31, 234.2
See application file for complete search history.

(56) References Cited

U.S. PATENT DOCUMENTS 5,017,212 A * 5/1991 Ishida et al. ............ 504/213

FOREIGN PATENT DOCUMENTS

EP 0891978 1/1999
WO WO2005/040171 5/2005

OTHER PUBLICATIONS

D'Onofrio, et al., J. Neurochem. (Mar. 2003) vol. 84(6) pp. 1288-1295.

* cited by examiner

*Primary Examiner*—Brenda L. Coleman
*Assistant Examiner*—Susanna Moore
(74) *Attorney, Agent, or Firm*—George W. Johnston; Patricia S. Rocha-Tramaloni; Kimberly J. Prior

(57) ABSTRACT

The invention relates to compounds of formula (I)

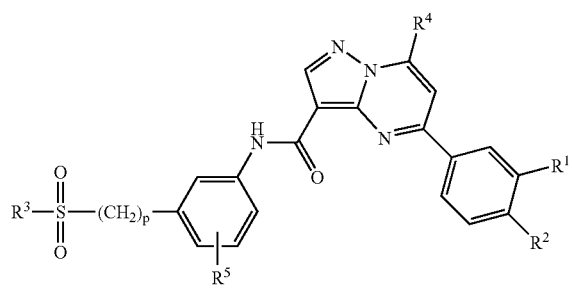

wherein $R^1$, $R^2$, $R^3$, $R^4$, $R^5$ and p are as defined in the description and to pharmaceutically acceptable salts thereof, to pharmaceutical compositions containing such compounds, to the manufacture of such compounds and compositions, and to methods of treating or preventing acute and/or chronic central nervous system disorders by administering such compounds.

26 Claims, No Drawings

PYRAZOLO-PYRIMIDINE DERIVATIVES

BACKGROUND OF THE INVENTION

In the central nervous system (CNS) the transmission of stimuli takes place by the interaction of a neurotransmitter, which is sent out by a neuron, with a neuroreceptor.

L-glutamic acid, the most commonly occurring neurotransmitter in the CNS, plays a critical role in a large number of physiological processes. The glutamate-dependent stimulus receptors are divided into two main groups. The first main group forms ligand-controlled ion channels. The metabotropic glutamate receptors (mGluR) form the second main group and, furthermore, belong to the family of G-protein-coupled receptors.

At present, eight different members of these mGluR are known and of these some even have sub-types. On the basis of structural parameters, the different influences on the synthesis of secondary metabolites and the different affinity to low-molecular weight chemical compounds, these eight receptors can be sub-divided into three sub-groups: mGluR1 and mGluR5 belong to group I, mGluR2 and mGluR3 belong to group II and mGluR4, mGluR6, mGluR7 and mGluR8 belong to group III.

Ligands of metabotropic glutamate receptors belonging to the group II can be used for the treatment or prevention of acute and/or chronic neurological disorders such as psychosis, schizophrenia, Alzheimer's disease, cognitive disorders and memory deficits.

Other treatable indications in this connection are restricted brain function caused by bypass operations or transplants, poor blood supply to the brain, spinal cord injuries, head injuries, hypoxia caused by pregnancy, cardiac arrest and hypoglycaemia. Further treatable indications are chronic and acute pain, Huntington's chorea, amyotrophic lateral sclerosis (ALS), dementia caused by AIDS, eye injuries, retinopathy, idiopathic parkinsonism or parkinsonism caused by medicaments as well as conditions which lead to glutamate-deficiency functions, such as e.g. muscle spasms, convulsions, migraine, urinary incontinence, nicotine addiction, opiate addiction, anxiety, vomiting, dyskinesia depressions and glioma since mGluR2 antagonists have been found to reduce cell proliferation in human glioma cells (J. Neurochem. March 2003, 84(6): 1288-95).

SUMMARY OF THE INVENTION

The present invention provides pyrrazolo-pyrimidine derivatives, a process for the manufacture thereof, pharmaceutical compositions containing such derivatives, and their use for treating or preventing metabotropic glutamate receptor mediated disorders.

In particular, the present invention provides pyrrazolo-pyrimidine derivatives of formula I

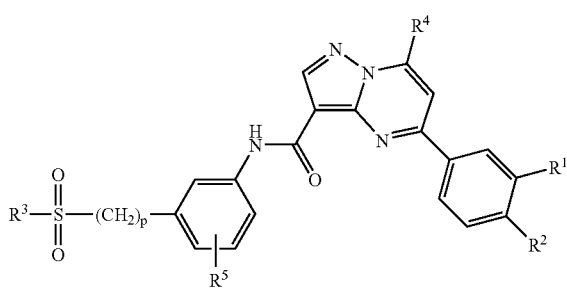

(I)

wherein
p is 0 or 1;
$R^1$ and $R^2$ are each independently H; halogen; lower alkyl optionally substituted by lower alkoxy; lower alkoxy optionally substituted by one or more halogen; or $CF_3$;
$R^3$ is lower alkyl; hydroxy-lower alkyl; or $NR^aR^b$;
$R^a$ and $R^b$ are independently selected from the group consisting of:
H;
lower alkyl optionally substituted by one or more hydroxy, fluoro, cycloalkyl aryl, heteroaryl or $NR^cR^d$,
wherein $R^c$ and $R^d$ are independently selected from H or lower alkyl;
cycloalkyl;
aryl; and
heteroaryl;

or $R^a$ and $R^b$ together with the nitrogen atom to which they are attached form an optionally substituted 5 or 6 membered heterocyclic ring;
$R^4$ is H, Cl, lower alkoxy, cycloalkyl or straight lower alkyl which is optionally substituted by one or more F; and
$R^5$ is H; halogen or lower alkyl;

or a pharmaceutically acceptable salt thereof;

with the exception of the compounds:
pyrazolo[1,5-a]pyrimidine-3-carboxamide, 7-(difluoromethyl)-5-(4-methylphenyl)-N-[3-(4-morpholinylsulfonyl)phenyl];
pyrazolo[1,5-a]pyrimidine-3-carboxamide, 7-(difluoromethyl)-N-[3-(4-morphonlinylsulfonyl)phenyl]-5-phenyl]; and
pyrazolo[1,5-a]pyrimidine-3-carboxamide, 7-(difluoromethyl)-5-(4-methoxyphenyl)-N-[3-(4-morpholinylsulphonyl)phenyl].

The three compounds disclaimed from the scope for formula I are known from chemical libraries. These three compounds were never disclosed in relation with metabotropic glutamate receptors.

The compounds of formula I can also be used in form of their prodrugs. Examples are esters, N-oxides, phosphate esters, glycoamide esters, glyceride conjugates and the like. The prodrugs may add to the value of the present compounds advantages in absorption, pharmacokinetics in distribution and transport to the brain.

It has surprisingly been found that the compounds of general formula I are metabotropic glutamate receptor antagonists. Compounds of formula I are distinguished by valuable therapeutic properties.

The invention also relates to the use of the compounds of the invention, including the compounds:
pyrazolo[1,5-a]pyrimidine-3-carboxamide, 7-(difluoromethyl)-5-(4-methylphenyl)-N-[3-(4-morpholinylsulfonyl)phenyl];
pyrazolo[1,5-a]pyrimidine-3-carboxamide, 7-(difluoromethyl)-N-[3-(4-morphonlinylsulfonyl)phenyl]-5-phenyl]; and
pyrazolo[1,5-a]pyrimidine-3-carboxamide, 7-(difluoromethyl)-5-(4-methoxyphenyl)-N-[3-(4-morpholinylsulphonyl)phenyl];

and pharmaceutically acceptable salts thereof; for the treatment or prevention of a disease of the aforementioned kind.

The present invention also provides pharmaceutical compositions containing compounds of the invention or pharmaceutically acceptable salts thereof and methods for the manufacture of such compounds and compositions.

DETAILED DESCRIPTION OF THE INVENTION

Unless otherwise stated, the following terms used in the present description have the definitions given below.

The term "lower alkyl" denotes straight-chain or branched saturated hydrocarbon residues with 1 to 7 carbon atoms, preferably with 1 to 4 carbon atoms, such as methyl, ethyl, n-propyl, i-propyl, i-butyl, t-butyl, and the like.

The term "hydroxy-lower alkyl" denotes a lower alkyl residue in the sense of the foregoing definition comprising one, two, three or four hydroxy groups, preferably one. Examples of "hydroxy-lower alkyl" residues include methanol, ethanol, 1-propanol, 2-propanol, 3-propanol, i-butanol and the like.

The term "lower alkenyl" denotes straight-chain or branched unsaturated hydrocarbon residues with 2 to 7 carbon atoms, preferably with 2 to 4 carbon atoms, such as ethenyl or propenyl.

The term "lower alkoxy" denotes a lower alkyl residue in the sense of the foregoing definition bound via an oxygen atom. Examples of "lower alkoxy" residues include methoxy, ethoxy, isopropoxy and the like. Examples of lower alkoxy substituted by one or more halogen include 2,2,2-trifluoroethoxy groups.

The term "aryl" represents an aromatic carbocyclic group consisting of one individual ring, or one or more fused rings in which at least one ring is aromatic in nature. Preferred aryl group is phenyl.

The term "heteroaryl" refers to an aromatic 5- or 6-membered ring containing one or more heteroatoms selected from nitrogen, oxygen or sulphur. Preferred are those heteroaryl groups selected from nitrogen. Examples of such heteroaryl groups are pyridinyl, pyrazinyl, pyrimidinyl or pyridazinyl.

The term "halogen" embraces fluorine, chlorine, bromine and iodine.

The term "cycloalkyl" means a cycloalkyl group containing 3 to 12, preferably 3 to 6 carbon atoms, such as cyclopropyl, cyclobutyl, cyclopentyl or cyclohexyl.

The term "5 or 6 membered heterocyclic ring" denotes a heterocyclic ring having 5 or 6 ring members comprising at least one carbon atom as ring member and optionally 1, 2 or 3 additional heteroatom(s) ring members selected from N, O or S, the remaining ring members being carbon atoms. Examples of 5 or 6 heterocyclic ring include but are not limited to 1H-tetrazole; 2H-tetrazole; 1,2,3- and 1,24-triazole; imidazole; pyrrole; 1,2,3-, 1,3,4- or 1,2,5-thiadiazine; 1,4-oxazine; 1,2- or 1,4-thiazine; 4-morpholinyl; 1-pyrrolidinyl; 1-piperazinyl, preferably 4-morpholinyl; 1-pyrrolidinyl or 1-piperazinyl. Substituents for such 5 or 6 membered heterocyclic ring include but are not limited to halo, amino, nitro, cyano, hydroxy, hydroxy-lower alkyl, lower alkoxy, lower alkenyl, cycloalkyl, lower alkyl; or $CF_3$, and preferably lower alkyl; or $CF_3$.

The term "pharmaceutically acceptable," such as pharmaceutically acceptable carrier, excipient, etc., means pharmacologically acceptable and substantially non-toxic to the subject to which the particular compound is administered.

The terms "pharmaceutically acceptable salt" or "pharmaceutically acceptable addition salt" refer to any salt derived from an inorganic or organic acid or base.

The term "therapeutically effective amount" means an amount that is effective to prevent, alleviate or ameliorate symptoms of disease or prolong the survival of the subject being treated.

The present invention provides pyrrazolo-pyrimidine derivatives of the general formula I

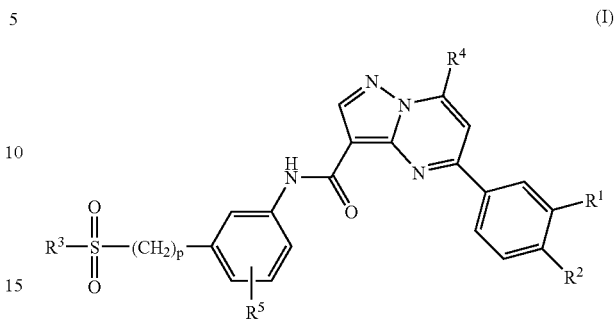

(I)

wherein
p is 0 or 1;
$R^1$ and $R^2$ are each independently H; halogen; lower alkyl optionally substituted by lower alkoxy; lower alkoxy optionally substituted by one or more halogen; or $CF_3$;
$R^3$ is lower alkyl; hydroxy-lower alkyl; or $NR^aR^b$;
$R^a$ and $R^b$ are independently selected from the group consisting of:
H;
lower alkyl optionally substituted by one or more hydroxy, fluoro, cycloalkyl aryl, heteroaryl or $NR^cR^d$, wherein $R^c$ and $R^d$ are independently selected from H or lower alkyl;
cycloalkyl;
aryl; and
heteroaryl;
or $R^a$ and $R^b$ together with the nitrogen atom to which they are attached form an optionally substituted 5 or 6 membered heterocyclic ring;
$R^4$ is H, Cl, lower alkoxy, cycloalkyl or straight lower alkyl which is optionally substituted by one or more F; and
$R^5$ is H; halogen or lower alkyl;

or a pharmaceutically acceptable salt thereof;
with the exception of the compounds:
pyrazolo[1,5-a]pyrimidine-3-carboxamide, 7-(difluoromethyl)-5-(4-methylphenyl)-N-[3-(4-morpholinylsulfonyl)phenyl];
pyrazolo[1,5-a]pyrimidine-3-carboxamide, 7-(difluoromethyl)-N-[3-(4-morphonlinylsulfonyl)phenyl]-5-phenyl]; and
pyrazolo[1,5-a]pyrimidine-3-carboxamide, 7-(difluoromethyl)-5-(4-methoxyphenyl)-N-[3-(4-morpholinylsulphonyl)phenyl].

The compounds of formula I can also be used in form of their prodrugs. Examples are esters, N-oxides, phosphate esters, glycoamide esters, glyceride conjugates and the like. The prodrugs may add to the value of the present compounds through advantages in absorption, pharmacokinetics in distribution and transport to the brain.

Preferred compounds of the invention are those compounds wherein:
p is 0 or 1;
$R^1$ and $R^2$ are each independently selected from the group consisting of H; halogen; lower alkyl optionally substituted by lower alkoxy; lower alkoxy optionally substituted by one or more halogen; and $CF_3$;

R³ is selected from the group consisting of lower alkyl; hydroxy-lower alkyl; and NR$^a$R$^b$, wherein R$^a$ and R$^b$ are independently selected from the group consisting of:

H;

lower alkyl optionally substituted by one or more hydroxy, fluoro, cycloalkyl, aryl, heteroaryl or NR$^c$R$^d$ wherein R$^c$ and R$^d$ are independently selected from H or lower alkyl;

cycloalkyl;

aryl; and heteroaryl;

or R$^a$ and R$^b$ together with the nitrogen atom to which they are attached form a 4-morpholinyl; 1-pyrrolidinyl or 1-piperazinyl group;

R⁴ is H, cyclopropyl or straight lower alkyl which is optionally substituted by one or more F; and R⁵ is H; halogen or lower alkyl.

Other preferred compounds of the invention are those wherein R¹ and R² are each independently selected from the group consisting of H, Cl, Me, CF₃, MeO, EtO and CF₃CH₂O— and R³, R⁴, R⁵ and p are as defined above.

Other preferred compounds of the invention are those compounds wherein R³ is lower alkyl; and R¹, R², R⁴, R⁵ and p are as defined hereinabove, for example the following compounds:

7-Difluoromethyl-5-(4-trifluoromethyl-phenyl)-pyrazolo[1,5-a]pyrimidine-3-carboxylic acid(3-methanesulfonyl-phenyl)-amide;

7-Trifluoromethyl-5-(4-trifluoromethyl-phenyl)-pyrazolo[1,5-a]pyrimidine-3-carboxylic acid(3-methanesulfonyl-phenyl)-amide;

5-(4-Chloro-phenyl)-7-trifluoromethyl-pyrazolo[1,5-a]pyrimidine-3-carboxylic acid(3-methanesulfonyl-phenyl)-amide;

5-(3,4-Dichloro-phenyl)-7-difluoromethyl-pyrazolo[1,5-a]pyrimidine-3-carboxylic acid(3-methanesulfonyl-phenyl)-amide;

5-(3,4-Dichloro-phenyl)-7-trifluoromethyl-pyrazolo[1,5-a]pyrimidine-3-carboxylic acid(3-methanesulfonyl-phenyl)-amide;

7-Difluoromethyl-5-(3-methyl-4-trifluoromethyl-phenyl)-pyrazolo[1,5-a]pyrimidine-3-carboxylic acid(3-methanesulfonyl-phenyl)-amide;

5-(3-Methyl-4-trifluoromethyl-phenyl)-7-trifluoromethyl-pyrazolo[1,5-a]pyrimidine-3-carboxylic acid(3-methanesulfonyl-phenyl)-amide;

5-(3-Ethoxy-4-trifluoromethyl-phenyl)-7-trifluoromethyl-pyrazolo[1,5-a]pyrimidine-3-carboxylic acid(3-methanesulfonyl-phenyl)-amide;

7-Difluoromethyl-5-(3-ethoxy-4-trifluoromethyl-phenyl)-pyrazolo[1,5-a]pyrimidine-3-carboxylic acid(3-methanesulfonyl-phenyl)-amide;

5-[3-(2,2,2-Trifluoro-ethoxy)-4-trifluoromethyl-phenyl]-7-trifluoromethyl-pyrazolo[1,5-a]pyrimidine-3-carboxylic acid(3-methanesulfonyl-phenyl)-amide;

7-Difluoromethyl-5-[3-(2,2,2-trifluoro-ethoxy)-4-trifluoromethyl-phenyl]-pyrazolo[1,5-a]pyrimidine-3-carboxylic acid(3-methanesulfonyl-phenyl)-amide;

5-(4-Chloro-3-methyl-phenyl)-7-difluoromethyl-pyrazolo[1,5-a]pyrimidine-3-carboxylic acid(3-methanesulfonyl-phenyl)-amide;

5-(3-Fluoro-4-trifluoromethyl-phenyl)-7-trifluoromethyl-pyrazolo[1,5-a]pyrimidine-3-carboxylic acid(3-sulfamoyl-phenyl)-amide;

5-(3-Chloro-4-trifluoromethyl-phenyl)-7-difluoromethyl-pyrazolo[1,5-a]pyrimidine-3-carboxylic acid(3-methanesulfonyl-phenyl)-amide;

7-Difluoromethyl-5-(3-fluoro-4-trifluoromethyl-phenyl)-pyrazolo[1,5-a]pyrimidine-3-carboxylic acid(3-methanesulfonyl-phenyl)-amide;

5-(3-Chloro-4-trifluoromethyl-phenyl)-7-trifluoromethyl-pyrazolo[1,5-a]pyrimidine-3-carboxylic acid(3-methanesulfonyl-phenyl)-amide;

5-(3-Fluoro-4-trifluoromethyl-phenyl)-7-trifluoromethyl-pyrazolo[1,5-a]pyrimidine-3-carboxylic acid(3-methanesulfonyl-phenyl)-amide;

7-Difluoromethyl-5-(4-trifluoromethoxy-phenyl)-pyrazolo[1,5-a]pyrimidine-3-carboxylic acid(3-methanesulfonyl-phenyl)-amide;

5-(4-Trifluoromethoxy-phenyl)-7-trifluoromethyl-pyrazolo[1,5-a]pyrimidine-3-carboxylic acid(3-methanesulfonyl-phenyl)-amide;

5-(3,4-Difluoro-phenyl)-7-trifluoromethyl-pyrazolo[1,5-a]pyrimidine-3-carboxylic acid(3-methanesulfonyl-phenyl)-amide;

5-(4-Chloro-phenyl)-pyrazolo[1,5-a]pyrimidine-3-carboxylic acid(3-methanesulfonyl-phenyl)-amide;

5-(4-Trifluoromethyl-phenyl)-pyrazolo[1,5-a]pyrimidine-3-carboxylic acid(3-methanesulfonyl-phenyl)-amide;

5-(4-Chloro-phenyl)-7-methyl-pyrazolo[1,5-a]pyrimidine-3-carboxylic acid(3-methanesulfonyl-phenyl)-amide;

7-Methyl-5-(4-trifluoromethyl-phenyl)-pyrazolo[1,5-a]pyrimidine-3-carboxylic acid(3-methanesulfonyl-phenyl)-amide;

5-(4-Chloro-phenyl)-7-ethyl-pyrazolo[1,5-a]pyrimidine-3-carboxylic acid(3-methanesulfonyl-phenyl)-amide;

5-(4-Chloro-phenyl)-7-propyl-pyrazolo[1,5-a]pyrimidine-3-carboxylic acid(3-methanesulfonyl-phenyl)-amide;

5-(4-Chloro-phenyl)-7-cyclopropyl-pyrazolo[1,5-a]pyrimidine-3-carboxylic acid(3-methanesulfonyl-phenyl)-amide;

7-Cyclopropyl-5-(4-trifluoromethyl-phenyl)-pyrazolo[1,5-a]pyrimidine-3-carboxylic acid(3-methanesulfonyl-phenyl)-amide;

7-Chloro-5-(4-chloro-phenyl)-pyrazolo[1,5-a]pyrimidine-3-carboxylic acid(3-methanesulfonyl-phenyl)-amide; and 5-(4-Chloro-phenyl)-7-methoxy-pyrazolo[1,5-a]pyrimidine-3-carboxylic acid(3-methanesulfonyl-phenyl)-amide.

Other preferred compounds of the invention are those compounds wherein R³ is hydroxy-lower alkyl; and R¹, R², R⁴, R⁵ and p are as defined hereinabove, for example the following compounds:

7-Trifluoromethyl-5-(4-trifluoromethyl-phenyl)-pyrazolo[1,5-a]pyrimidine-3-carboxylic acid(3-sulfamoylmethyl-phenyl)-amide; and 7-Difluoromethyl-5-(4-trifluoromethyl-phenyl)-pyrazolo[1,5-a]pyrimidine-3-carboxylic acid(3-sulfamoylmethyl-phenyl)-amide.

Still other preferred compounds of the invention are those compounds wherein R³ is NR$^a$R$^b$; wherein R$^a$ and R$^b$ are independently selected from:

H;

lower alkyl optionally substituted by one or more hydroxy, fluoro, cycloalkyl, aryl, heteroaryl, or NR$^c$R$^d$ wherein R$^c$ and R$^d$ are independently selected from H or lower alkyl;

cycloalkyl;

aryl;

heteroaryl;

and $R^1$, $R^2$, $R^4$, $R^5$ and p are as defined hereinabove, for example the following compounds:

7-Trifluoromethyl-5-(4-trifluoromethyl-phenyl)-pyrazolo[1,5-a]pyrimidine-3-carboxylic acid(3-sulfamoyl-phenyl)-amide;

5-(3-Ethoxy-4-trifluoromethyl-phenyl)-7-trifluoromethyl-pyrazolo[1,5-a]pyrimidine-3-carboxylic acid(3-sulfamoyl-phenyl)-amide;

7-Difluoromethyl-5-(3-ethoxy-4-trifluoromethyl-phenyl)-pyrazolo[1,5-a]pyrimidine-3-carboxylic acid(3-sulfamoyl-phenyl)-amide;

7-Difluoromethyl-5-(3-methyl-4-trifluoromethyl-phenyl)-pyrazolo[1,5-a]pyrimidine-3-carboxylic acid(3-sulfamoyl-phenyl)-amide;

5-(3-Methyl-4-trifluoromethyl-phenyl)-7-trifluoromethyl-pyrazolo[1,5-a]pyrimidine-3-carboxylic acid(3-sulfamoyl-phenyl)-amide;

5-(3,4-Dichloro-phenyl)-7-difluoromethyl-pyrazolo[1,5-a]pyrimidine-3-carboxylic acid(3-sulfamoyl-phenyl)-amide;

5-(3,4-Dichloro-phenyl)-7-trifluoromethyl-pyrazolo[1,5-a]pyrimidine-3-carboxylic acid(3-sulfamoyl-phenyl)-amide;

5-(4-Chloro-phenyl)-7-difluoromethyl-pyrazolo[1,5-a]pyrimidine-3-carboxylic acid(3-sulfamoyl-phenyl)-amide;

5-(4-Chloro-3-methyl-phenyl)-7-trifluoromethyl-pyrazolo[1,5-a]pyrimidine-3-carboxylic acid(3-sulfamoyl-phenyl)-amide;

7-Difluoromethyl-5-(4-trifluoromethyl-phenyl)-pyrazolo[1,5-a]pyrimidine-3-carboxylic acid(3-sulfamoyl-phenyl)-amide;

5-(4-Chloro-phenyl)-7-trifluoromethyl-pyrazolo[1,5-a]pyrimidine-3-carboxylic acid(3-sulfamoyl-phenyl)-amide;

5-[3-(2,2,2-Trifluoro-ethoxy)-4-trifluoromethyl-phenyl]-7-trifluoromethyl-pyrazolo[1,5-a]pyrimidine-3-carboxylic acid(3-sulfamoyl-phenyl)-amide;

7-Difluoromethyl-5-[3-(2,2,2-trifluoro-ethoxy)-4-trifluoromethyl-phenyl]-pyrazolo[1,5-a]pyrimidine-3-carboxylic acid(3-sulfamoyl-phenyl)-amide;

5-(4-Chloro-3-methyl-phenyl)-7-difluoromethyl-pyrazolo[1,5-a]pyrimidine-3-carboxylic acid(3-sulfamoyl-phenyl)-amide;

7-Trifluoromethyl-5-(4-trifluoromethyl-phenyl)-pyrazolo[1,5-a]pyrimidine-3-carboxylic acid[3-(2-hydroxy-ethanesulfonyl)-phenyl]-amide;

7-Difluoromethyl-5-(4-trifluoromethyl-phenyl)-pyrazolo[1,5-a]pyrimidine-3-carboxylic acid[3-(2-hydroxy-ethanesulfonyl)-phenyl]-amide;

7-Trifluoromethyl-5-(4-trifluoromethyl-phenyl)-pyrazolo[1,5-a]pyrimidine-3-carboxylic acid(3-ethylsulfamoyl-phenyl)-amide;

7-Trifluoromethyl-5-(4-trifluoromethyl-phenyl)-pyrazolo[1,5-a]pyrimidine-3-carboxylic acid(3-dimethylsulfamoyl-phenyl)-amide;

5-(4-Chloro-3-methyl-phenyl)-7-trifluoromethyl-pyrazolo[1,5-a]pyrimidine-3-carboxylic acid[3-(4-methyl-piperazine-1-sulfonyl)-phenyl]-amide;

7-Difluoromethyl-5-(4-trifluoromethyl-phenyl)-pyrazolo[1,5-a]pyrimidine-3-carboxylic acid(3-ethylsulfamoyl-phenyl)-amide;

7-Difluoromethyl-5-(4-trifluoromethyl-phenyl)-pyrazolo[1,5-a]pyrimidine-3-carboxylic acid(3-dimethylsulfamoyl-phenyl)-amide;

7-Difluoromethyl-5-(4-trifluoromethyl-phenyl)-pyrazolo[1,5-a]pyrimidine-3-carboxylic acid(3-methylsulfamoyl-phenyl)-amide;

7-Difluoromethyl-5-(4-trifluoromethyl-phenyl)-pyrazolo[1,5-a]pyrimidine-3-carboxylic acid(3-cyclopropylsulfamoyl-phenyl)-amide;

7-Difluoromethyl-5-(4-trifluoromethyl-phenyl)-pyrazolo[1,5-a]pyrimidine-3-carboxylic acid(3-isopropylsulfamoyl-phenyl)-amide;

7-Trifluoromethyl-5-(4-trifluoromethyl-phenyl)-pyrazolo[1,5-a]pyrimidine-3-carboxylic acid(3-methylsulfamoyl-phenyl)-amide;

7-Trifluoromethyl-5-(4-trifluoromethyl-phenyl)-pyrazolo[1,5-a]pyrimidine-3-carboxylic acid(3-isopropylsulfamoyl-phenyl)-amide;

7-Difluoromethyl-5-(4-trifluoromethyl-phenyl)-pyrazolo[1,5-a]pyrimidine-3-carboxylic acid[3-(2,2,2-trifluoro-ethylsulfamoyl)-phenyl]-amide;

7-Trifluoromethyl-5-(4-trifluoromethyl-phenyl)-pyrazolo[1,5-a]pyrimidine-3-carboxylic acid[3-(2,2,2-trifluoro-ethylsulfamoyl)-phenyl]-amide;

5-(3-Methyl-4-trifluoromethyl-phenyl)-7-trifluoromethyl-pyrazolo[1,5-a]pyrimidine-3-carboxylic acid(3-cyclopropylsulfamoyl-phenyl)-amide;

5-(3,4-Dichloro-phenyl)-7-trifluoromethyl-pyrazolo[1,5-a]pyrimidine-3-carboxylic acid(3-cyclopropylsulfamoyl-phenyl)-amide;

5-(4-Chloro-phenyl)-7-trifluoromethyl-pyrazolo[1,5-a]pyrimidine-3-carboxylic acid(3-cyclopropylsulfamoyl-phenyl)-amide;

5-(4-Chloro-3-methyl-phenyl)-7-trifluoromethyl-pyrazolo[1,5-a]pyrimidine-3-carboxylic acid(3-cyclopropylsulfamoyl-phenyl)-amide;

7-Difluoromethyl-5-(3-methyl-4-trifluoromethyl-phenyl)-pyrazolo[1,5-a]pyrimidine-3-carboxylic acid(3-cyclopropylsulfamoyl-phenyl)-amide;

5-(3,4-Dichloro-phenyl)-7-difluoromethyl-pyrazolo[1,5-a]pyrimidine-3-carboxylic acid(3-cyclopropylsulfamoyl-phenyl)-amide;

5-(4-Chloro-phenyl)-7-difluoromethyl-pyrazolo[1,5-a]pyrimidine-3-carboxylic acid(3-cyclopropylsulfamoyl-phenyl)-amide;

7-Trifluoromethyl-5-(4-trifluoromethyl-phenyl)-pyrazolo[1,5-a]pyrimidine-3-carboxylic acid(3-isobutylsulfamoyl-phenyl)-amide;

7-Trifluoromethyl-5-(4-trifluoromethyl-phenyl)-pyrazolo[1,5-a]pyrimidine-3-carboxylic acid[3-(cyclopropylmethylsulfamoyl)-phenyl]-amide;

7-Difluoromethyl-5-(3-ethoxy-4-trifluoromethyl-phenyl)-pyrazolo[1,5-a]pyrimidine-3-carboxylic acid(3-cyclopropylsulfamoyl-phenyl)-amide;

5-(3-Ethoxy-4-trifluoromethyl-phenyl)-7-trifluoromethyl-pyrazolo[1,5-a]pyrimidine-3-carboxylic acid(3-cyclopropylsulfamoyl-phenyl)-amide;

7-Difluoromethyl-5-(4-trifluoromethyl-phenyl)-pyrazolo[1,5-a]pyrimidine-3-carboxylic acid(3-isobutylsulfamoyl-phenyl)-amide;

7-Difluoromethyl-5-(4-trifluoromethyl-phenyl)-pyrazolo[1,5-a]pyrimidine-3-carboxylic acid[3-(cyclopropylmethylsulfamoyl)-phenyl]-amide;

7-Difluoromethyl-5-(4-trifluoromethyl-phenyl)-pyrazolo[1,5-a]pyrimidine-3-carboxylic acid(3-benzylsulfamoyl-phenyl)-amide;

7-Trifluoromethyl-5-(4-trifluoromethyl-phenyl)-pyrazolo[1,5-a]pyrimidine-3-carboxylic acid(3-phenylsulfamoyl-phenyl)-amide;

7-Trifluoromethyl-5-(4-trifluoromethyl-phenyl)-pyrazolo[1,5-a]pyrimidine-3-carboxylic acid(3-benzylsulfamoyl-phenyl)-amide;

7-Trifluoromethyl-5-(4-trifluoromethyl-phenyl)-pyrazolo[1,5-a]pyrimidine-3-carboxylic acid[3-(2-hydroxy-ethylsulfamoyl)-phenyl]-amide;

7-Difluoromethyl-5-(4-trifluoromethyl-phenyl)-pyrazolo[1,5-a]pyrimidine-3-carboxylic acid[3-(2-hydroxy-ethylsulfamoyl)-phenyl]-amide;

7-Trifluoromethyl-5-(4-trifluoromethyl-phenyl)-pyrazolo[1,5-a]pyrimidine-3-carboxylic acid(3-trifluoromethanesulfonyl-phenyl)-amide;

7-Difluoromethyl-5-(4-trifluoromethyl-phenyl)-pyrazolo[1,5-a]pyrimidine-3-carboxylic acid(3-trifluoromethanesulfonyl-phenyl)-amide;

7-Difluoromethyl-5-(4-trifluoromethyl-phenyl)-pyrazolo[1,5-a]pyrimidine-3-carboxylic acid[3-(2,2-dimethyl-propylsulfamoyl)-phenyl]-amide;

7-Difluoromethyl-5-(4-trifluoromethyl-phenyl)-pyrazolo[1,5-a]pyrimidine-3-carboxylic acid(3-tert-butylsulfamoyl-phenyl)-amide;

7-Trifluoromethyl-5-(4-trifluoromethyl-phenyl)-pyrazolo[1,5-a]pyrimidine-3-carboxylic acid[3-(2,2-dimethyl-propylsulfamoyl)-phenyl]-amide;

7-Trifluoromethyl-5-(4-trifluoromethyl-phenyl)-pyrazolo[1,5-a]pyrimidine-3-carboxylic acid(3-tert-butylsulfamoyl-phenyl)-amide;

5-(3-Chloro-4-trifluoromethyl-phenyl)-7-difluoromethyl-pyrazolo[1,5-a]pyrimidine-3-carboxylic acid(3-sulfamoyl-phenyl)-amide;

7-Difluoromethyl-5-(3-fluoro-4-trifluoromethyl-phenyl)-pyrazolo[1,5-a]pyrimidine-3-carboxylic acid(3-sulfamoyl-phenyl)-amide;

5-(3-Chloro-4-trifluoromethyl-phenyl)-7-trifluoromethyl-pyrazolo[1,5-a]pyrimidine-3-carboxylic acid(3-sulfamoyl-phenyl)-amide;

7-Difluoromethyl-5-(4-trifluoromethyl-phenyl)-pyrazolo[1,5-a]pyrimidine-3-carboxylic acid{3-[(pyridin-3-ylmethyl)-sulfamoyl]-phenyl}-amide;

7-Trifluoromethyl-5-(4-trifluoromethyl-phenyl)-pyrazolo[1,5-a]pyrimidine-3-carboxylic acid{3-[(pyridin-3-ylmethyl)-sulfamoyl]-phenyl}-amide;

7-Difluoromethyl-5-(4-trifluoromethyl-phenyl)-pyrazolo[1,5-a]pyrimidine-3-carboxylic acid{3-[(pyridin-2-ylmethyl)-sulfamoyl]-phenyl}-amide;

7-Trifluoromethyl-5-(4-trifluoromethyl-phenyl)-pyrazolo[1,5-a]pyrimidine-3-carboxylic acid{3-[(pyridin-2-ylmethyl)-sulfamoyl]-phenyl}-amide;

7-Difluoromethyl-5-(4-trifluoromethyl-phenyl)-pyrazolo[1,5-a]pyrimidine-3-carboxylic acid[3-(2-pyridin-4-yl-ethylsulfamoyl)-phenyl]-amide;

7-Trifluoromethyl-5-(4-trifluoromethyl-phenyl)-pyrazolo[1,5-a]pyrimidine-3-carboxylic acid[3-(2-pyridin-4-yl-ethylsulfamoyl)-phenyl]-amide;

7-Difluoromethyl-5-(4-trifluoromethyl-phenyl)-pyrazolo[1,5-a]pyrimidine-3-carboxylic acid[3-(2-hydroxy-1,1-dimethyl-ethylsulfamoyl)-phenyl]-amide;

7-Trifluoromethyl-5-(4-trifluoromethyl-phenyl)-pyrazolo[1,5-a]pyrimidine-3-carboxylic acid[3-(2-hydroxy-1,1-dimethyl-ethylsulfamoyl)-phenyl]-amide;

7-Difluoromethyl-5-(4-trifluoromethoxy-phenyl)-pyrazolo[1,5-a]pyrimidine-3-carboxylic acid(3-sulfamoyl-phenyl)-amide;

5-(4-Trifluoromethoxy-phenyl)-7-trifluoromethyl-pyrazolo[1,5-a]pyrimidine-3-carboxylic acid(3-sulfamoyl-phenyl)-amide;

5-(3,4-Difluoro-phenyl)-7-trifluoromethyl-pyrazolo[1,5-a]pyrimidine-3-carboxylic acid(3-sulfamoyl-phenyl)-amide;

5-(4-Chloro-phenyl)-7-trifluoromethyl-pyrazolo[1,5-a]pyrimidine-3-carboxylic acid[3-(2-hydroxy-1,1-dimethyl-ethylsulfamoyl)-phenyl]-amide;

5-(3-Chloro-4-trifluoromethyl-phenyl)-7-trifluoromethyl-pyrazolo[1,5-a]pyrimidine-3-carboxylic acid[3-(2-hydroxy-1,1-dimethyl-ethylsulfamoyl)-phenyl]-amide;

5-[3-(2,2,2-Trifluoro-ethoxy)-4-trifluoromethyl-phenyl]-7-trifluoromethyl-pyrazolo[1,5-a]pyrimidine-3-carboxylic acid[3-(2-hydroxy-1,1-dimethyl-ethylsulfamoyl)-phenyl]-amide;

5-(3-Methyl-4-trifluoromethyl-phenyl)-7-trifluoromethyl-pyrazolo[1,5-a]pyrimidine-3-carboxylic acid[3-(2-hydroxy-1,1-dimethyl-ethylsulfamoyl)-phenyl]-amide;

5-(3-Ethoxy-4-trifluoromethyl-phenyl)-7-trifluoromethyl-pyrazolo[1,5-a]pyrimidine-3-carboxylic acid[3-(2-hydroxy-1,1-dimethyl-ethylsulfamoyl)-phenyl]-amide;

5-(3,4-Dichloro-phenyl)-7-trifluoromethyl-pyrazolo[1,5-a]pyrimidine-3-carboxylic acid[3-(2-hydroxy-1,1-dimethyl-ethylsulfamoyl)-phenyl]-amide;

5-(3-Fluoro-4-trifluoromethyl-phenyl)-7-trifluoromethyl-pyrazolo[1,5-a]pyrimidine-3-carboxylic acid[3-(2-hydroxy-1,1-dimethyl-ethylsulfamoyl)-phenyl]-amide;

5-(4-Trifluoromethoxy-phenyl)-7-trifluoromethyl-pyrazolo[1,5-a]pyrimidine-3-carboxylic acid[3-(2-hydroxy-1,1-dimethyl-ethylsulfamoyl)-phenyl]-amide;

5-(4-Chloro-phenyl)-7-difluoromethyl-pyrazolo[1,5-a]pyrimidine-3-carboxylic acid[3-(2-hydroxy-1,1-dimethyl-ethylsulfamoyl)-phenyl]-amide;

7-Difluoromethyl-5-(3-ethoxy-4-trifluoromethyl-phenyl)-pyrazolo[1,5-a]pyrimidine-3-carboxylic acid[3-(2-hydroxy-1,1-dimethyl-ethylsulfamoyl)-phenyl]-amide;

7-Difluoromethyl-5-(4-trifluoromethyl-phenyl)-pyrazolo[1,5-a]pyrimidine-3-carboxylic acid(4-methyl-3-sulfamoyl-phenyl)-amide;

7-Trifluoromethyl-5-(4-trifluoromethyl-phenyl)-pyrazolo[1,5-a]pyrimidine-3-carboxylic acid(4-methyl-3-sulfamoyl-phenyl)-amide;

7-Difluoromethyl-5-(4-trifluoromethyl-phenyl)-pyrazolo[1,5-a]pyrimidine-3-carboxylic acid{3-[bis-(2-hydroxy-ethyl)-sulfamoyl]-phenyl}-amide;

7-Trifluoromethyl-5-(4-trifluoromethyl-phenyl)-pyrazolo[1,5-a]pyrimidine-3-carboxylic acid{3-[bis-(2-hydroxy-ethyl)-sulfamoyl]-phenyl}-amide;

7-Difluoromethyl-5-(4-trifluoromethyl-phenyl)-pyrazolo[1,5-a]pyrimidine-3-carboxylic acid[3-(2-hydroxy-1-hydroxymethyl-1-methyl-ethylsulfamoyl)-phenyl]-amide;

7-Trifluoromethyl-5-(4-trifluoromethyl-phenyl)-pyrazolo[1,5-a]pyrimidine-3-carboxylic acid[3-(2-hydroxy-1-hydroxymethyl-1-methyl-ethylsulfamoyl)-phenyl]-amide;

7-Trifluoromethyl-5-(4-trifluoromethyl-phenyl)-pyrazolo[1,5-a]pyrimidine-3-carboxylic acid(2-methyl-5-sulfamoyl-phenyl)-amide;

7-Difluoromethyl-5-(4-trifluoromethyl-phenyl)-pyrazolo[1,5-a]pyrimidine-3-carboxylic acid(2-methyl-5-sulfamoyl-phenyl)-amide;

7-Trifluoromethyl-5-(4-trifluoromethyl-phenyl)-pyrazolo[1,5-a]pyrimidine-3-carboxylic acid(2-chloro-5-sulfamoyl-phenyl)-amide;

7-Difluoromethyl-5-(4-trifluoromethyl-phenyl)-pyrazolo[1,5-a]pyrimidine-3-carboxylic acid(2-chloro-5-sulfamoyl-phenyl)-amide;

7-Trifluoromethyl-5-(4-trifluoromethyl-phenyl)-pyrazolo[1,5-a]pyrimidine-3-carboxylic acid[2-chloro-5-(2-hydroxy-1,1-dimethyl-ethylsulfamoyl)-phenyl]-amide;

7-Difluoromethyl-5-(4-trifluoromethyl-phenyl)-pyrazolo[1,5-a]pyrimidine-3-carboxylic acid[2-chloro-5-(2-hydroxy-1,1-dimethyl-ethylsulfamoyl)-phenyl]-amide;

7-Trifluoromethyl-5-(4-trifluoromethyl-phenyl)-pyrazolo[1,5-a]pyrimidine-3-carboxylic acid[5-(2-hydroxy-1,1-dimethyl-ethylsulfamoyl)-2-methyl-phenyl]-amide;

7-Difluoromethyl-5-(4-trifluoromethyl-phenyl)-pyrazolo[1,5-a]pyrimidine-3-carboxylic acid[5-(2-hydroxy-1,1-dimethyl-ethylsulfamoyl)-2-methyl-phenyl]-amide;

7-Difluoromethyl-5-(4-trifluoromethyl-phenyl)-pyrazolo[1,5-a]pyrimidine-3-carboxylic acid[3-(2-dimethylamino-ethylsulfamoyl)-phenyl]-amide;

7-Trifluoromethyl-5-(4-trifluoromethyl-phenyl)-pyrazolo[1,5-a]pyrimidine-3-carboxylic acid[3-(2-dimethylamino-ethylsulfamoyl)-phenyl]-amide;

5-(4-Chloro-phenyl)-7-trifluoromethyl-pyrazolo[1,5-a]pyrimidine-3-carboxylic acid[3-(1-hydroxymethyl-cyclopentylsulfamoyl)-phenyl]-amide;

5-(4-Chloro-phenyl)-pyrazolo[1,5-a]pyrimidine-3-carboxylic acid(3-sulfamoyl-phenyl)-amide;

5-(4-Trifluoromethyl-phenyl)-pyrazolo[1,5-a]pyrimidine-3-carboxylic acid(3-sulfamoyl-phenyl)-amide;

5-(4-Chloro-phenyl)-7-methyl-pyrazolo[1,5-a]pyrimidine-3-carboxylic acid(3-sulfamoyl-phenyl)-amide;

5-(4-Chloro-phenyl)-7-methyl-pyrazolo[1,5-a]pyrimidine-3-carboxylic acid[3-(2-hydroxy-1,1-dimethyl-ethylsulfamoyl)-phenyl]-amide;

7-Methyl-5-(4-trifluoromethyl-phenyl)-pyrazolo[1,5-a]pyrimidine-3-carboxylic acid(3-sulfamoyl-phenyl)-amide;

5-(4-Chloro-phenyl)-7-ethyl-pyrazolo[1,5-a]pyrimidine-3-carboxylic acid(3-sulfamoyl-phenyl)-amide;

5-(4-Chloro-phenyl)-7-ethyl-pyrazolo[1,5-a]pyrimidine-3-carboxylic acid[3-(2-hydroxy-1,1-dimethyl-ethylsulfamoyl)-phenyl]-amide;

5-(4-Chloro-phenyl)-7-propyl-pyrazolo[1,5-a]pyrimidine-3-carboxylic acid(3-sulfamoyl-phenyl)-amide;

5-(4-Chloro-phenyl)-7-propyl-pyrazolo[1,5-a]pyrimidine-3-carboxylic acid[3-(2-hydroxy-1,1-dimethyl-ethylsulfamoyl)-phenyl]-amide;

5-(4-Chloro-phenyl)-7-cyclopropyl-pyrazolo[1,5-a]pyrimidine-3-carboxylic acid(3-sulfamoyl-phenyl)-amide;

5-(4-Chloro-phenyl)-7-cyclopropyl-pyrazolo[1,5-a]pyrimidine-3-carboxylic acid[3-(2-hydroxy-1,1-dimethyl-ethylsulfamoyl)-phenyl]-amide;

5-(4-Chloro-phenyl)-7-cyclopropyl-pyrazolo[1,5-a]pyrimidine-3-carboxylic acid(3-tert-butylsulfamoyl-phenyl)-amide;

5-(4-Chloro-phenyl)-7-cyclopropyl-pyrazolo[1,5-a]pyrimidine-3-carboxylic acid[3-(1-hydroxymethyl-cyclopentylsulfamoyl)-phenyl]-amide;

5-(4-Chloro-phenyl)-7-cyclopropyl-pyrazolo[1,5-a]pyrimidine-3-carboxylic acid[5-(2-hydroxy-1,1-dimethyl-ethylsulfamoyl)-2-methyl-phenyl]-amide;

7-Cyclopropyl-5-(4-trifluoromethyl-phenyl)-pyrazolo[1,5-a]pyrimidine-3-carboxylic acid(3-sulfamoyl-phenyl)-amide;

7-Cyclopropyl-5-(4-trifluoromethyl-phenyl)-pyrazolo[1,5-a]pyrimidine-3-carboxylic acid[3-(2-hydroxy-1,1-dimethyl-ethylsulfamoyl)-phenyl]-amide;

7-Cyclopropyl-5-(4-trifluoromethyl-phenyl)-pyrazolo[1,5-a]pyrimidine-3-carboxylic acid(3-tert-butylsulfamoyl-phenyl)-amide; and 7-Cyclopropyl-5-(4-trifluoromethyl-phenyl)-pyrazolo[1,5-a]pyrimidine-3-carboxylic acid[5-(2-hydroxy-1,1-dimethyl-ethylsulfamoyl)-2-methyl-phenyl]-amide.

Other preferred compounds of the invention are those compounds wherein $R^3$ is 4-morpholinyl; and $R^1$, $R^2$, $R^4$, $R^5$ and p are as defined hereinabove, for example the following compounds:

7-Trifluoromethyl-5-(4-trifluoromethyl-phenyl)-pyrazolo[1,5-a]pyrimidine-3-carboxylic acid[3-(morpholine-4-sulfonyl)-phenyl]-amide;

7-Difluoromethyl-5-(4-trifluoromethyl-phenyl)-pyrazolo[1,5-a]pyrimidine-3-carboxylic acid[3-(morpholine-4-sulfonyl)-phenyl]-amide;

5-(4-Chloro-phenyl)-7-difluoromethyl-pyrazolo[1,5-a]pyrimidine-3-carboxylic acid[3-(morpholine-4-sulfonyl)-phenyl]-amide;

5-(4-Chloro-phenyl)-7-trifluoromethyl-pyrazolo[1,5-a]pyrimidine-3-carboxylic acid[3-(morpholine-4-sulfonyl)-phenyl]-amide;

7-Difluoromethyl-5-(3-methyl-4-trifluoromethyl-phenyl)-pyrazolo[1,5-a]pyrimidine-3-carboxylic acid[3-(morpholine-4-sulfonyl)-phenyl]-amide;

5-(4-Chloro-3-methyl-phenyl)-7-trifluoromethyl-pyrazolo[1,5-a]pyrimidine-3-carboxylic acid[3-(morpholine-4-sulfonyl)-phenyl]-amide;

5-(3,4-Dichloro-phenyl)-7-difluoromethyl-pyrazolo[1,5-a]pyrimidine-3-carboxylic acid[3-(morpholine-4-sulfonyl)-phenyl]-amide;

5-(3,4-Dichloro-phenyl)-7-trifluoromethyl-pyrazolo[1,5-a]pyrimidine-3-carboxylic acid[3-(morpholine-4-sulfonyl)-phenyl]-amide;

5-(3-Methyl-4-trifluoromethyl-phenyl)-7-trifluoromethyl-pyrazolo[1,5-a]pyrimidine-3-carboxylic acid[3-(morpholine-4-sulfonyl)-phenyl]-amide; and 5-(3-Ethoxy-4-trifluoromethyl-phenyl)-7-trifluoromethyl-pyrazolo[1,5-a]pyrimidine-3-carboxylic acid[3-(morpholine-4-sulfonyl)-phenyl]-amide.

Still other preferred compounds of the invention are those compounds $R^3$ is pyrrolidine and $R^1$, $R^2$, $R^4$, $R^5$ and p are as defined hereinabove, for example the following compounds:

7-Trifluoromethyl-5-(4-trifluoromethyl-phenyl)-pyrazolo[1,5-a]pyrimidine-3-carboxylic acid[3-(pyrrolidine-1-sulfonyl)-phenyl]-amide;

5-(4-Chloro-phenyl)-7-trifluoromethyl-pyrazolo[1,5-a]pyrimidine-3-carboxylic acid[3-(pyrrolidine-1-sulfonyl)-phenyl]-amide;

7-Difluoromethyl-5-(3-methyl-4-trifluoromethyl-phenyl)-pyrazolo[1,5-a]pyrimidine-3-carboxylic acid[3-(pyrrolidine-1-sulfonyl)-phenyl]-amide;

5-(4-Chloro-3-methyl-phenyl)-7-trifluoromethyl-pyrazolo[1,5-a]pyrimidine-3-carboxylic acid[3-(pyrrolidine-1-sulfonyl)-phenyl]-amide;

5-(4-Chloro-phenyl)-7-trifluoromethyl-pyrazolo[1,5-a]pyrimidine-3-carboxylic acid[3-((S)-2-hydroxymethyl-pyrrolidine-1-sulfonyl)-phenyl]-amide; and 5-(4-Chloro-phenyl)-7-cyclopropyl-pyrazolo[1,5-a]pyrimidine-3-carboxylic acid[3-((S)-2-hydroxymethyl-pyrrolidine-1-sulfonyl)-phenyl]-amide.

In one embodiment, the invention provides compounds wherein one or both of $R^1$ and $R^2$ are hydrogen. In another embodiment, the invention provides compounds wherein one or both of $R^1$ and $R^2$ are halogen. In yet another embodiment, the present invention provides compounds where $R^1$ and/or $R^2$ are each independently lower alkyl optionally substituted by lower alkoxy. In another embodiment, the invention provides compounds where $R^1$ and/or $R^2$ are each independently lower alkoxy optionally substituted by one or more halogen.

In one embodiment, the present invention provides compounds wherein $R^4$ is hydrogen, chlorine, or lower alkoxy. In another embodiment, the invention provides compounds wherein $R^4$ is cycloalkyl or straight lower alkyl which is optionally substituted by one or more F.

The compounds of the invention can be prepared according to a process comprising reacting a compound of formula VI

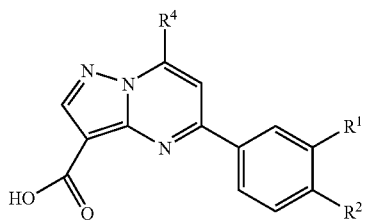

with a compound of formula VII

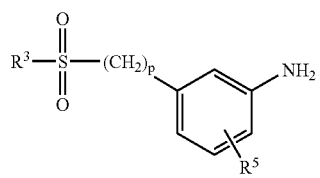

wherein $R^1$, $R^2$, $R^3$, $R^4$, $R^5$ and p are as defined in formula I above; to obtain the compound of formula I, and if desired converting the compound of formula I into its pharmaceutically acceptable addition salt.

The pharmaceutically acceptable addition salts can be manufactured readily according to methods known per se and taking into consideration the nature of the compound to be converted into a salt. Inorganic or organic acids such as, for example, hydrochloric acid, hydrobromic acid, sulphuric acid, nitric acid, phosphoric acid or citric acid, formic acid, fumaric acid, maleic acid, acetic acid, succinic acid, tartaric acid, methanesulphonic acid, p-toluenesulphonic acid and the like are suitable for the formation of pharmaceutically acceptable salts of basic compounds of formula I.

The synthesis of the intermediate compounds of formula (VI) above may be carried out in accordance with the following general procedures I and/or Ia which procedures are outlined below in scheme 1 and scheme 1a. The procedure given in scheme 1 is convenient for intermediate compounds VI wherein $R^4$ is $CF_3$ or $CHF_2$, whereas for intermediate compounds VI wherein $R^4$ is linear $C_{1-3}$ alkyl or cyclopropyl, the procedure outlined in scheme 1a is preferred. Nevertheless, procedures I/Ia and II are applicable for the preparation of all the compounds according to formula I. i.e. for other meanings of $R^4$ as recited hereinabove.

As for the reaction of the compound of formula (VII) with a compound of formula (VI), it may be for example carried out in accordance with the following general procedure II which procedure is outlined below in scheme 2. In these schemes (I, Ia, and II), $R^1$, $R^2$, $R^3$, $R^4$, $R^5$ and p are as defined hereinabove and compounds of formulae II, VII and VIII are commercially available.

General Procedure I

Error! Objects Cannot be Created From Editing Field Codes.

Step 1.1:

To a stirred solution of compound of formula (VIII) in an organic solvent (e.g. tert.-butyl-methyl-ether) is added at room temperature a solution of sodium methoxide in methanol followed by a solution of compound of formula (II) in an organic solvent (e.g. tert.-butyl-methyl-ether). The reaction mixture is stirred at room temperature for about 19 h, cooled, acidified and extracted (e.g. with diethyl ether). The combined organic layers are washed and dried (e.g. with $MgSO_4$) and evaporated to give crude compound of formula (IV) which can be used without further purification.

Step 1.2:

A stirred mixture of commercially available 3-amino-4-ethoxycarbonyl-pyrazole (compound of formula (V)) and compound of formula (IV) in an organic acid (e.g. acetic acid) is heated under reflux conditions for about 1.5 h. The reaction mixture is evaporated and the crude product is dissolved in a mixture of a concentrated base (e.g. KOH in methanol and water). The reaction mixture is stirred at about 60° C. for about 1.5 h, cooled, acidified and concentrated. The precipitate is collected by filtration and further purified (e.g. by crystallization from diethal ether/methanol) to give the compound of formula (VI).

General Procedure Ia

Error! Objects Cannot be Created from Editing Field Codes.

Step 1a.1:

To a suspension of sodium hydride in toluene are added subsequently diethyl carbonate (VIII) and a compound of formula (II). The solution is slowly warmed up to 100° C. during which process hydrogen gas is produced. The mixture is stirred at reflux temperature for 6 to 15 h. After cooling the mixture to 10° C., acetic acid is added followed by ice-water and conc. HCl. The mixture was extracted (e.g. with ethyl acetate). The organic layer is successively washed with aqueous $NaHCO_3$ solution, water and brine, dried (e.g. with $Na_2SO_4$), and evaporated. The remaining crude product of formula (IX) can be used directly in the next step or, optionally, is purified, e.g. by distillation.

Step 1a.2:

A mixture of a compound of formula (IX) and 3-amino-4-ethoxycarbonyl-pyrazole (compound of formula (V)) is heated, either neat with stirring to about 150° C. for 2 to 6 h, or preferably in a solvent (such as e.g. acetic acid) for 8 to 20 h). The product of formula (X) can be isolated by a conventional work-up procedure, e. g. by precipitation of the product with water or partitioning of the reaction mixture between water and an organic solvent, such as dichloromethane, and the crude product may be further purified, e.g. by crystallization.

Step 1a.3:

A compound of formula (X) is heated with stirring with $POCl_3$ to 80 to 100° C. for 1 to 15 h, preferably in the presence of a basic catalyst (e.g. dimethyl aniline). The mixture is cooled and evaporated in vacuo. The residue is partitioned between water and an organic solvent (e.g. dichloromethane or ethyl acetate), the organic layers are washed with water and brine, dried (e.g. with $Na_2SO_4$), and evaporated. The remaining crude product of formula (XI) can be used directly in the next step or, preferably, is purified, e.g. by crystallization.

Step 1a.4:

For the preparation of a compound (XIII), wherein $R^4$ represents linear $C_{1-3}$-alkyl or cyclopropyl, a solution of a compound of formula (XIII), a reagent $R^4ZnCl$ (XII) or $Zn(R^4)_2$ (XIIa), and a Pd(0) catalyst (e.g. $Pd(PPh_3)_4$ in THF is heated to 40 to 70° C. for 0.5 to 6 h. To the cooled reaction mixture is added saturated aqueous ammonium chloride. The mixture is extracted with ethyl acetate, and the organic layers are washed with water and brine, dried (e.g. with Na$_2$SO$_4$), and evaporated. The crude product can be used directly in the next step, or firstly be purified by chromatography and/or crystallisation.

For the preparation of a compound (XIII), wherein R$^4$ represents hydrogen, a solution of a compound of formula (XIII) in a solvent (e.g. in ethanol) is stirred in an atmosphere of hydrogen in the presence of palladium on charcoal and of a base (e.g. triethylamine) at 20° C. for 0.1-0.3 h. The mixture is filtered and the solvent is evaporated to afford a compound of formula (XIII) wherein R$^4$ is hydrogen.

Step 1a.5:

An intermediate compound VI, wherein R$^4$ is linear C$_{1-3}$ alkyl or cyclopropyl, can be prepared by subjecting an intermediate compound (XIII) to conventional procedures used to hydrolyze ethyl esters, e.g. by treatment with an aqueous base, such as 2N sodium hydroxide solution, optionally in the presence of a co-solvent, such as methanol, at 20-70° C.

General Procedure II

Error! Objects Cannot be Created from Editing Field Codes.

Step 2.1:

To a stirred solution of compound of formula (VI) in a solvent (e.g. THF) is added at room temperature DMF, the solution is cooled to about 0° C. and oxalyl chloride is added. The reaction mixture is stirred at room temperature for about 3 h and evaporated to dryness. The precipitate is dissolved in pyridine and, while stirring at room temperature, 4-dimethylamino-pyridine and a compound of formula (VII) are added. The reaction mixture is allowed to stir at room temperature for about 16 h, evaporated to dryness and the crude product is purified (e.g. by flash chromatography on silica gel) to yield the product, which can be further purified (e.g. by crystallization from methanol/hexane).

The compounds of formula I and their pharmaceutically acceptable salts are metabotropic glutamate receptor antagonists and can be used for the treatment or prevention of acute and/or chronic neurological disorders, such as psychosis, schizophrenia, Alzheimer's disease, cognitive disorders and memory deficits. Other treatable indications are restricted brain function caused by bypass operations or transplants, poor blood supply to the brain, spinal cord injuries, head injuries, hypoxia caused by pregnancy, cardiac arrest and hypoglycaemia. Further treatable indications are acute and chronic pain, Huntington's chorea, ALS, dementia caused by AIDS, eye injuries, retinopathy, idiopathic parkinsonism or parkinsonism caused by medicaments as well as conditions which lead to glutamate-deficient functions, such as e.g. muscle spasms, convulsions, migraine, urinary incontinence, nicotine addiction, psychoses, opiate addiction, anxiety, vomiting, dyskinesia depression and glioma since mGluR2 antagonists have been found to reduce cell proliferation in human glioma cells (J. Neurochem. March 2003, 84(6): 1288-95).

The present invention also provides pharmaceutical compositions containing compounds of the invention or pharmaceutically acceptable salts thereof and a pharmaceutically acceptable carrier. Such pharmaceutical compositions can be in the form of tablets, coated tablets, dragées, hard and soft gelatine capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acid or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like; depending on the nature of the active substance no carriers are, however, usually required in the case of soft gelatine capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula I, but as a rule are not necessary. Suitable carriers for suppositories are, for example, natural or hardened oils, waxes, fats, semi-liquid or liquid polyols and the like.

In addition, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a method for the manufacture of pharmaceutical compositions. Such process comprises bringing one or more compounds of the invention or pharmaceutically acceptable salts thereof and, if desired, one or more other therapeutically valuable substances into a galenical dosage form together with one or more therapeutically inert carriers.

The compounds and compositions of the invention can be administered in a conventional manner, for example, orally, rectally, or parenterally. The pharmaceutical compositions of the invention can be administered orally, for example, in the form of tablets, coated tablets, dragées, hard and soft gelatine capsules, solutions, emulsions, or suspensions. The pharmaceutical compositions also can be administered rectally, for example, in the form of suppositories, or parenterally, for example, in the form of injectable solutions.

Compounds of the present invention are metabotropic glutamate receptor antagonists. Thus, the present invention provides a method for the treatment of acute and/or chronic neurological disorders, which comprises administering to an individual a therapeutically effective amount of a compound of formula I or a pharmaceutically acceptable salt thereof. In particular, the invention provides a method for the treatment of psychosis, schizophrenia, Alzheimer's disease, cognitive disorders, memory deficits, and glioma which comprises administering to an individual a therapeutically effective amount of a compound of formula I or a pharmaceutically acceptable salt thereof. The invention further provides a method for the treatment of Alzheimer's disease which comprises administering to an individual a therapeutically effective amount of a compound of formula I or a pharmaceutically acceptable salt thereof. The invention further provides a method for the treatment of schizophrenia which comprises administering to an individual a therapeutically effective amount of a compound of formula I or a pharmaceutically acceptable salt thereof.

The dosage at which the compound of the invention is administered can vary within wide limits and will, of course, be fitted to the individual requirements in each particular case. In general, the effective dosage for oral or parenteral administration is between 0.01-20 mg/kg/day, with a dosage of 0.1-10 mg/kg/day being preferred for all of the indications described. The daily dosage for an adult human being weighing 70 kg accordingly lies between 0.7-1400 mg per day, preferably between 7 and 700 mg per day.

The compounds of the present invention are group II mGlu receptor antagonists. The compounds show activities, as measured in the assay described below, of 0.060 µM or less, typically 0.025 µM or less, and ideally of 0.010 µM or less. In the table below are described some specific Ki values of preferred compounds.

|  | Ex. No. | | | | |
| --- | --- | --- | --- | --- | --- |
|  | 1 | 74 | 79 | 88 | 144 |
| $K_i$ mGlu2 (µM) | 0.03 | 0.067 | 0.011 | 0.015 | 0.007 |

[$^3$H]-LY354740 Binding on mGlu2 Transfected CHO Cell Membranes.

Transfection and Cell Culture cDNA encoding the rat mGlu2 receptor protein in pBluescript II was subcloned into the eukaryotic expression vector pcDNA I-amp from Invitrogen Ltd (Paisley, UK). This vector construct (pcD1mGR2) was co-transfected with a psvNeo plasmid encoding the gene for neomycin resistance, into CHO cells by a modified calcium phosphate method described by Chen & Okayama (1988). The cells were maintained in Dulbecco's Modified Eagle medium with reduced L-glutamine (2 mM final concentration) and 10% dialysed foetal calf serum from Gibco-Invitrogen (Carlsbad, Calif., USA). Selection was made in the presence of G-418 (1000 ug/ml final) and MCPG??. Clones were identified by reverse transcription of 5 µg total RNA, followed by PCR using mGlu2 receptor specific primers 5'-atcactgct-tgggtttctggcactg-3' and 5'-agcatcactgtgggtggcataggagc-3' in 60 mM Tris HCl (pH 10), 15 mM ($NH_4$)$_2SO_4$, 2 mM $MgCl_2$, 25 units/ml Taq Polymerase with 30 cycles annealing at 60° C. for 1 min., extention at 72° C. for 30 s, and 1 min. 95° C. denaturation.

Membrane Preparation

Cells, cultured as above, were harvested and washed three times with cold PBS and frozen at −80° C. The pellet was resuspended in cold 20 mM HEPES-NaOH buffer containing 10 mM EDTA (pH 7.4), and homogenised with a polytron (Kinematica, AG, Littau, Switzerland) for 10 s at 10 000 rpm. After centrifugation for 30 min. at 4° C., the pellet was washed once with the same buffer, and once with cold 20 mM HEPES-NaOH buffer containing 0.1 mM EDTA, (pH 7.4). Protein content was measured using the micro BCA method from Pierce-Perbio (Rockford, Ill., USA) using bovine serum albumin as standard.

[$^3$H]-LY354740 Binding

After thawing, the membranes were resuspended in cold 50 mM Tris-HCl buffer containing 2 mM $MgCl_2$ (pH 7) (binding buffer). The final concentration of the membranes in the assays was 25 µg protein/ml. Inhibition experiments were performed with membranes incubated with 10 nM [$^3$H]-LY354740 at room temperature, for 1 hour, in presence of various concentrations of the compound to be tested. Following the incubations, membranes were filtered onto Whatmann GF/B glass fiber filters and washed 5 times with cold binding buffer. Non specific binding was measured in the presence of 10 µM DCG IV. After transfer of the filters into plastic vials containing 10 ml of Ultima-gold scintillation fluid from Perkin-Elmer (Boston, Mass., USA), the radioactivity was measured by liquid scintillation in a Tri-Carb 2500 TR counter (Packard, Zürich, Switzerland).

Data Analysis.

The inhibition curves were fitted with a four parameter logistic equation giving $IC_{50}$ values, and Hill coefficients.

EXAMPLES

Synthesis of Starting Material

Some of the starting material used in the general procedures I and II is commercially available. However some of said starting material has been prepared according to the procedures as outlined hereafter and unless otherwise specified, the intermediate compounds described therein are novel compounds. Other starting material useful in the general procedures I and II may be prepared taking into account the following examples of preparation and using known methods:

Synthesis of Acetophenones Derivatives (Starting Material of Formula II)

Example A.1

4-Methyl-3-trifluoromethyl-acetophenone

To a stirred and cooled (0° C.) solution of potassium tert.-butanolate (1.39 g, 12 mmol) in DMSO (3 ml) was added diethyl malonate (1.9 ml, 12 mmol) and the reaction mixture was stirred for 20 min at room temperature. To the white suspension was added at room temperature 4-fluoro-3-trifluoromethyl-acetophenone (1 g, 5 mmol) and DMSO (2 ml). The reaction mixture was stirred for 6 h at 60° C. and for 16 h at room temperature. The reaction mixture was cooled (0° C.), a solution of potassium hydroxide (1.09 g, 19 mmol) in water (2 ml) was added and the mixture was stirred at 100° C. for 23 h. The mixture was poured into ice/water (40 ml) and extracted with diethyl ether (2×40 ml). The combined organic layers were washed with water (3×30 ml), brine (30 ml), dried ($MgSO_4$) and evaporated. The crude product (0.92 g) was further purified by column chromatography on silica gel (heptane/ethyl acetate 3:1) to give the title compound (0.76 g, 77%) as a light yellow liquid. MS (EI) 202.0 [M].

Example A.2

4-Ethoxy-3-trifluoromethyl-acetophenone

To a stirred suspension of potassium ethanolate (2.36 g, 27 mmol) in ethanol (30 ml) was added at room temperature a solution of 4-fluoro-3-trifluoromethyl-acetophenone (2.5 g, 12 mmol) in ethanol (10 ml). The reaction mixture was stirred at 60° C. for 2 h and evaporated. Ice/2 N HCl (50 ml) was added and the water layer was extracted with diethylether (2×100 ml). The combined organic layers were washed with ice-water (50 ml), brine (50 ml), dried ($MgSO_4$) and evaporated to give the title compound (2.9 g, 98%) as a brown solid, which was used without further purification. MS (EI) 232.1 [M].

Example A.3

4-(2,2,2-Trifluoro-ethoxy)-3-trifluoromethyl-acetophenone

To a stirred solution of 4-fluoro-3-trifluoromethyl-acetophenone (2.5 g, 12 mmol) in DMSO (15 ml) was added at room temperature 2,2,2-trifluoroethanol (1.7 g, 17 mmol) and potassium hydroxide (1.74 g, 27 mmol). The reaction mixture was stirred for 30 min at 40° C., ice/2N HCl (50 ml) was added and the water layer was extracted with diethyl-ether (2×100 ml). The combined organic layers were washed with ice-water (50 ml), brine (50 ml), dried (MgSO$_4$) and evaporated to give the title compound (3.6 g, 98%) as a brown solid, which was used without further purification. MS (EI) 286.1 [M].

Example A.4

3-Methyl-4-trifluoromethyl-acetophenone

The 1-(3-methyl-4-trifluoromethyl-phenyl)-ethanone was prepared by the following sequence:

Step 1: 5-Methyl-2-nitro-4-trifluoromethyl-phenylamine

Under argon atmosphere, a suspension of potassium tert-butanolate (71.6 g, 625 mmol) in DMSO (150 mL) was placed in a 1.5 L flask, fitted with a mechanical stirrer. Then diethyl malonate (97.9 mL, 625 mmol) was added drop wise at 20-30° C. under ice bath cooling. To the thick white suspension was the added solid commercially available 5-chloro-2-nitro-4-trifluoromethyl-phenylamine [CAS-No. 35375-74-7] (60.14 g, 250 mmol) in one portion, the mixture was diluted with DMSO (100 mL) and the red solution warmed up to 60° C. and stirred for 20 h at 60° C. The mixture was cooled to 23° C. and a solution of potassium hydroxide (85%, 65.24 g, 1 mol) in water (100 mL) was added drop wise. The mixture was then heated to 100° C. and stirred for further 4 h. The mixture was cooled to 23° C., diluted with water (ca. 1000 mL), acidified with 37% HCl 3 to pH 3, and extracted three times with tert-butyl methyl ether (TBME) The organic layers were washed with brine, dried over MgSO$_4$ and evaporated to give a brown solid, which was triturated with hot heptane, filtered off and washed with heptane to give the title compound as a brown solid (50.0 g, 91%), which was used without further purification. MS (ISN) 218.9 [M−H].

Step 2: 1-Bromo-5-methyl-2-nitro-4-trifluoromethyl-benzene

To a rapidly stirred mixture of tert-butyl nitrite (45.33 mL, 382 mmol) and copper(II) bromide (76.1 g, 341 mmol) in acetonitrile (450 mL) at 65° C. was added cautiously solid 5-methyl-2-nitro-4-trifluoromethyl-phenylamine from step 1 (50.0 g, 227 mmol). After the addition was complete, stirring was continued for further 1 h at 65° C. The mixture was cooled to 23° C. and poured into 1 N HCl (1000 mL), extracted twice with TBME, the organic layer was washed with brine, dried over MgSO$_4$. Removal of the solvent in vacuum left a brown oil, which was purified by silica gel column chromatography with heptane/ethyl acetate 9:1 to give the title compound as a yellow liquid (49.8 g, 77%). MS (EI) 283.0 [M] and 285.0 [M$^+$2].

Step 3: 5-Methyl-2-nitro-4-trifluoromethyl-benzonitrile

A mixture of 1-bromo-5-methyl-2-nitro-4-trifluoromethyl-benzene from step 2 (49.80 g, 175 mmol) and copper (I) cyanide (16.5 g, 184 mmol) in 1-methyl-2-pyrrolidone (NMP) (180 mL) was heated up to 150° C. and stirred for 30 min under nitrogen atmosphere.

The mixture was cooled to 23° C. and poured into 1 N HCl, extracted with TBME, washed with brine and dried over Na$_2$SO$_4$. Removal of the solvent in vacuum left a brown oil, which was purified by silica gel column chromatography with heptane/ethyl acetate 4:1→2:1 to give the title compound as a light yellow solid (35.48 g, 88%). MS (EI) 230.1 [M].

Step 4: 2-Amino-5-methyl-4-trifluoromethyl-benzonitrile

Iron powder (37.42 g, 670 mmol) was added in small portions to a stirred suspension of finely grinded 5-methyl-2-nitro-4-trifluoromethyl-benzonitrile from step 3 (34.58 g, 150 mmol) in methanol (75 mL) and 37% HCl (93 mL). The internal temperature was kept between 40 and 60° C. by external water bath cooling. The resulting brown solution was stirred for 1 h at 50° C., giving a green suspension. The mixture was poured into ice cold water (600 mL), the precipitated solid was filtered off and washed with water to give a green solid, which was dissolved in boiling ethanol (700 mL), activated carbon (ca. 10 g) was added and the mixture was refluxed for 1 h. The hot solution was filtered and the solvent was evaporated in vacuum to leave the title compound as a brown-yellow solid (23.55 g, 78%), which was used without further purification. MS (EI) 200.1 [M].

Step 5: 3-Methyl-4-trifluoromethyl-benzonitrile

To a solution of 2-amino-5-methyl-4-trifluoromethyl-benzonitrile from step 4 (23.34 g, 117 mmol) in dry THF (350 mL) was added isoamyl nitrite (34.3 mL, 257 mmol) and the mixture was refluxed for 20 h. Additional isoamyl nitrite (16.6 mL, 129 mmol) was added and the mixture was refluxed for further 20 h. The mixture was cooled to 23° C. and diluted with TBME, the organic layer was washed with 1 N HCl, sat. NaHCO$_3$-sol. and brine, dried over Na$_2$SO$_4$. Removal of the solvent in vacuum left a brown oil (25.82 g), which was purified by bulb to bulb distillation to give a yellow liquid (20.11 g), which was finally purified by distillation to give the title compound as a yellow liquid (17.10 g, 79%; bp 38-42° C. at 0.8 mbar). MS (EI) 185.1 [M].

Step 6: 3-Methyl-4-trifluoromethyl-benzoic acid

A mixture of 3-methyl-4-trifluoromethyl-benzonitrile from step 5 (16.25 g, 88 mmol) and 3 N NaOH (88 mL, 264 mmol) in dioxane (90 mL) was refluxed for 18 h. The mixture was cooled to 23° C., diluted with TBME, acidified with 1 N HCl to pH 1 and extracted twice with TBME. The combined organic layers were washed with brine, dried over MgSO$_4$. Removal of the solvent in vacuum left the title compound as an off white solid (14.46 g, 81%), %), which was used without further purification. MS (ISN) 203.1 [M−H].

Step 7: N-Methoxy-3,N-dimethyl-4-trifluoromethyl-benzamide

To a suspension of 3-methyl-4-trifluoromethyl-benzoic acid from step 6 (14.1 g, 69.1 mmol), N,O-dimethylhydroxylamine hydrochloride (10.78 g, 111 mmol), N-methylmorpholine (12.14 mL, 111 mmol) and 4-DMAP (844 mg, 691 mmol) in DCM (230 mL) at 0° C. were added 1-(3-dimethylaminopropyl)-3-ethylcarbodiimide hydrochloride (EDC) (15.98 g, 82.9 mmol) and DMF (85 mL). The mixture was warmed up to 23° C. and was stirred for 18 h under nitrogen atmosphere. The mixture was diluted with TBME, washed with water and twice brine, dried over Na$_2$SO$_4$. Removal of the solvent in vacuum left the title compound as a brown oil (16.92 g, 99%), which was used without further purification. MS (ISP) 248.0 [M+H].

Step 8: 1-(3-Methyl-4-trifluoromethyl-phenyl)-ethanone

To a solution of N-methoxy-3,N-dimethyl-4-trifluoromethyl-benzamide from step 7 (16.90 g, 68.36 mmol) in THF (280 mL) at −5° C. was added a 3 M methylmagnesium bromide solution in diethyl ether (45.6 mL, 136.7 mmol). The mixture was stirred at 0° C. for 1 h, then was warmed up to 23° C. and stirring was continued at 23° C. for further 1.5 h under nitrogen atmosphere. Then 1 N HCl (100 mL) was added drop wise to the mixture and stirring was continued for 30 min. The mixture was diluted with EtOAc and the aqueous layer was separated, the organic layer was washed with brine and dried over MgSO$_4$. Removal of the solvent in vacuum left the title compound as a light brown liquid (12.87 g, 93.1%), which was used without further purification. MS (EI) 202.1 [M].

Example A.5

3-Ethoxy-4-trifluoromethyl-acetophenone

The 1-(3-ethoxy-4-trifluoromethyl-phenyl)-ethanone was prepared by the following sequence:

Step 1: 5-Ethoxy-2-nitro-4-trifluoromethyl-phenylamine

To EtOH (500 mL) was added potassium metal (ca. 21 g, ca. 537 mmol) and the vigorous reaction had to be cooled with an ice bath. Stirring was continued until all potassium metal was dissolved. Solid commercially available 5-chloro-2-nitro-4-trifluoromethyl-phenylamine [CAS-No. 35375-74-7] (57.74 g, 240 mmol) was added in one portion and the resulting dark red mixture was stirred at 55-60° C. for 4 days. The warm reaction mixture was slowly poured into H$_2$O (ca. 2000 mL), adjusted pH with conc. HCl to pH 2, the yellow precipitate was filtered off, washed with H$_2$O and dried in air at 60° C. to give a yellow solid (57.81 g, 96%), which was used without further purification. MS (ISN) 249 [M−H].

Step 2: 1-Bromo-5-ethoxy-2-nitro-4-trifluoromethyl-benzene

Solid 5-ethoxy-2-nitro-4-trifluoromethyl-phenylamine from step 1 (57.81 g, 231 mmol) was added slowly over 15 min to a rapidly stirred mixture of tert-butyl nitrite (45.8 mL, 347 mmol) and anhydrous copper(II) bromide (77.4 g, 347 mmol) in acetonitrile (462 mL), which was heated to 65° C. in an oil bath. Stirring at 65° C. was continued for 30 min, the reaction mixture was cooled to 23° C., poured into 1 N HCl, saturated with solid NaCl, extracted with TBME, dried over MgSO$_4$. Removal of the solvent in vacuum left a dark brown oil (74.5 g). Silica gel column chromatography with heptane/EtOAc 4:1 gave the title compound as a yellow solid (63.03 g, 87%). MS (EI) 313.0 [M] and 315.0 [M+2].

Step 3: 5-Ethoxy-2-nitro-4-trifluoromethyl-benzonitrile

A mixture of 1-bromo-5-ethoxy-2-nitro-4-trifluoromethyl-benzene from step 2 (61.81 g, 197 mmol) and CuCN (18.51 g, 207 mmol) in NMP (197 mL) was heated to 150° C. for 30 min. Cooled to 23° C., poured into 1 N HCl, extracted with TBME, washed with brine, dried over Na$_2$SO$_4$. Removal of the solvent in vacuum left a brown oil. Silica gel column chromatography with heptane/EtOAc 4:1 gave the title compound as a yellow solid (46.73 g, 91%). MS (EI) 260.1 [M].

Step 4: 2-Amino-5-ethoxy-4-trifluoromethyl-benzonitrile

Iron powder (40.96 g, 733 mmol) was added in small portions over 5 min to a stirred suspension of finely grinded 5-ethoxy-2-nitro-4-trifluoromethyl-benzonitrile from step 3 (42.79 g, 164.5 mmol) in MeOH (85 mL) and conc. HCl (102 mL) with water bath cooling keeping the internal temperature at 40-50° C. The resulting mixture was stirred for further 1 h at ca. 50° C. and then poured into ice cold H$_2$O (700 mL). The precipitate was filtered, washed with water, dried, and dissolved in boiling EtOH (800 mL), activated carbon (ca. 10 g) was added, the mixture was refluxed for 45 min, the hot solution was filtered and evaporated to dryness to leave a yellow solid (31.81 g, 84%), which was used without further purification. MS (EI) 230.1 [M].

Step 5: 3-Ethoxy-4-trifluoromethyl-benzonitrile

To a solution of 2-amino-5-ethoxy-4-trifluoromethyl-benzonitrile from step 4 (31.62 g, 137.4 mmol) in dry THF (410 mL) was added isoamyl nitrite (40.4 mL, 302 mmol) and the mixture was refluxed for 16 h. The solvent was removed in vacuum to give an orange oil, which was dissolved in sat. NaHCO$_3$-sol., extracted three times with diethyl ether. The combined organic layers were washed with 1 N HCl and brine, dried over Na$_2$SO$_4$. Removal of the solvent in vacuum left an orange oil, which was purified by double Kugelrohr distillation (up to 160° C. bath temperature at 1.5 mbar) to give the title compound as a light yellow solid (25.06 g, 85%). MS (EI) 185.1 [M].

Step 6: 1-(3-Ethoxy-4-trifluoromethyl-phenyl)-ethanone

To a solution of 3-ethoxy-4-trifluoromethyl-benzonitrile from step 5 (5.00 g, 23.2 mmol), copper(I) bromide (100 mg, 0.7 mmol), tert.-butyldimethylchlorosilane (4.20 g, 27.9 mmol) in dry THF (30 mL) at −70° C. was drop wise added a 3 M methylmagnesium bromide solution in diethyl ether (13.2 mL, 39.6 mmol). The mixture was stirred at −70° C. for 10 min, then was warmed up to 0° C. and stirring was continued at 0° C. for further 2 h under nitrogen atmosphere. Poured the reaction mixture onto ice and sat. NH$_4$Cl-sol., extracted three times with diethyl ether, washed the combined organic layers with brine, dried over MgSO$_4$. Removal of the solvent in vacuum left a brown oil, which was purified by silica gel column chromatography with heptane/EtOAc 4:1 to give the title compound as a yellow liquid (1.84 g, 34%). MS (EI) 232 [M].

Example A.6

3-(2,2,2-Trifluoro-ethoxy)-4-trifluoromethyl-acetophenone

The 1-[3-(2,2,2-trifluoro-ethoxy)-4-trifluoromethyl-phenyl]-ethanone was prepared by the following sequence:

Step 1: 2-Nitro-5-(2,2,2-trifluoro-ethoxy)-4-trifluoromethyl-phenylamine

Commercially available 5-chloro-2-nitro-4-trifluoromethyl-phenylamine [CAS-No. 35375-74-7] (72.2 g, 300 mmol) was dissolved in DMSO (600 mL) and 2,2,2-trifluoroethanol (270 mL) were added at 23° C., the slightly exothermic reaction was cooled with a ice bath. KOH (85%, 99.0 g, 1500 mmol) were added slowly and the dark red reaction mixture was stirred at 23° C. for 4 days. Transferred into a 3 L flask and 1500 ml H$_2$O were added under ice bath cooling, acidified with 3 N HCl and stirred at 23° C. for 3 h, filtered off the yellow precipitate, washed with H$_2$O and dried in air at 60° C. to give the title compound as a yellow solid (89.47 g, 98%). MS (ISN) 303.1 [M−H].

Step 2: 1-Bromo-2-nitro-5-(2,2,2-trifluoro-ethoxy)-4-trifluoromethyl-benzene

Solid 2-nitro-5-(2,2,2-trifluoro-ethoxy)-4-trifluoromethyl-phenylamine from step 1 (24.28 g, 80 mmol) was added slowly over 15 min to a rapidly stirred mixture of tert-butyl nitrite (14.23 mL, 120 mmol) and anhydrous copper(II) bromide (26.75 g, 120 mmol) in acetonitrile (160 mL), which was heated to 65° C. in an oil bath. Stirring at 65° C. was continued for 2 h, the reaction mixture was cooled to 23° C., poured into 1 N HCl, saturated with solid NaCl, extracted with TBME, dried over $MgSO_4$. Removal of the solvent in vacuum left a dark brown oil (35.57 g). Silica gel column chromatography with heptane/EtOAc 4:1 gave the title compound as an orange solid (30.54 g, 104%), which was used without further purification. MS (EI) 367 [M] and 369 [M$^+$2].

Step 3: 2-Nitro-5-(2,2,2-trifluoro-ethoxy)-4-trifluoromethyl-benzonitrile

A mixture of 1-bromo-2-nitro-5-(2,2,2-trifluoro-ethoxy)-4-trifluoromethyl-benzene from step 2 (30.54 g, 83.0 mmol) and CuCN (7.80 g, 87.1 mmol) in NMP (83 mL) was heated to 150° C. for 30 min. Cooled to 23° C., poured into 1 N HCl, extracted with EtOAc, washed with brine, dried over $Na_2SO_4$. Removal of the solvent in vacuum left a dark brown oil (33.9 g). Silica gel column chromatography with heptane/EtOAc 9:1→4:1 gave the title compound as a yellow solid (22.05 g, 85%). MS (EI) 314 [M].

Step 4: 2-Amino-5-(2,2,2-trifluoro-ethoxy)-4-trifluoromethyl-benzonitrile

Iron powder (15.80 g, 283.0 mmol) was added in small portions over 5 min to a stirred suspension of finely grinded 2-nitro-5-(2,2,2-trifluoro-ethoxy)-4-trifluoromethyl-benzonitrile from step 3 (19.93 g, 63.4 mmol) in MeOH (32 mL) and conc. HCl (40 mL) with water bath cooling keeping the internal temperature at 25-35° C. The resulting mixture was stirred for further 1 h at ca. 30° C. and then poured into ice cold $H_2O$ (400 mL). The precipitate was filtered, washed with water, dried, and dissolved in boiling EtOH (400 mL), activated carbon (ca. 10 g) was added, the mixture was refluxed for 45 min, the hot solution was filtered and evaporated to dryness to leave a dark green solid (15.96 g, 84%), which was further purified by silica gel column chromatography with heptane/EtOAc 4:1 to give the title compound as a yellow solid (14.56 g, 81%). MS (ISN) 283 [M−H].

Step 5: 3-(2,2,2-Trifluoro-ethoxy)-4-trifluoromethyl-benzonitrile

To a solution of 2-amino-5-(2,2,2-trifluoro-ethoxy)-4-trifluoromethyl-benzonitrile from step 4 (14.47 g, 50.9 mmol) in dry THF (153 mL) was added isoamyl nitrite (15.0 mL, 112.0 mmol) and the mixture was refluxed for 20 h. The solvent was removed in vacuum to give an orange oil, which was dissolved in TBME, washed with 1 N HCl, sat. $NaHCO_3$-sol. and brine, dried over $Na_2SO_4$. Removal of the solvent in vacuum left a brown solid (15.05 g), which was purified by Kugelrohr distillation (up to 155° C. bath temperature at 1.2 mbar) to give the title compound as a light yellow solid (10.83 g, 79%). MS (EI) 269 [M].

Step 6: 3-(2,2,2-Trifluoro-ethoxy)-4-trifluoromethyl-benzoic acid

A mixture of 3-(2,2,2-trifluoro-ethoxy)-4-trifluoromethyl-benzonitrile from step 5 (8.75 g, 33 mmol) and 3 M NaOH (3.9 g, 98 mmol in 33 mL H2O) in dioxane (33 mL) was refluxed for 7.5 h. Poured onto ice, acidified with conc. HCl to pH 1, saturated with solid NaCl, extracted with TBME, dried over $MgSO_4$. Removal of the solvent in vacuum left the title compound as an off-white solid (9.22 g, 98%), %), which was used without further purification. MS (ISN) 286.9 [M−H].

Step 7: N-Methoxy-N-methyl-3-(2,2,2-trifluoro-ethoxy)-4-trifluoromethyl-benzamide To a mixture of 3-(2,2,2-trifluoro-ethoxy)-4-trifluoromethyl-benzoic acid from step 6 (9.22 g, 32 mmol), N,O-dimethylhydroxylamine hydrochloride (5.00 g, 51 mmol), N-methylmorpholine (5.62 mL, 51 mmol) and 4-DMAP (391 mg, 3.2 mmol) in DCM (100 mL) and DMF (20 mL) at 0° C. was added 1-(3-dimethylaminopropyl)-3-ethylcarbodiimide hydrochloride (EDC) (7.36 g, 38 mmol) and the mixture was stirred at 23° C. for 18 h. Poured onto ice cold 1 N HCl, extracted with TBME, washed with sat. $NaHCO_3$-sol. and brine, dried over $Na_2SO_4$. Removal of the solvent in vacuum left the title compound as a brown oil (10.555 g, 100%), %), which was used without further purification. MS (EI) 331.0 [M].

Step 8: 1-[3-(2,2,2-Trifluoro-ethoxy)-4-trifluoromethyl-phenyl]-ethanone

To a solution of N-methoxy-N-methyl-3-(2,2,2-trifluoro-ethoxy)-4-trifluoromethyl-benzamide from step 7 (10.467 g, 32 mmol) in THF (100 mL) at −5° C. was added methylmagnesium bromide (3 M in $Et_2O$, 21.1 mL, 64 mmol). The mixture was stirred at 0° C. for 15 min, then warmed up to 23° C., stirring was continued for further 1.5 h at 23° C. Cooled to 0° C., 1 N HCl (150 mL) was added dropwise, stirring was continued at 23° C. for 15 min, the mixture was diluted with TBME, the phases were separated, the organic layer was washed with water and brine, dried over MgSO4. Removal of the solvent in vacuum left a yellow solid (9.021 g, 100%), which was used without further purification. MS (EI) 286.1 [M].

Synthesis of Aniline Derivatives (Starting Material of Formula VII)

Example B.1

3-Amino-N-(2,2,2-trifluoro-ethyl)-benzenesulfonamide a) To a stirred solution of 2,2,2-trifluoroethylamine (1.17 ml, 15 mmol) in dioxane (37 ml) was added at room temperature 3-nitrobenzenesulfonyl chloride (3.0 g, 14 mmol) and triethylamine (2.06 ml, 15 mmol). The light yellow suspension was stirred at room temperature for 4 h, poured into water (100 ml) and extracted with dichloromethane (3×75 ml). The combined organic layers were washed with water (100 ml) and brine (70 ml), dried ($MgSO_4$) and evaporated. The crude product was further purified by column chromatography on silica gel (heptane/ethyl acetate 1:1) to yield 3-nitro-N-(2,2,2-trifluoro-ethyl)-benzenesulfonamide (3.18 g, 83%) as a light yellow solid. MS (ISP) 283.9 [(M−H)$^-$].

b) A mixture of 3-nitro-N-(2,2,2-trifluoro-ethyl)-benzenesulfonamide (3.12 g, 11 mmol), sodium dithionite (8.09 g, 40 mmol), water (21.5 ml) and 2 methoxyethanol (21.5 ml) was stirred at 100° C. for 2 h, additional water (18.5 ml) was added at 70° C. and subsequently HCl (37%, 18.5 ml) was added over a period of 10 min ($SO_2$ evolution). The reaction mixture was stirred at 70° C. for 20 min, poured into ice/water (50 ml) and sodium carbonate was added until the solution proofed to be basic. The solution was extracted with ethyl acetate (3×75 ml), the combined organic layers washed with brine (80 ml), dried (MgSO$_4$) and evaporated. The crude product was further purified by column chromatography on silica gel (heptane/ethyl acetate 1:1) to yield the title compound (2.05 g, 73%) as a white solid. MS (ISP) 252.9 [(M−H)$^-$]; m.p. 131° C.

Example B.2

3-Amino-N-cyclopropylmethyl-benzenesulfonamide a) To a stirred solution of cyclopropylmethylamine (1.28 ml, 15 mmol) in dioxane (37 ml) was added at room temperature 3-nitrobenzenesulfonyl chloride (3.0 g, 14 mmol) and triethylamine (2.06 ml, 15 mmol). The light yellow suspension was stirred at room temperature for 4 h, poured into water (100 ml) and extracted with dichloromethane (3×75 ml). The combined organic layers were washed with water (100 ml) and brine (70 ml), dried (MgSO$_4$) and evaporated. The crude product was further purified by column chromatography on silica gel (heptane/ethyl acetate 1:1) to yield 3-nitro-N-cyclopropylmethyl-benzenesulfonamide (3.08 g, 89%) as an off-white solid. MS (ISP) 254.9 [(M−H)$^-$]; m.p. 91° C.

b) Hydrogenation of a stirred solution of 3-nitro-N-cyclopropylmethyl-benzenesulfonamide (2.46 g, 10 mmol) in methanol (167 ml) on palladium/carbon (10%, 0.25 g) for 1 h at room temperature yielded after removal of the catalyst by filtration and evaporation the title compound as a light yellow liquid. MS (ISP) 225.1 [(M−H)$^-$].

Example B.3

3-Amino-N-pyridin-4-ylmethyl-benzenesulfonamide

A mixture of 3-nitro-N-(pyridin-4-ylmethyl)-benzenesulfonamide [CAS No. 332942-34-4, commercially available] (1.23 g, 4.2 mmol), sodium dithionite (3.09 g, 15.1 mmol), water (10 ml) and 2 methoxyethanol (10 ml) was stirred at 100° C. for 2 h, additional water (7 ml) was added at 70° C. and subsequently HCl (37%, 7 ml) was added over a period of 10 min (SO$_2$ evolution). The reaction mixture was stirred at 70° C. for 20 min, poured into ice/water (50 ml) and sodium carbonate was added until the solution proofed to be basic. The solution was extracted with ethyl acetate/MeOH 9:1 (3×75 ml), the combined organic layers washed with brine (80 ml), dried (MgSO$_4$) and evaporated. The crude product was further purified by column chromatography on silica gel (MeOH/ethyl acetate 1:9) to yield the title compound (0.8 g, 72%) as a light yellow solid. MS (ISP) 261.9 [(M−H)$^-$]; m.p. 139° C.

Example B.4

3-Amino-N-(2,2-dimethyl-propyl)-benzenesulfonamide a) To a stirred solution of neopentylamine (0.86 g ml, 9.93 mmol) in dioxane (25 ml) was added at room temperature 3-nitrobenzenesulfonyl chloride (2.0 g, 9.02 mmol) and triethylamine (1.38 ml, 9.93 mmol). The light yellow suspension was stirred at room temperature for 17 h, poured into water (100 ml) and extracted with dichloromethane (3×75 ml). The combined organic layers were washed with water (100 ml) and brine (70 ml), dried (MgSO$_4$) and evaporated. The crude product was further purified by crystallization from ethyl acetate/hexane to yield 3-nitro-N-(2,2-dimethyl-propyl)-benzenesulfonamide (2.14 g, 87%) as a white solid. MS (ISP) 271.1 [(M−H)$^-$]; mp 117° C.

b) Hydrogenation of a stirred solution of 3-nitro-N-(2,2-dimethyl-propyl)-benzenesulfonamide (2.04 g, 7.49 mmol) in methanol (130 ml) on palladium/carbon (10%, 0.20 g) for 1 h at room temperature yielded after removal of the catalyst by filtration, evaporation and crystallization from hexane the title compound as a white solid. MS (ISP) 243.2 [(M+H)$^+$]; mp 99° C.

Example B.5

3-Amino-N-pyridin-3-ylmethyl-benzenesulfonamide a) Hydrogenation of a stirred solution of 3-nitro-N-pyridin-3-ylmethyl-benzenesulfonamide [CAS-No. 436095-43-1; commercially available] (1.42 g, 4.84 mmol) in methanol (90 ml) and THF (50 ml) on palladium/carbon (10%, 0.14 g) for 2 h at room temperature yielded after removal of the catalyst by filtration, evaporation and crystallization from ethyl acetate/hexane the title compound (1.15 g, 90%) as a light yellow solid. MS (ISP) 264.1 [(M+H)$^+$]; mp 129° C.

Example B.6

3-Amino-N-pyridin-2-ylmethyl-benzenesulfonamide a) Hydrogenation of a stirred solution of 3-nitro-N-pyridin-2-ylmethyl-benzenesulfonamide [CAS-No. 309726-30-5; commercially available] (1.37 g, 4.67 mmol) in methanol (140 ml) on palladium/carbon (10%, 0.14 g) for 2 h at room temperature yielded after removal of the catalyst by filtration, evaporation and crystallization from ethyl acetate/hexane the title compound (1.16 g, 94%) as an off-white solid. MS (ISP) 262.0 [(M−H)$^-$]; mp 124° C.

Example B.7

3-Amino-N-(2-pyridin-4-yl-ethyl)-benzenesulfonamide a) To a stirred solution of 4-(2-aminoethyl)-pyridine (1.21 g, 9.93 mmol) in dioxane (25 ml) was added at room temperature 3-nitrobenzenesulfonyl chloride (2.0 g, 9.02 mmol) and triethylamine (1.38 ml, 9.93 mmol). The light yellow suspension was stirred at room temperature for 6 h, poured into water (100 ml) and extracted with dichloromethane (6×75 ml). The combined organic layers were washed with water (100 ml) and brine (70 ml), dried (MgSO$_4$) and evaporated. The crude product was further purified by crystallization from methanol/hexane to yield 3-nitro-N-(2-pyridine-4-yl-ethyl)-benzenesulfonamide (1.63 g, 59%) as an orange solid. MS (ISP) 306.1 [(M−H)$^-$]; mp 153° C.

b) Hydrogenation of a stirred solution of 3-nitro-N-(2-pyridine-4-yl-ethyl)-benzenesulfonamide (1.52 g, 4.95 mmol) in methanol (95 ml) and THF (55 ml) on palladium/carbon (10%, 0.15 g) for 4 h at room temperature yielded after removal of the catalyst by filtration, evaporation and crystallization from ethyl aceate/hexane the title compound as a light yellow solid. MS (ISP) 276.0 [(M−H)$^-$]; mp 138° C.

Example B.8

3-Amino-N-(2-hydroxy-1,1-dimethyl-ethyl)-benzenesulfonamide a) To a stirred solution of 2-amino-2-methyl-1-propanol (0.95 ml, 9.93 mmol) in dioxane (25 ml) was added at room temperature 3-nitrobenzenesulfonyl chloride (2.0 g, 9.02 mmol) and triethylamine (1.38 ml, 9.93 mmol). The light yellow suspension was stirred at room temperature for 6 h, poured into water (100 ml) and extracted with dichloromethane (3×75 ml). The combined organic layers were washed with water (100 ml) and brine (70 ml), dried (MgSO$_4$) and evaporated. The crude product was further purified by column chromatography on silica gel (heptane/ethyl acetate 1:1) to yield 3-nitro-N-cyclopropylmethyl-benzenesulfonamide (1.04 g, 42%) as a light yellow solid. MS (ISP) 273.2 [(M−H)$^-$].

b) Hydrogenation of a stirred solution of 3-nitro-N-cyclopropylmethyl-benzenesulfonamide (4.37 g, 15.9 mmol) in methanol (300 ml) on palladium/carbon (10%, 0.44 g) for 2 h at room temperature yielded after removal of the catalyst by filtration, evaporation and crystallization from ethyl aceate/hexane the title compound (3.79 g, 97%) as a white solid. MS (ISP) 243.2 [(M−H)$^-$]; mp 96° C.

Example B.9

3-Amino-N-(2-hydroxy-1-hydroxymethyl-1-methyl-ethyl)-benzenesulfonamide a) To a stirred solution of 2-amino-2-methyl-1,3-propanediol (1.04 ml, 9.93 mmol) in dioxane (25 ml) was added at room temperature 3-nitrobenzenesulfonyl chloride (2.0 g, 9.02 mmol) and triethylamine (1.38 ml, 9.93 mmol). The light yellow suspension was stirred at room temperature for 6 h, poured into water (100 ml) and extracted with dichloromethane (3×75 ml). The combined organic layers were washed with water (100 ml) and brine (70 ml), dried (MgSO$_4$) and evaporated. The crude product was further purified by column chromatography on silica gel (heptane/ethyl acetate 1:1) to yield N-(2-hydroxy-1-hydroxymethyl-1-methyl-ethyl)-3-nitro-benzenesulfonamide (0.65 g, 25%) as a white solid. MS (ISP) 289.1 [(M−H)$^-$]; mp 116° C.

b) Hydrogenation of a stirred solution of N-(2-hydroxy-1-hydroxymethyl-1-methyl-ethyl)-3-nitro-benzenesulfonamide (0.59 g, 2.03 mmol) in methanol (60 ml) on palladium/carbon (10%, 0.06 g) for 2.5 h at room temperature yielded after removal of the catalyst by filtration, evaporation and crystallization from ethyl acetate/hexane the title compound (0.22 g, 42%) as an orange solid. MS (ISP) 259.3 [(M−H)$^-$]; mp 129° C.

Example B.10

3-Amino-4-chloro-N-(2-hydroxy-1,1-dimethyl-ethyl)-benzenesulfonamide a) To a stirred solution of 2-amino-2-methyl-1-propanol (3.48 g, 39 mmol) in 1N NaOH (25 ml) was added at room temperature 4-chloro-3-nitrobenzenesulfonyl chloride (5.0 g, 19.5 mmol). The reaction mixture was stirred at room temperature for 16 h, poured into brine (50 ml) and extracted with ethyl acetate (3×70 ml). The combined organic layers were washed with brine (50 ml), dried (MgSO$_4$) and evaporated. The crude product was further purified by column chromatography on silica gel (heptane/ethyl acetate 1:4) and subsequent crystallization from ethyl acetate/heptane to yield 4-chloro-3-nitro-(2-hydroxy-1,1-dimethyl-ethyl)-benzenesulfonamide (0.93 g, 15%) as an off-white solid. MS (ISP) 307.0 [(M−H)$^-$]; mp 119° C.

b) A mixture of 4-chloro-3-nitro-(2-hydroxy-1,1-dimethyl-ethyl)-benzenesulfonamide (0.89 g, 2.89 mmol), sodium dithionite (2.13 g, 10 mmol), water (9 ml) and 2 methoxyethanol (9 ml) was stirred at 100° C. for 2 h, additional water (6 ml) was added at 70° C. and subsequently HCl (37%, 6 ml) was added over a period of 5 min (SO$_2$ evolution). The reaction mixture was stirred at 70° C. for 20 min, poured into ice/water (50 ml) and sodium carbonate was added until the solution proofed to be basic. The solution was extracted with ethyl acetate (3×70 ml), the combined organic layers washed with brine (50 ml), dried (Na$_2$SO$_4$) and evaporated. The crude product was further purified by crystallization from hexane/ethyl acetate to yield the title compound (0.65 g, 81%) as an off-white solid. MS (ISP) 277.1 [(M−H)$^-$]; mp 108° C.

Example B.11

3-Amino-N-(2-hydroxy-1,1-dimethyl-ethyl)-4-methyl-benzenesulfonamide a) To a stirred solution of 2-amino-2-methyl-1-propanol (3.78 g, 42 mmol) in 1N NaOH (25 ml) was added at room temperature 4-methyl-3-nitrobenzenesulfonyl chloride (5.0 g, 21 mmol). The reaction mixture was stirred at room temperature for 6 h, poured into brine (50 ml) and extracted with ethyl acetate (3×70 ml). The combined organic layers were washed with brine (50 ml), dried (MgSO$_4$) and evaporated. The crude product was further purified by column chromatography on silica gel (heptane/ethyl acetate 1:4) and subsequent crystallization from ethyl acetate/heptane to yield (2-hydroxy-1,1-dimethyl-ethyl)-4-methyl-3-nitro-benzenesulfonamide (1.5 g, 25%) as an off-white solid. MS (ISP) 287.0 [(M−H)$^-$]; mp 109° C.

b) Hydrogenation of a stirred solution of (2-hydroxy-1,1-dimethyl-ethyl)-4-methyl-3-nitro-benzenesulfonamide (1.46 g, 5.06 mmol) in methanol (50 ml) on palladium/carbon (10%, 0.15 g) for 1.5 h at room temperature yielded after removal of the catalyst by filtration, evaporation and crystallization from MeOH/diethyl ether/hexane the title compound (1.15 g, 88%) as an off-white solid. MS (ISP) 257.2 [(M−H)$^-$]; mp 133° C.

Example B.12

3-Amino-N-(2-dimethylamino-ethyl)-benzenesulfonamide

Hydrogenation of a stirred solution of N-(2-dimethylamino-ethyl)-3-nitro-benzenesulfonamide [CAS-No. 117082-97-0] (1.44 g, 5.27 mmol) in methanol (145 ml) on palladium/carbon (10%, 0.14 g) for 2.5 h at room temperature yielded after removal of the catalyst by filtration and evaporation the title compound (1.25 g, 98%) as a light yellow liquid, which was used without further purification. MS (ISP) 242.2 [(M−H)$^-$].

Example B.13

3-Amino-N-(1-hydroxymethyl-cyclopentyl)-benzenesulfonamide

A mixture of 3-nitro-benzenesulfonyl chloride (0.89 g, 4 mmol) and (1-amino-cyclopentyl)-methanol (0.46 g, 4 mmol) in dichloromethane (4 mL)/sat. sodium bicarbonate solution (4 mL) was stirred at 20° C. for 20 h. The mixture was diluted with dichloromethane (20 mL). The layers were separated and the organic layer was washed with water, dried (Na$_2$SO$_4$) and evaporated in vacuo. The solid residue was dissolved in ethanol (20 mL) and hydrogenated in the presence of 5% palladium-charcoal (0.2 g) to give the title compound (0.64 g, 59%). Off-white solid. MS (ISP) 271.4 [(M+H)$^+$]; mp 130-132° C.

Example B.14

(S)-[1-(3-Amino-benzenesulfonyl)-pyrrolidin-2-yl]-methanol

By subjecting 3-nitro-benzenesulfonyl chloride and L-prolinol in analogous manner to the procedure described in example B.13, the title compound was obtained. Pale-yellow oil. MS (ISP) 257.3 [(M+H)$^+$].

Synthesis of Intermediates Compounds: Pyrazolo-Pyrimidine Carboxylic Acids (Intermediates of Formula VI) from Acetophenones Some of the intermediates compounds, e.g. the pyrazolo-pyrimidine carboxylic acids derivatives which can be used according to the general procedures I and II are commercially available. However some of said intermediates have been prepared from acetophenones according to the procedures as outlined hereafter and unless otherwise specified, these compounds are novel. The person skilled in the art will be able to prepare other pyrazolo-pyrimidine carboxylic acids derivatives useful in the general procedures I and II taking into account the following examples of preparation:

Example C.1

7-Difluoromethyl-5-(4-trifluoromethyl-phenyl)-pyrazolo[1,5-a]pyrimidine-3-carboxylic acid a) To a stirred solution of ethyl difluoroacetate (5.0 ml, 21 mmol) in tert-butyl-methyl-ether (30 ml) was added at room temperature a 5.4M solution of sodium methanolate in methanol (4.65 ml, 25 mmol) followed by a solution of commercially available 4-trifluoromethyl-acetophenone (4.0 g, 21 mmol) in tert-butyl-methyl-ether (10 ml). The reaction mixture was stirred at room temperature for 19 h, poured into ice/water (50 ml), acidified with 2N HCl (40 ml) and extracted with diethyl ether (2×100 ml). The combined organic layers were washed with brine (2×50 ml), dried (MgSO$_4$) and evaporated to give crude 4,4-difluoro-1-(4-trifluoromethyl-phenyl)-butane-1,3-dione (5.87 g) as a yellow liquid, which was used without further purification.

b) A stirred mixture of commercially available 3-amino-4-ethoxycarbonyl-pyrazole (3.38 g, 22 mmol) and 4,4-difluoro-1-(4-trifluoromethyl-phenyl)-butane-1,3-dione (5.8 g, 22 mmol) in acetic acid (45 ml) was heated under reflux conditions for 1.5 h. The reaction mixture was evaporated and the crude product (yellow solid, 8.5 g, 22 mmol) was dissolved in a mixture of 2M KOH in methanol (176.5 ml, 0.35 mol) and water (85 ml). The reaction mixture was stirred at 60° C. for 1.5 h, poured into ice/water (200 ml), acidified with 3N sulfuric acid (pH=4) and stirred at room temperature for 30 min. The precipitate was collected by filtration and further purified by crystallization from diethylether/methanol to give the title compound (4.51 g, 57%) as an off-white solid. MS (ISP) 356.1 [(M−H)$^-$]; m.p. 261° C.

Example C.2

7-Trifluoromethyl-5-(4-trifluoromethyl-phenyl)-pyrazolo[1,5-a]pyrimidine-3-carboxylic acid The title compound was prepared from commercially available ethyl trifluoroacetate, commercially available 4-trifluoromethyl-acetophenone and commercially available 3-amino-4-ethoxycarbonyl-pyrazole according to the general procedure I. Light yellow solid. MS (EI) 374.9 [M]; mp 248° C.

Example C.3

5-(4-Chloro-phenyl)-7-difluoromethyl-pyrazolo[1,5-a]pyrimidine-3-carboxylic acid The title compound was prepared from commercially available ethyl difluoroacetate, commercially available 4-chloro-acetophenone and commercially available 3-amino-4-ethoxycarbonyl-pyrazole according to the general procedure I. Off-white solid. MS (ISP) 322.2 [(M−H)$^-$]; mp 232° C.

Example C.4

5-(4-Chloro-phenyl)-7-trifluoromethyl-pyrazolo[1,5-a]pyrimidine-3-carboxylic acid The title compound was prepared from commercially available ethyl trifluoroacetate, commercially available 4-chloro-acetophenone and commercially available 3-amino-4-ethoxycarbonyl-pyrazole according to the general procedure I. Off-white solid. MS (ISP) 340.0 [(M−H)$^-$]; mp 238° C.

Example C.5

7-Difluoromethyl-5-(3-methyl-4-trifluoromethyl-phenyl)-pyrazolo[1,5-a]pyrimidine-3-carboxylic acid The title compound was prepared from commercially available ethyl difluoroacetate, 3-methyl-4-trifluoro-acetophenone (example A.4) and commercially available 3-amino-4-ethoxycarbonyl-pyrazole according to the general procedure I. Off-white solid. MS (ISP) 370.1 [(M−H)$^-$]; mp 217° C.

Example C.6

5-(4-Chloro-3-methyl-phenyl)-7-trifluoromethyl-pyrazolo[1,5-a]pyrimidine-3-carboxylic acid The title compound was prepared from commercially available ethyl trifluoroacetate, commercially available 4-chloro-3-methyl-acetophenone and commercially available 3-amino-4-ethoxycarbonyl-pyrazole according to the general procedure I. Off-white solid. MS (ISP) 354.0 [(M−H)$^-$]; mp 243° C.

Example C.7

5-(3,4-Dichloro-phenyl)-7-difluoromethyl-pyrazolo[1,5-a]pyrimidine-3-carboxylic acid The title compound was prepared from commercially available ethyl difluoroacetate, commercially available 3,4-dichloro-acetophenone and commercially available 3-amino-4-ethoxycarbonyl-pyrazole according to the general procedure I. Off-white solid. MS (ISP) 356.0 [(M−H)$^-$]; mp 263° C.

Example C.8

5-(3-Methyl-4-trifluoromethyl-phenyl)-7-trifluoromethyl-pyrazolo[1,5-a]pyrimidine-3-carboxylic acid The title compound was prepared from commercially available ethyl trifluoroacetate, 3-methyl-4-trifluoro-acetophenone (example A.4) and commercially available 3-amino-4-ethoxycarbonyl-pyrazole according to the general procedure I. Off-white solid. MS (ISP) 388.1 [(M−H)$^-$]; mp 250° C.

Example C.9

5-(3,4-Dichloro-phenyl)-7-trifluoromethyl-pyrazolo[1,5-a]pyrimidine-3-carboxylic acid The title compound was prepared from commercially available ethyl trifluoroacetate, commercially available 3,4-dichloro-acetophenone and commercially available 3-amino-4-ethoxycarbonyl-pyrazole according to the general procedure I. Light yellow solid. MS (ISP) 374.1 [(M−H)$^-$]; mp 264° C.

Example C.10

5-[3-(2,2,2-Trifluoro-ethoxy)-4-trifluoromethyl-phenyl]-7-trifluoromethyl-pyrazolo[1,5-a]pyrimidine-3-carboxylic acid The title compound was prepared from commercially available ethyl trifluoroacetate, 3-(2,2,2-trifluoroethoxy)-4-trifluoro-acetophenone (Example A.6) and commercially available 3-amino-4-ethoxycarbonyl-pyrazole according to the general procedure I. Off-white solid. MS (ISP) 471.9 [(M−H)$^-$]; mp 264° C.

Example C.11

5-(3-Ethoxy-4-trifluoromethyl-phenyl)-7-trifluoromethyl-pyrazolo[1,5-a]pyrimidine-3-carboxylic acid The title compound was prepared from commercially available ethyl trifluoroacetate, 3-ethoxy-4-trifluoro-acetophenone (Example A.5) and commercially available 3-amino-4-ethoxycarbonyl-pyrazole according to the general procedure I. Off-white solid. MS (ISP) 418.0 [(M−H)$^-$]; mp 264° C.

Example C.12

7-Difluoromethyl-5-(3-ethoxy-4-trifluoromethyl-phenyl)-pyrazolo[1,5-a]pyrimidine-3-carboxylic acid The title compound was prepared from commercially available ethyl difluoroacetate, 3-ethoxy-4-trifluoro-acetophenone (Example A.5) and commercially available 3-amino-4-ethoxycarbonyl-pyrazole according to the general procedure I. Yellow solid. MS (ISP) 400.2 [(M−H)$^-$]; mp 247° C.

Example C.13

5-(4-Chloro-3-methyl-phenyl)-7-difluoromethyl-pyrazolo[1,5-a]pyrimidine-3-carboxylic acid The title compound was prepared from commercially available ethyl difluoroacetate, commercially available 4-chloro-3-methyl-acetophenone and commercially available 3-amino-4-ethoxycarbonyl-pyrazole according to the general procedure I. Light yellow solid. MS (ISP) 336.0 [(M−H)$^-$]; mp 238° C.

Example C.14

7-Difluoromethyl-5-[3-(2,2,2-trifluoro-ethoxy)-4-trifluoromethyl-phenyl]-pyrazolo[1,5-a]pyrimidine-3-carboxylic acid The title compound was prepared from commercially available ethyl difluoroacetate, 3-(2,2,2-trifluoroethoxy-4-trifluoro-acetophenone (Example A.6) and commercially available 3-amino-4-ethoxycarbonyl-pyrazole according to the general procedure I. Off-white solid. MS (ISP) 454.2 [(M−H)$^-$]; mp 261° C.

Example C.15

5-(3-Chloro-4-trifluoromethyl-phenyl)-7-difluoromethyl-pyrazolo[1,5-a]pyrimidine-3-carboxylic acid The title compound was prepared from commercially available ethyl difluoroacetate, 3-chloro-4-trifluoromethyl-acetophenone [CAS-No. 129322-80-1] and commercially available 3-amino-4-ethoxycarbonyl-pyrazole according to the general procedure I. Light red solid. MS (ISP) 390.2 [(M−H)$^-$]; mp 216° C.

Example C.16

7-Difluoromethyl-5-(3-fluoro-4-trifluoromethyl-phenyl)-pyrazolo[1,5-a]pyrimidine-3-carboxylic acid The title compound was prepared from commercially available ethyl difluoroacetate, commercially available 3-fluoro-4-trifluoromethyl-acetophenone and commercially available 3-amino-4-ethoxycarbonyl-pyrazole according to the general procedure I. Light brown solid. MS (ISP) 374.1 [(M−H)$^-$]; mp 233° C.

Example C.17

5-(3-Chloro-4-trifluoromethyl-phenyl)-7-trifluoromethyl-pyrazolo[1,5-a]pyrimidine-3-carboxylic acid The title compound was prepared from commercially available ethyl trifluoroacetate, 3-chloro-4-trifluoromethyl-acetophenone [CAS-No. 129322-80-1] and commercially available 3-amino-4-ethoxycarbonyl-pyrazole according to the general procedure I. Light yellow solid. MS (ISP) 408.0 [(M−H)⁻]; mp 244° C.

Example C.18

5-(3-Fluoro-4-trifluoromethyl-phenyl)-7-trifluoromethyl-pyrazolo[1,5-a]pyrimidine-3-carboxylic acid The title compound was prepared from commercially available ethyl trifluoroacetate, commercially available 3-fluoro-4-trifluoromethyl-acetophenone and commercially available 3-amino-4-ethoxycarbonyl-pyrazole according to the general procedure I. Light yellow solid. MS (ISP) 392.0 [(M−H)⁻]; mp 212° C.

Example C.19

5-(4-Trifluoromethoxy-phenyl)-7-trifluoromethyl-pyrazolo[1,5-a]pyrimidine-3-carboxylic acid The title compound was prepared from commercially available ethyl trifluoroacetate, commercially available 4-trifluoromethoxy-acetophenone and commercially available 3-amino-4-ethoxycarbonyl-pyrazole according to the general procedure I. White solid. MS (ISP) 390.0 [(M−H)⁻]; mp 225° C.

Example C.20

7-Difluoromethyl-5-(4-trifluoromethoxy-phenyl)-pyrazolo[1,5-a]pyrimidine-3-carboxylic acid The title compound was prepared from commercially available ethyl difluoroacetate, commercially available 4-trifluoromethoxy-acetophenone and commercially available 3-amino-4-ethoxycarbonyl-pyrazole according to the general procedure I. Off-white solid. MS (ISP) 372.1 [(M−H)⁻]; mp 231° C.

Example C.21

5-(3,4-Difluoro-phenyl)-7-trifluoromethyl-pyrazolo[1,5-a]pyrimidine-3-carboxylic acid The title compound was prepared from commercially available ethyl trifluoroacetate, commercially available 3,4-difluoro-acetophenone and commercially available 3-amino-4-ethoxycarbonyl-pyrazole according to the general procedure I. Light yellow solid. MS (ISP) 342.0 [(M−H)⁻]; mp 274° C.

Example C.22

5-(4-Chloro-phenyl)-pyrazolo[1,5-a]pyrimidine-3-carboxylic acid a) A mixture of ethyl 3-(4-chloro-phenyl)-3-oxo-propionate (18.1 g, 0.080 mol) and ethyl 5-amino-1H-pyrazole-4-carboxylate (13.7 g, 0.088 mol) was stirred at for 3 h 160° C. Ethyl acetate (40 mL) and hexane (40 mL) were successively added to the cooled mixture and stirring was continued at 0° C. for 0.5 h. The crystals were isolated by filtration and triturated for 1.2 h with 0.2 N HCl (80 mL). The solid was filtered off, washed with water and dried to give ethyl 5-(4-chloro-phenyl)-7-hydroxy-pyrazolo[1,5-a]pyrimidine-3-carboxylate (13.3 g, 52%). White solid. MS (ISN) 316.3 [(M−H)⁻]; mp 190-192° C.

b) A mixture of 5-(4-chloro-phenyl)-7-hydroxy-pyrazolo[1,5-a]pyrimidine-3-carboxylate (9.53 g, 0.03 mol), phosphorous oxychloride (11.0 mL, 0.12 mol), and N,N-dimethylaniline (1.3 mL, 0.01 mol) was stirred for 2 h at 100° C. The mixture was evaporated in vacuo and the residue was partitioned between water and dichloromethane. The organic phase was washed with water, dried (Na$_2$SO$_4$) and evaporated in vacuo. The remaining solid was crystallized from ethyl acetate/hexane to give 7-chloro-5-(4-chloro-phenyl)-pyrazolo[1,5-a]pyrimidine (6.80 g, 67%). Pale-yellow solid, MS (ISP) 336.0 [(M+H)⁺]; mp 133-135° C.

c) A mixture of 7-chloro-5-(4-chloro-phenyl)-pyrazolo[1,5-a]pyrimidine (0.34 g, 1.0 mmol), triethylamine (0.28 mL, 2.0 mmol), and 5% palladium-charcoal (0.03 g) in ethanol (60 mL) was stirred in an atmosphere of hydrogen for 12 min at 20° C. The catalyst was removed by filtration and the solution was evaporated. The residue was partitioned between ethyl acetate and water and the organic layer was dried (Na$_2$SO$_4$) and evaporated in vacuo. The residue was crystallized from ethyl acetate/cyclohexane to give ethyl 5-(4-chloro-phenyl)-pyrazolo[1,5-a]pyrimidine-3-carboxylate (0.18 g, 59%). Off-white solid; MS (ISP) 301.9 [(M+H)⁺].

d) A mixture of ethyl 5-(4-chloro-phenyl)-pyrazolo[1,5-a]pyrimidine-3-carboxylate (0.12 g, 0.4 mmol) and 0.5 N sodium hydroxide solution (4 mL) in methanol (4 mL) was heated to 70° C. for 2 h. The mixture was cooled, diluted with water (8 mL) and concentrated in vacuo. The aqueous solution was acidified to pH 2 by the addition of 3N HCl. The precipitate was isolated by filtration, washed with water, and dried to give 5-(4-chloro-phenyl)-pyrazolo[1,5-a]pyrimidine-3-carboxylic acid (0.11 g, 100%). Off-white solid. MS (ISN) 272.3 [(M−H)⁻]; mp 309-311° C.

Example C.23

5-(4-Trifluoromethyl-phenyl)-pyrazolo[1,5-a]pyrimidine-3-carboxylic acid

By subjecting ethyl 3-(4-trifluoro-phenyl)-3-oxo-propionate in analogous manner to the procedures described in example C.22, steps a-d, the title compound was obtained. White solid. NMR (DMSO-d6): d 7.97/8.52 (2 d, 2×2H), 7.98/9.41 (2 d, 2×1 H), 8.63 (s, 1H), 12.46 (s, 1H) ppm.

Example C.24

5-(4-Chloro-phenyl)-7-methyl-pyrazolo[1,5-a]pyrimidine-3-carboxylic acid

To a solution of 7-chloro-5-(4-chloro-phenyl)-pyrazolo[1,5-a]pyrimidine (0.34 g, 1.0 mmol) and tetrakis(triphenylphosphin)palladium (0.35 g, 0.3 mmol) in THF (15 mL) was added at 20° C. 2 M dimethylzinc/toluene solution (1.3 mL, 3.6 mmol) and the mixture was refluxed in an atmosphere of argon for 2 h. After the slow addition at 0° C. of sat. aqueous ammonium chloride solution (10 mL), the mixture was partitioned between ethyl acetate and water.

The organic layer was evaporated in vacuo and the residue chromatographed on silica gel using ethyl acetate/hexane (1:2 v/v) as eluent to give ethyl 5-(4-chloro-phenyl)-7-methyl-pyrazolo[1,5-a]pyrimidine-3-carboxylate (0.15 g) as a white solid. This material was saponified using in an analogous manner the procedure described in example C.22, step d), to give the title compound. White solid; MS (ISN) 286.0 [(M–H)⁻]; mp 233-235° C.

Example C.25

7-Methyl-5-(4-trifluoromethyl-phenyl)-pyrazolo[1,5-a]pyrimidine-3-carboxylic acid Subjecting ethyl 3-(4-trifluoro-phenyl)-3-oxo-propionate in analogous manner to the procedures described in Example C.22, steps a-b, and applying to the resulting product the procedure described in example C.24, afforded the title compound. White solid. MS (ISP) 320.3 [(M–H)⁻]; mp 244-245° C.

Example C.26

5-(4-Chloro-phenyl)-7-ethyl-pyrazolo[1,5-a]pyrimidine-3-carboxylic acid

To a solution of 7-chloro-5-(4-chloro-phenyl)-pyrazolo[1,5-a]pyrimidine (1.0 g, 3.0 mmol), tetrakis(triphenylphosphin)palladium (0.35 g, 0.3 mmol) in THF (5 mL) was added at 20° C. 0.4 M ethylzinc chloride/THF solution (30 mL, 12 mmol; freshly prepared by stirring a mixture of 6 mL of 2 M ethylmagnesium chloride/THF and 24 mL of 0.5 M zinc chloride/THF for 1 h at 0° C. followed by 1 h at 20° C.) and the mixture was refluxed in an atmosphere of argon for 2 h. After the slow addition at 0° C. of sat. aqueous ammonium chloride solution (8 mL), the mixture was partitioned between ethyl acetate and 10% sodium chloride solution. The organic layer was evaporated in vacuo and the residue chromatographed on silica gel using ethyl acetate/cyclohexane (1:4 v/v) as eluent to give ethyl 5-(4-chloro-phenyl)-7-ethyl-pyrazolo[1,5-a]pyrimidine-3-carboxylic acid (0.53 g, 54%). This material was saponified using in an analogous manner the procedure described in example C.22, step d), to give the title compound. White solid; MS (ISN) 330.1 [(M–H)⁻]; mp 227° C.

Example C.27

5-(4-Chloro-phenyl)-7-propyl-pyrazolo[1,5-a]pyrimidine-3-carboxylic acid

Subjecting ethyl 7-chloro-5-(4-chloro-phenyl)-pyrazolo[1,5-a]pyrimidine in analogous manner to the procedure described in Example C.26, but replacing the ethylzinc chloride/THF solution by a 0.4 M propylzinc chloride/THF solution (freshly prepared from ethylmagnesium chloride and zinc chloride), the title compound was obtained. White solid. MS (ISN) 314.1 [(M–H)⁻]; mp 208° C.

Example C.28

5-(4-Chloro-phenyl)-7-cyclopropyl-pyrazolo[1,5-a]pyrimidine-3-carboxylic acid

To a solution of 7-chloro-5-(4-chloro-phenyl)-pyrazolo[1,5-a]pyrimidine (4.0 g, 12.0 mmol), tetrakis(triphenylphosphin)palladium (1.15 g, 1.0 mmol) in THF (20 mL) was added at 20° C. 0.25 M cyclopropylzinc chloride/THF suspension (ca. 192 mL, 48 mol; freshly prepared by stirring a mixture of 96 mL of 0.5 M cyclopropylmagnesium bromide/THF and 96 mL of 0.5 M zinc chloride/THF (96 mL) for 1 h at 0° C. followed by 1 h at 20° C.) and the mixture was refluxed in an atmosphere of argon for 2.5 h. After the slow addition at 0° C. of sat. aqueous ammonium chloride solution (30 mL), the mixture was partitioned between ethyl acetate and 10% sodium chloride solution. The organic layer was evaporated in vacuo and the residue chromatographed on silica gel using ethyl acetate/cyclohexane (1:4 v/v) as eluent to give after crystallization from ethyl acetate ethyl 5-(4-chloro-phenyl)-7-cyclopropyl-pyrazolo[1,5-a]pyrimidine-3-carboxylic acid (2.54 g, 62%) as an off-white solid, mp 141-143° C. This material was saponified using in an analogous manner the procedure described in example C.22, step d), to give the title compound. Off-white solid, MS (ISN) 312.3 [(M–H)⁻]; mp 242-243° C.

Example C.29

7-Cyclopropyl-5-(4-trifluoromethyl-phenyl)-pyrazolo[1,5-a]pyrimidine-3-carboxylic acid By subjecting ethyl 3-(4-trifluoro-phenyl)-3-oxo-propionate in analogous manner to the procedures described in example C.22, steps a-b, and applying to the resulting product the procedure described in example C.28, the title compound was obtained. Off-white solid. MS (ISP) 346.3 [(M–H)⁻]; mp 233-235° C.

Synthesis of Compounds According to the Invention

The following examples illustrate the invention without limiting its scope to these sole examples.

Example 1

7-Trifluoromethyl-5-(4-trifluoromethyl-phenyl)-pyrazolo[1,5-a]pyrimidine-3-carboxylic acid[3-(morpholine-4-sulfonyl)-phenyl]-amide The title compound was prepared from 7-trifluoromethyl-5-(4-trifluoromethyl-phenyl)-pyrazolo[1,5-a]pyrimidine-3-carboxylic acid (example C.1) and 3-(morpholine-4-sulfonyl)-phenylamine [CAS 22184-97-0; commercially available] according to general procedure II. Yellow solid. MS (ISP) 600.3 [(M+H)⁺]; mp 233° C.

Example 2

5-(4-Methoxy-phenyl)-7-trifluoromethyl-pyrazolo[1,5-a]pyrimidine-3-carboxylic acid[3-(morpholine-4-sulfonyl)-phenyl]-amide The title compound was prepared from 5-(4-methoxy-phenyl)-7-trifluoromethyl-pyrazolo[1,5-a]pyrimidine-3-carboxylic acid [CAS 333761-72-1; commercially available] and 3-(morpholine-4-sulfonyl)-phenylamine [CAS 22184-97-0; commercially available] according to general procedure II. Yellow solid. MS (ISP) 562.4 [(M+H)⁺]; mp 203° C.

Example 3

7-Difluoromethyl-5-(4-trifluoromethyl-phenyl)-pyrazolo[1,5-a]pyrimidine-3-carboxylic acid[3-(morpholine-4-sulfonyl)-phenyl]-amide The title compound was prepared from 7-difluoromethyl-5-(4-trifluoromethyl-phenyl)-pyrazolo[1,5-a]pyrimidine-3-carboxylic acid (example C.1) and 3-(morpholine-4-sulfonyl)-phenylamine [CAS 22184-97-0; commercially available] according to general procedure II as follows: to a stirred solution of a pyrazolo[1,5-a]pyrimidine-3-carboxylic acid (1.0 mmol) in THF (4 ml) was added at room temperature DMF (2 drops), the solution was cooled to 0° C. and oxalylchloride (1.5 mmol) was added. The reaction mixture was stirred at room temperature for 3 h and evaporated to dryness. The precipitate was dissolved in pyridine (6 ml) and, while stirring at room temperature, 4-dimethylaminopyridine (1 mmol) and an aniline derivative (1 mmol) was added. The reaction mixture was allowed to stir at room temperature for 16 h, evaporated to dryness and the crude product purified by flash chromatography on silica gel (20 g, dichloromethane/methanol) to yield the product as a light yellow solid, which was further purified by crystallization from methanol/hexane. MS (ISP) 580.1 [(M−H)−]; mp 221° C.

Example 4

7-Trifluoromethyl-5-(4-trifluoromethyl-phenyl)-pyrazolo[1,5-a]pyrimidine-3-carboxylic acid[3-(pyrrolidine-1-sulfonyl)-phenyl]-amide The title compound was prepared from 7-trifluoromethyl-5-(4-trifluoromethyl-phenyl)-pyrazolo[1,5-a]pyrimidine-3-carboxylic acid (example C.2) and 3-(pyrrolidine-4-sulfonyl)-phenylamine [CAS 91619-38-4; commercially available] according to general procedure II. Yellow solid. MS (ISP) 584.2 [(M+H)+]; mp 241° C.

Example 5

5-(4-Chloro-phenyl)-7-trifluoromethyl-pyrazolo[1,5-a]pyrimidine-3-carboxylic acid[3-(pyrrolidine-1-sulfonyl)-phenyl]-amide The title compound was prepared from 5-(4-chloro-phenyl)-7-trifluoromethyl-pyrazolo[1,5-a]pyrimidine-3-carboxylic acid (example C.3) and 3-(pyrrolidine-4-sulfonyl)-phenylamine [CAS 91619-38-4; commercially available] according to general procedure II. Yellow solid. MS (ISP) 550.2 [(M+H)+]; mp 252° C.

Example 6

5-(4-Chloro-phenyl)-7-difluoromethyl-pyrazolo[1,5-a]pyrimidine-3-carboxylic acid[3-(pyrrolidine-1-sulfonyl)-phenyl]-amide The title compound was prepared from 5-(4-chloro-phenyl)-7-difluoromethyl-pyrazolo[1,5-a]pyrimidine-3-carboxylic acid (example C.3) and 3-(pyrrolidine-4-sulfonyl)-phenylamine [CAS 91619-38-4; commercially available] according to general procedure II. Yellow solid. MS (ISP) 532.2 [(M+H)+]; mp 227° C.

Example 7

5-(4-Chloro-phenyl)-7-difluoromethyl-pyrazolo[1,5-a]pyrimidine-3-carboxylic acid[3-(4-methyl-piperazine-1-sulfonyl)-phenyl]-amide The title compound was prepared from 5-(4-chloro-phenyl)-7-difluoromethyl-pyrazolo[1,5-a]pyrimidine-3-carboxylic acid (example C.3) and 3-(4-methyl-piperazine-1-sulfonyl)-phenylamine [CAS 436095-35-1] according to general procedure II. Yellow solid. MS (ISP) 561.5 [(M+H)+]; mp 147° C.

Example 8

5-(4-Chloro-phenyl)-7-difluoromethyl-pyrazolo[1,5-a]pyrimidine-3-carboxylic acid[3-(morpholine-4-sulfonyl)-phenyl]-amide The title compound was prepared from 5-(4-chloro-phenyl)-7-difluoromethyl-pyrazolo[1,5-a]pyrimidine-3-carboxylic acid (example C.3) and 3-(morpholine-4-sulfonyl)-phenylamine [CAS 22184-97-0; commercially available] according to general procedure II. Yellow solid. MS (ISP) 548.3 [(M+H)+]; mp 253° C.

Example 9

5-(4-Chloro-phenyl)-7-trifluoromethyl-pyrazolo[1,5-a]pyrimidine-3-carboxylic acid[3-(4-methyl-piperazine-1-sulfonyl)-phenyl]-amide The title compound was prepared from 5-(4-chloro-phenyl)-7-tifluoromethyl-pyrazolo[1,5-a]pyrimidine-3-carboxylic acid (example C.4) and 3-(4-methyl-piperazine-1-sulfonyl)-phenylamine [CAS 436095-35-1] according to general procedure II. Yellow solid. MS (ISP) 579.2 [(M+H)+]; mp 195° C.

Example 10

5-(4-Chloro-phenyl)-7-trifluoromethyl-pyrazolo[1,5-a]pyrimidine-3-carboxylic acid[3-(morpholine-4-sulfonyl)-phenyl]-amide The title compound was prepared from 5-(4-chloro-phenyl)-7-trifluoromethyl-pyrazolo[1,5-a]pyrimidine-3-carboxylic acid (example C.4) and 3-(morpholine-4-sulfonyl)-phenylamine [CAS 22184-97-0; commercially available] according to general procedure II. Yellow solid. MS (ISP) 566.1 [(M+H)+]; mp 144° C.

Example 11

7-Difluoromethyl-5-(3-methyl-4-trifluoromethyl-phenyl)-pyrazolo[1,5-a]pyrimidine-3-carboxylic acid[3-(pyrrolidine-1-sulfonyl)-phenyl]-amide The title compound was prepared from 7-difluoromethyl-5-(3-methyl-4-trifluoromethyl-phenyl)-pyrazolo[1,5-a]pyrimidine-3-carboxylic acid (example C.5) and 3-(pyrrolidine-4-sulfonyl)-phenylamine [CAS 91619-38-4; commercially available] according to general procedure II. Yellow solid. MS (ISP) 580.0 [(M+H)+]; mp 226° C.

Example 12

7-Difluoromethyl-5-(3-methyl-4-trifluoromethyl-phenyl)-pyrazolo[1,5-a]pyrimidine-3-carboxylic acid[3-(morpholine-4-sulfonyl)-phenyl]-amide The title compound was prepared from 7-difluoromethyl-5-(3-methyl-4-trifluoromethyl-phenyl)-pyrazolo[1,5-a]pyrimidine-3-carboxylic acid (example C.5) and 3-(morpholine-4-sulfonyl)-phenylamine [CAS 22184-97-0; commercially available] according to general procedure II. Yellow solid. MS (ISP) 595.2 [(M+H)$^+$]; mp 261° C.

Example 13

7-Trifluoromethyl-5-(4-trifluoromethyl-phenyl)-pyrazolo[1,5-a]pyrimidine-3-carboxylic acid(3-sulfamoyl-phenyl)-amide The title compound was prepared from 7-trifluoromethyl-5-(4-trifluoromethyl-phenyl)-pyrazolo[1,5-a]pyrimidine-3-carboxylic acid (example C.2) and 3-sulfamoyl-phenylamine [commercially available] according to general procedure II. Yellow solid. MS (ISP) 529.0 [(M+H)$^+$]; mp 155° C.

Example 14

5-(4-Chloro-3-methyl-phenyl)-7-trifluoromethyl-pyrazolo[1,5-a]pyrimidine-3-carboxylic acid[3-(pyrrolidine-1-sulfonyl)-phenyl]-amide The title compound was prepared from 5-(4-chloro-3-methyl-phenyl)-7-trifluoromethyl-pyrazolo[1,5-a]pyrimidine-3-carboxylic acid (example C.4) and 3-(pyrrolidine-4-sulfonyl)-phenylamine [CAS 91619-38-4; commercially available] according to general procedure II. Yellow solid. MS (ISP) 564.3 [(M+H)$^+$]; mp 230° C.

Example 15

5-(4-Chloro-3-methyl-phenyl)-7-trifluoromethyl-pyrazolo[1,5-a]pyrimidine-3-carboxylic acid[3-(morpholine-4-sulfonyl)-phenyl]-amide The title compound was prepared from 5-(4-chloro-3-methyl-phenyl)-7-trifluoromethyl-pyrazolo[1,5-a]pyrimidine-3-carboxylic acid (example C.6) and 3-(morpholine-4-sulfonyl)-phenylamine [CAS 22184-97-0; commercially available] according to general procedure II. Yellow solid. MS (ISP) 580.2 [(M+H)$^+$]; mp 251° C.

Example 16

5-(3,4-Dichloro-phenyl)-7-difluoromethyl-pyrazolo[1,5-a]pyrimidine-3-carboxylic acid[3-(pyrrolidine-1-sulfonyl)-phenyl]-amide The title compound was prepared from 5-(3,4-dichloro-phenyl)-7-difluoromethyl-pyrazolo[1,5-a]pyrimidine-3-carboxylic acid (example C.7) and 3-(pyrrolidine-4-sulfonyl)-phenylamine [CAS 91619-38-4; commercially available] according to general procedure II. Yellow solid. MS (ISP) 567.2 [(M+H)$^+$]; mp 245° C.

Example 17

5-(3,4-Dichloro-phenyl)-7-difluoromethyl-pyrazolo[1,5-a]pyrimidine-3-carboxylic acid[3-(morpholine-4-sulfonyl)-phenyl]-amide The title compound was prepared from 5-(3,4-dichloro-phenyl)-7-difluoromethyl-pyrazolo[1,5-a]pyrimidine-3-carboxylic acid (example C.7) and 3-(morpholine-4-sulfonyl)-phenylamine [CAS 22184-97-0; commercially available] according to general procedure II. Yellow solid. MS (ISP) 582.1 [(M+H)$^+$]; mp 231° C.

Example 18

7-Trifluoromethyl-5-(4-trifluoromethyl-phenyl)-pyrazolo[1,5-a]pyrimidine-3-carboxylic acid(3-ethylsulfamoyl-phenyl)-amide The title compound was prepared from 7-trifluoromethyl-5-(4-trifluoromethyl-phenyl)-pyrazolo[1,5-a]pyrimidine-3-carboxylic acid (example C.2) and 3-amino-N-ethyl-benzenesulfonamide [CAS 56445-08-0] according to general procedure II. Yellow solid. MS (ISP) 556.0 [(M+H)$^+$]; mp 207° C.

Example 19

5-(3,4-Dichloro-phenyl)-7-trifluoromethyl-pyrazolo[1,5-a]pyrimidine-3-carboxylic acid[3-(pyrrolidine-1-sulfonyl)-phenyl]-amide The title compound was prepared from 5-(3,4-dichloro-phenyl)-7-trifluoromethyl-pyrazolo[1,5-a]pyrimidine-3-carboxylic acid (example C.9) and 3-(pyrrolidine-4-sulfonyl)-phenylamine [CAS 91619-38-4; commercially available] according to general procedure II. Yellow solid. MS (ISP) 584.1 [(M+H)$^+$]; mp 280° C.

Example 20

5-(3,4-Dichloro-phenyl)-7-trifluoromethyl-pyrazolo[1,5-a]pyrimidine-3-carboxylic acid[3-(morpholine-4-sulfonyl)-phenyl]-amide The title compound was prepared from 5-(3,4-dichloro-phenyl)-7-trifluoromethyl-pyrazolo[1,5-a]pyrimidine-3-carboxylic acid (example C.9) and 3-(morpholine-4-sulfonyl)-phenylamine [CAS 22184-97-0; commercially available] according to general procedure II. Yellow solid. MS (ISP) 601.3 [(M+H)$^+$]; mp 239° C.

Example 21

7-Trifluoromethyl-5-(4-trifluoromethyl-phenyl)-pyrazolo[1,5-a]pyrimidine-3-carboxylic acid(3-dimethylsulfamoyl-phenyl)-amide The title compound was prepared from 7-trifluoromethyl-5-(4-trifluoromethyl-phenyl)-pyrazolo[1,5-a]pyrimidine-3-carboxylic acid (example C.2) and 3-amino-N,N-dimethyl-benzenesulfonamide [CAS 6274-18-6; commercially available] according to general procedure II. Yellow solid. MS (ISP) 558.3 [(M+H)$^+$]; mp 210° C.

Example 22

5-(4-Chloro-3-methyl-phenyl)-7-trifluoromethyl-pyrazolo[1,5-a]pyrimidine-3-carboxylic acid[3-(4-methyl-piperazine-1-sulfonyl)-phenyl]-amide The title compound was prepared from 5-(4-chloro-3-methyl-phenyl)-7-tifluoromethyl-pyrazolo[1,5-a]pyrimidine-3-carboxylic acid (example C.6) and 3-(4-methyl-piperazine-1-sulfonyl)-phenylamine [CAS 436095-35-1] according to general procedure II. Yellow solid. MS (ISP) 593.3 [(M+H)$^+$]; mp 143° C.

Example 23

5-(3,4-Dichloro-phenyl)-7-difluoromethyl-pyrazolo[1,5-a]pyrimidine-3-carboxylic acid[3-(4-methyl-piperazine-1-sulfonyl)-phenyl]-amide The title compound was prepared from 5-(3,4-dichloro-phenyl)-7-difluoromethyl-pyrazolo[1,5-a]pyrimidine-3-carboxylic acid (example C.7) and 3-(4-methyl-piperazine-1-sulfonyl)-phenylamine [CAS 436095-35-1] according to general procedure II. Yellow solid. MS (ISP) 595.3 [(M+H)$^+$]; mp 229° C.

Example 24

5-(3,4-Dichloro-phenyl)-7-trifluoromethyl-pyrazolo[1,5-a]pyrimidine-3-carboxylic acid[3-(4-methyl-piperazine-1-sulfonyl)-phenyl]-amide The title compound was prepared from 5-(3,4-dichloro-phenyl)-7-trifluoromethyl-pyrazolo[1,5-a]pyrimidine-3-carboxylic acid (example C.9) and 3-(4-methyl-piperazine-1-sulfonyl)-phenylamine [CAS 436095-35-1] according to general procedure II. Yellow solid. MS (ISP) 613.3 [(M+H)$^+$]; mp 181° C.

Example 25

7-Difluoromethyl-5-(4-trifluoromethyl-phenyl)-pyrazolo[1,5-a]pyrimidine-3-carboxylic acid(3-ethylsulfamoyl-phenyl)-amide The title compound was prepared from 7-difluoromethyl-5-(4-trifluoromethyl-phenyl)-pyrazolo[1,5-a]pyrimidine-3-carboxylic acid (example C.1) and 3-amino-N-ethyl-benzenesulfonamide [CAS 56445-08-0] according to general procedure II. Light yellow solid. MS (ISP) 538.1 [(M−H)$^-$]; mp 259° C.

Example 26

7-Difluoromethyl-5-(4-trifluoromethyl-phenyl)-pyrazolo[1,5-a]pyrimidine-3-carboxylic acid(3-dimethylsulfamoyl-phenyl)-amide The title compound was prepared from 7-difluoromethyl-5-(4-trifluoromethyl-phenyl)-pyrazolo[1,5-a]pyrimidine-3-carboxylic acid (example C.1) and 3-amino-N,N-dimethyl-benzenesulfonamide [CAS 6274-18-6; commercially available] according to general procedure II. Light yellow solid. MS (ISP) 540.4 [(M+H)$^+$]; mp 197° C.

Example 27

5-(3-Methyl-4-trifluoromethyl-phenyl)-7-trifluoromethyl-pyrazolo[1,5-a]pyrimidine-3-carboxylic acid [3-(morpholine-4-sulfonyl)-phenyl]-amide The title compound was prepared from 5-(3-methyl-4-trifluoromethyl-phenyl)-7-trifluoromethyl-pyrazolo[1,5-a]pyrimidine-3-carboxylic acid (example C.8) and 3-(morpholine-4-sulfonyl)-phenylamine [CAS 22184-97-0; commercially available] according to general procedure II. Yellow solid. MS (ISP) 614.4 [(M+H)$^+$]; mp 272° C.

Example 28

5-(3-Methyl-4-trifluoromethyl-phenyl)-7-trifluoromethyl-pyrazolo[1,5-a]pyrimidine-3-carboxylic acid [3-(4-methyl-piperazine-1-sulfonyl)-phenyl]-amide The title compound was prepared from 5-(3-methyl-4-trifluoromethyl-phenyl)-7-trifluoromethyl-pyrazolo[1,5-a]pyrimidine-3-carboxylic acid (example C.8) and 3-(4-methyl-piperazine-1-sulfonyl)-phenylamine [CAS 436095-35-1] according to general procedure II. Yellow solid. MS (ISP) 627.4 [(M+H)$^+$]; mp 199° C.

Example 29

7-Difluoromethyl-5-(3-methyl-4-trifluoromethyl-phenyl)-pyrazolo[1,5-a]pyrimidine-3-carboxylic acid[3-(4-methyl-piperazine-1-sulfonyl)-phenyl]-amide The title compound was prepared from 7-difluoromethyl-5-(3-methyl-4-trifluoromethyl-phenyl)-pyrazolo[1,5-a]pyrimidine-3-carboxylic acid (example C.5) and 3-(4-methyl-piperazine-1-sulfonyl)-phenylamine [CAS 436095-35-1] according to general procedure II. Yellow solid. MS (ISP) 609.3 [(M+H)$^+$]; mp 198° C.

Example 30

5-(3-Ethoxy-4-trifluoromethyl-phenyl)-7-trifluoromethyl-pyrazolo[1,5-a]pyrimidine-3-carboxylic acid [3-(morpholine-4-sulfonyl)-phenyl]-amide The title compound was prepared from 5-(3-ethoxy-4-trifluoromethyl-phenyl)-7-trifluoromethyl-pyrazolo[1,5-a]pyrimidine-3-carboxylic acid (example C.10) and 3-(morpholine-4-sulfonyl)-phenylamine [CAS 22184-97-0; commercially available] according to general procedure II. Yellow solid. MS (ISP) 642.2 [(M−H)$^-$]; mp 235° C.

Example 31

7-Difluoromethyl-5-(3-ethoxy-4-trifluoromethyl-phenyl)-pyrazolo[1,5-a]pyrimidine-3-carboxylic acid[3-(morpholine-4-sulfonyl)-phenyl]-amide The title compound was prepared from 7-difluoromethyl-5-(3-ethoxy-4-trifluoromethyl-phenyl)-pyrazolo[1,5-a]pyrimidine-3-carboxylic acid (example C.12) and 3-(morpholine-4-sulfonyl)-phenylamine [CAS 22184-97-0; commercially available] according to general procedure II. Light yellow solid. MS (ISP) 624.3 [(M−H)$^-$]; mp 231° C.

Example 32

5-(3-Ethoxy-4-trifluoromethyl-phenyl)-7-trifluoromethyl-pyrazolo[1,5-a]pyrimidine-3-carboxylic acid (3-sulfamoyl-phenyl)-amide The title compound was prepared from 5-(3-ethoxy-4-trifluoromethyl-phenyl)-7-trifluoromethyl-pyrazolo[1,5-a]pyrimidine-3-carboxylic acid (example C.11) and 3-sulfamoyl-phenylamine [commercially available] according to general procedure II. Yellow solid. MS (ISP) 572.1 [(M−H)$^-$]; mp 253° C.

Example 33

7-Difluoromethyl-5-(3-ethoxy-4-trifluoromethyl-phenyl)-pyrazolo[1,5-a]pyrimidine-3-carboxylic acid(3-sulfamoyl-phenyl)-amide The title compound was prepared from 7-difluoromethyl-5-(3-ethoxy-4-trifluoromethyl-phenyl)-pyrazolo[1,5-a]pyrimidine-3-carboxylic acid (example C.12) and 3-sulfamoyl-phenylamine [commercially available] according to general procedure II. Light yellow solid. MS (ISP) 554.0 [(M−H)$^-$]; mp 254° C.

Example 34

5-(3-Ethoxy-4-trifluoromethyl-phenyl)-7-trifluoromethyl-pyrazolo[1,5-a]pyrimidine-3-carboxylic acid (3-ethylsulfamoyl-phenyl)-amide The title compound was prepared from 5-(3-ethoxy-4-trifluoromethyl-phenyl)-7-trifluoromethyl-pyrazolo[1,5-a]pyrimidine-3-carboxylic acid (example C.11) and 3-amino-N-ethyl-benzenesulfonamide [CAS 56445-08-0] according to general procedure II. Yellow solid. MS (ISP) 600.0 [(M−H)$^-$]; mp 226° C.

Example 35

7-Difluoromethyl-5-(3-ethoxy-4-trifluoromethyl-phenyl)-pyrazolo[1,5-a]pyrimidine-3-carboxylic acid(3-ethylsulfamoyl-phenyl)-amide The title compound was prepared from 7-difluoromethyl-5-(3-ethoxy-4-trifluoromethyl-phenyl)-pyrazolo[1,5-a]pyrimidine-3-carboxylic acid (example C.12) and 3-amino-N-ethyl-benzenesulfonamide [CAS 56445-08-0] according to general procedure II. Yellow solid. MS (ISP) 582.0 [(M−H)$^-$]; mp 222° C.

Example 36

7-Difluoromethyl-5-(3-methyl-4-trifluoromethyl-phenyl)-pyrazolo[1,5-a]pyrimidine-3-carboxylic acid(3-sulfamoyl-phenyl)-amide The title compound was prepared from 7-difluoromethyl-5-(3-methyl-4-trifluoromethyl-phenyl)-pyrazolo[1,5-a]pyrimidine-3-carboxylic acid (example C.5) and 3-sulfamoyl-phenylamine [commercially available] according to general procedure II. Yellow solid. MS (ISP) 524.0 [(M−H)$^-$]; mp 252° C.

Example 37

5-(3-Methyl-4-trifluoromethyl-phenyl)-7-trifluoromethyl-pyrazolo[1,5-a]pyrimidine-3-carboxylic acid (3-sulfamoyl-phenyl)-amide The title compound was prepared from 5-(3-methyl-4-trifluoromethyl-phenyl)-7-trifluoromethyl-pyrazolo[1,5-a]pyrimidine-3-carboxylic acid (example C.8) and 3-sulfamoyl-phenylamine [commercially available] according to general procedure II. Yellow solid. MS (ISP) 542.1 [(M−H)$^-$]; mp 245° C.

Example 38

5-(3,4-Dichloro-phenyl)-7-difluoromethyl-pyrazolo[1,5-a]pyrimidine-3-carboxylic acid(3-sulfamoyl-phenyl)-amide The title compound was prepared from 5-(3,4-dichloro-phenyl)-7-difluoromethyl-pyrazolo[1,5-a]pyrimidine-3-carboxylic acid (example C.7) and 3-sulfamoyl-phenylamine [commercially available] according to general procedure II. Yellow solid. MS (ISP) 410.1 [(M−H)$^-$]; mp 306° C.

Example 39

5-(3,4-Dichloro-phenyl)-7-trifluoromethyl-pyrazolo[1,5-a]pyrimidine-3-carboxylic acid(3-sulfamoyl-phenyl)-amide The title compound was prepared from 5-(3,4-dichloro-phenyl)-7-trifluoromethyl-pyrazolo[1,5-a]pyrimidine-3-carboxylic acid (example C.9) and 3-sulfamoyl-phenylamine [commercially available] according to general procedure II. Yellow solid. MS (ISP) 528.0 [(M−H)$^-$]; mp 302° C.

Example 40

5-(4-Chloro-phenyl)-7-difluoromethyl-pyrazolo[1,5-a]pyrimidine-3-carboxylic acid(3-sulfamoyl-phenyl)-amide The title compound was prepared from 5-(4-chloro-phenyl)-7-difluoromethyl-pyrazolo[1,5-a]pyrimidine-3-carboxylic acid (example C.4) and 3-sulfamoyl-phenylamine [commercially available] according to general procedure II. Light yellow solid. MS (ISP) 476.0 [(M−H)$^-$]; mp 278° C.

Example 41

5-(4-Chloro-3-methyl-phenyl)-7-trifluoromethyl-pyrazolo[1,5-a]pyrimidine-3-carboxylic acid(3-sulfamoyl-phenyl)-amide The title compound was prepared from 5-(4-chloro-3-methyl-phenyl)-7-trifluoromethyl-pyrazolo[1,5-a]pyrimidine-3-carboxylic acid (example C.6) and 3-sulfamoyl-phenylamine [commercially available] according to general procedure II. Yellow solid. MS (ISP) 510.2 [(M+H)$^+$]; mp 275° C.

Example 42

7-Difluoromethyl-5-(4-trifluoromethyl-phenyl)-pyrazolo[1,5-a]pyrimidine-3-carboxylic acid(3-methylsulfamoyl-phenyl)-amide The title compound was prepared from 7-difluoromethyl-5-(4-trifluoromethyl-phenyl)-pyrazolo[1,5-a]pyrimidine-3-carboxylic acid (example C.1) and 3-amino-N-methyl-benzenesulfonamide [CAS 459434-40-3] according to general procedure II. Yellow solid. MS (ISP) 524.1 [(M−H)$^-$]; mp 255° C.

Example 43

7-Difluoromethyl-5-(4-trifluoromethyl-phenyl)-pyrazolo[1,5-a]pyrimidine-3-carboxylic acid(3-cyclopropylsulfamoyl-phenyl)-amide The title compound was prepared from 7-difluoromethyl-5-(4-trifluoromethyl-phenyl)-pyrazolo[1,5-a]pyrimidine-3-carboxylic acid (example C.1) and 3-amino-N-cyclopropyl-benzenesulfonamide [CAS 459434-39-0] according to general procedure II. Yellow solid. MS (ISP) 550.1 [(M−H)$^-$]; mp 252° C.

Example 44

7-Difluoromethyl-5-(4-trifluoromethyl-phenyl)-pyrazolo[1,5-a]pyrimidine-3-carboxylic acid(3-isopropylsulfamoyl-phenyl)-amide The title compound was prepared from 7-difluoromethyl-5-(4-trifluoromethyl-phenyl)-pyrazolo[1,5-a]pyrimidine-3-carboxylic acid (example C.1) and 3-amino-N-isopropyl-benzenesulfonamide [CAS 118837-66-4] according to general procedure II. Light yellow solid. MS (ISP) 552.0 [(M−H$^-$]; mp 229° C.

Example 45

7-Difluoromethyl-5-(4-trifluoromethyl-phenyl)-pyrazolo[1,5-a]pyrimidine-3-carboxylic acid(3-sulfamoyl-phenyl)-amide The title compound was prepared from 7-difluoromethyl-5-(4-trifluoromethyl-phenyl)-pyrazolo[1,5-a]pyrimidine-3-carboxylic acid (example C.1) and 3-sulfamoyl-phenylamine [commercially available] according to general procedure II. Yellow solid. MS (ISP) 510.2 [(M−H)$^-$]; mp 258° C.

Example 46

7-Trifluoromethyl-5-(4-trifluoromethyl-phenyl)-pyrazolo[1,5-a]pyrimidine-3-carboxylic acid(3-cyclopropylsulfamoyl-phenyl)-amide The title compound was prepared from 7-trifluoromethyl-5-(4-trifluoromethyl-phenyl)-pyrazolo[1,5-a]pyrimidine-3-carboxylic acid (example C.2) and 3-amino-N-cyclopropyl-benzenesulfonamide [CAS 459434-39-0] according to general procedure II. Yellow solid. MS (ISP) 568.0 [(M−H$^-$]; mp 232° C.

Example 47

7-Trifluoromethyl-5-(4-trifluoromethyl-phenyl)-pyrazolo[1,5-a]pyrimidine-3-carboxylic acid(3-methylsulfamoyl-phenyl)-amide The title compound was prepared from 7-trifluoromethyl-5-(4-trifluoromethyl-phenyl)-pyrazolo[1,5-a]pyrimidine-3-carboxylic acid (example C.2) and 3-amino-N-methyl-benzenesulfonamide [CAS 459434-40-3] according to general procedure II. Yellow solid. MS (ISP) 542.0 [(M−H)$^-$]; mp 232° C.

Example 48

7-Difluoromethyl-5-(4-trifluoromethyl-phenyl)-pyrazolo[1,5-a]pyrimidine-3-carboxylic acid(3-methanesulfonyl-phenyl)-amide The title compound was prepared from 7-difluoromethyl-5-(4-trifluoromethyl-phenyl)-pyrazolo[1,5-a]pyrimidine-3-carboxylic acid (example C.1) and 3-methanesulfonyl-phenylamine [commercially available as hydrochloride] according to general procedure II. Yellow solid. MS (ISP) 511.4 [(M+H)$^+$]; mp 251° C.

Example 49

7-Trifluoromethyl-5-(4-trifluoromethyl-phenyl)-pyrazolo[1,5-a]pyrimidine-3-carboxylic acid(3-isopropylsulfamoyl-phenyl)-amide The title compound was prepared from 7-trifluoromethyl-5-(4-trifluoromethyl-phenyl)-pyrazolo[1,5-a]pyrimidine-3-carboxylic acid (example C.2) and 3-amino-N-isopropyl-benzenesulfonamide [CAS 118837-66-4] according to general procedure II. Yellow solid. MS (ISP) 570.2 [(M−H)$^-$]; mp 222° C.

Example 50

7-Trifluoromethyl-5-(4-trifluoromethyl-phenyl)-pyrazolo[1,5-a]pyrimidine-3-carboxylic acid(3-methanesulfonyl-phenyl)-amide The title compound was prepared from 7-trifluoromethyl-5-(4-trifluoromethyl-phenyl)-pyrazolo[1,5-a]pyrimidine-3-carboxylic acid (example C.2) and 3-methanesulfonyl-phenylamine [commercially available as hydrochloride] according to general procedure II. Yellow solid. MS (ISP) 529.3 [(M+H)$^+$]; mp 259° C.

Example 51

5-(4-Chloro-phenyl)-7-trifluoromethyl-pyrazolo[1,5-a]pyrimidine-3-carboxylic acid(3-sulfamoyl-phenyl)-amide The title compound was prepared from 5-(4-chloro-phenyl)-7-trifluoromethyl-pyrazolo[1,5-a]pyrimidine-3-carboxylic acid (example C.4) and 3-sulfamoyl-phenylamine [commercially available] according to general procedure II. Yellow solid. MS (ISP) 494.0 [(M−H)$^-$]; mp 260° C.

Example 52

7-Difluoromethyl-5-(4-trifluoromethyl-phenyl)-pyrazolo[1,5-a]pyrimidine-3-carboxylic acid [3-(2,2,2-trifluoro-ethylsulfamoyl)-phenyl]-amide The title compound was prepared from 7-difluoromethyl-5-(4-trifluoromethyl-phenyl)-pyrazolo[1,5-a]pyrimidine-3-carboxylic acid (example C.1) and 3-amino-N-(2,2,2-trifluoroethyl)-benzenesulfonamide [synthesis: see part aniline derivatives] according to general procedure II. Yellow solid. MS (ISP) 592.0 [(M−H)⁻]; mp 257° C.

Example 53

5-(4-Chloro-phenyl)-7-trifluoromethyl-pyrazolo[1,5-a]pyrimidine-3-carboxylic acid(3-methanesulfonyl-phenyl)-amide The title compound was prepared from 5-(4-chloro-phenyl)-7-trifluoromethyl-pyrazolo[1,5-a]pyrimidine-3-carboxylic acid (example C.4) and 3-methanesulfonyl-phenylamine [commercially available as hydrochloride] according to general procedure II. Yellow solid. MS (ISP) 495.3 [(M+H)⁺]; mp 305° C.

Example 54

7-Trifluoromethyl-5-(4-trifluoromethyl-phenyl)-pyrazolo[1,5-a]pyrimidine-3-carboxylic acid[3-(2,2,2-trifluoro-ethylsulfamoyl)-phenyl]-amide The title compound was prepared from 7-trifluoromethyl-5-(4-trifluoromethyl-phenyl)-pyrazolo[1,5-a]pyrimidine-3-carboxylic acid (example C.2) and 3-amino-N-(2,2,2-trifluoroethyl)-benzenesulfonamide (example B.1) according to general procedure II. Yellow solid. MS (ISP) 610.0 [(M−H)⁻]; mp 259° C.

Example 55

5-(3,4-Dichloro-phenyl)-7-difluoromethyl-pyrazolo[1,5-a]pyrimidine-3-carboxylic acid(3-methanesulfonyl-phenyl)-amide The title compound was prepared from 5-(3,4-dichloro-phenyl)-7-trifluoromethyl-pyrazolo[1,5-a]pyrimidine-3-carboxylic acid (example C.9) and 3-methanesulfonyl-phenylamine [commercially available as hydrochloride] according to general procedure II. Yellow solid. MS (ISP) 511.3 [(M+H)⁺]; mp 262° C.

Example 56

5-(3,4-Dichloro-phenyl)-7-trifluoromethyl-pyrazolo[1,5-a]pyrimidine-3-carboxylic acid(3-methanesulfonyl-phenyl)-amide The title compound was prepared from 5-(3,4-dichloro-phenyl)-7-difluoromethyl-pyrazolo[1,5-a]pyrimidine-3-carboxylic acid (example C.7) and 3-methanesulfonyl-phenylamine [commercially available as hydrochloride] according to general procedure II. Yellow solid. MS (ISP) 529.2 [(M+H)⁺]; mp 263° C.

Example 57

7-Difluoromethyl-5-(3-methyl-4-trifluoromethyl-phenyl)-pyrazolo[1,5-a]pyrimidine-3-carboxylic acid(3-methanesulfonyl-phenyl)-amide The title compound was prepared from 7-difluoromethyl-5-(3-methyl-4-trifluoromethyl-phenyl)-pyrazolo[1,5-a]pyrimidine-3-carboxylic acid (example C.5) and 3-methanesulfonyl-phenylamine [commercially available as hydrochloride] according to general procedure II. Light brown solid. MS (ISP) 525.2 [(M+H)⁺]; mp 261° C.

Example 58

5-(3-Methyl-4-trifluoromethyl-phenyl)-7-trifluoromethyl-pyrazolo[1,5-a]pyrimidine-3-carboxylic acid (3-methanesulfonyl-phenyl)-amide The title compound was prepared from 5-(3-methyl-4-trifluoromethyl-phenyl)-7-trifluoromethyl-pyrazolo[1,5-a]pyrimidine-3-carboxylic acid (example C.8) and 3-methanesulfonyl-phenylamine [commercially available as hydrochloride] according to general procedure II. Yellow solid. MS (ISP) 543.3 [(M+H)⁺]; mp 233° C.

Example 59

5-(3-Methyl-4-trifluoromethyl-phenyl)-7-trifluoromethyl-pyrazolo[1,5-a]pyrimidine-3-carboxylic acid (3-cyclopropylsulfamoyl-phenyl)-amide The title compound was prepared from 5-(3-methyl-4-trifluoromethyl-phenyl)-7-trifluoromethyl-pyrazolo[1,5-a]pyrimidine-3-carboxylic acid (example C.8) and 3-amino-N-cyclopropyl-benzenesulfonamide [CAS 459434-39-0] according to general procedure II. Yellow solid. MS (ISP) 582.0 [(M−H)⁻]; mp 201° C.

Example 60

5-(3,4-Dichloro-phenyl)-7-trifluoromethyl-pyrazolo[1,5-a]pyrimidine-3-carboxylic acid(3-cyclopropylsulfamoyl-phenyl)-amide The title compound was prepared from 5-(3,4-dichloro-phenyl)-7-trifluoromethyl-pyrazolo[1,5-a]pyrimidine-3-carboxylic acid (example C.9) and 3-amino-N-cyclopropyl-benzenesulfonamide [CAS 459434-39-0] according to general procedure II. Yellow solid. MS (ISP) 567.9 [(M−H)⁻]; mp 248° C.

Example 61

5-(4-Chloro-phenyl)-7-trifluoromethyl-pyrazolo[1,5-a]pyrimidine-3-carboxylic acid(3-cyclopropylsulfamoyl-phenyl)-amide The title compound was prepared from 5-(4-chloro-phenyl)-7-trifluoromethyl-pyrazolo[1,5-a]pyrimidine-3-carboxylic acid (example C.4) and 3-amino-N-cyclopropyl-benzenesulfonamide [CAS 459434-39-0] according to general procedure II. Yellow solid. MS (ISP) 534.1 [(M−H)⁻]; mp 257° C.

Example 62

5-(4-Chloro-3-methyl-phenyl)-7-trifluoromethyl-pyrazolo[1,5-a]pyrimidine-3-carboxylic acid(3-cyclopropylsulfamoyl-phenyl)-amide The title compound was prepared from 5-(4-chloro-3-methyl-phenyl)-7-trifluoromethyl-pyrazolo[1,5-a]pyrimidine-3-carboxylic acid (example C.6) and 3-amino-N-cyclopropyl-benzenesulfonamide [CAS 459434-39-0] according to general procedure II. Yellow solid. MS (ISP) 548.1 [(M−H)⁻]; mp 244° C.

Example 63

7-Difluoromethyl-5-(3-methyl-4-trifluoromethyl-phenyl)-pyrazolo[1,5-a]pyrimidine-3-carboxylic acid(3-cyclopropylsulfamoyl-phenyl)-amide The title compound was prepared from 7-difluoromethyl-5-(3-methyl-4-trifluoromethyl-phenyl)-pyrazolo[1,5-a]pyrimidine-3-carboxylic acid (example C.5) and 3-amino-N-cyclopropyl-benzenesulfonamide [CAS 459434-39-0] according to general procedure II. Light yellow solid. MS (ISP) 564.2 [(M−H)⁻]; mp 199° C.

Example 64

5-(3,4-Dichloro-phenyl)-7-difluoromethyl-pyrazolo[1,5-a]pyrimidine-3-carboxylic acid(3-cyclopropylsulfamoyl-phenyl)-amide The title compound was prepared from 5-(3,4-dichloro-phenyl)-7-difluoromethyl-pyrazolo[1,5-a]pyrimidine-3-carboxylic acid (example C.7) and 3-amino-N-cyclopropyl-benzenesulfonamide [CAS 459434-39-0] according to general procedure II. Light yellow solid. MS (ISP) 550.0 [(M−H)⁻]; mp 254° C.

Example 65

5-(4-Chloro-phenyl)-7-difluoromethyl-pyrazolo[1,5-a]pyrimidine-3-carboxylic acid(3-cyclopropylsulfamoyl-phenyl)-amide The title compound was prepared from 5-(4-dichloro-phenyl)-7-difluoromethyl-pyrazolo[1,5-a]pyrimidine-3-carboxylic acid (example C.3) and 3-amino-N-cyclopropyl-benzenesulfonamide [CAS 459434-39-0] according to general procedure II. Light yellow solid. MS (ISP) 516.1 [(M−H)⁻]; mp 262° C.

Example 66

7-Trifluoromethyl-5-(4-trifluoromethyl-phenyl)-pyrazolo[1,5-a]pyrimidine-3-carboxylic acid(3-isobutylsulfamoyl-phenyl)-amide The title compound was prepared from 7-trifluoromethyl-5-(4-trifluoromethyl-phenyl)-pyrazolo[1,5-a]pyrimidine-3-carboxylic acid (example C.2) and 3-amino-N-isobutyl-benzenesulfonamide [CAS 608523-95-1] according to general procedure II. Yellow solid. MS (ISP) 584.1 [(M−H)⁻]; mp 205° C.

Example 67

7-Trifluoromethyl-5-(4-trifluoromethyl-phenyl)-pyrazolo[1,5-a]pyrimidine-3-carboxylic acid[3-(cyclopropylmethyl-sulfamoyl)-phenyl]-amide The title compound was prepared from 7-trifluoromethyl-5-(4-trifluoromethyl-phenyl)-pyrazolo[1,5-a]pyrimidine-3-carboxylic acid (example C.2) and 3-amino-N-cyclopropylmethyl-benzenesulfonamide (example B.2) according to general procedure II. Yellow solid. MS (ISP) 582.1 [(M−H)⁻]; mp 234° C.

Example 68

5-(3-Ethoxy-4-trifluoromethyl-phenyl)-7-trifluoromethyl-pyrazolo[1,5-a]pyrimidine-3-carboxylic acid (3-methanesulfonyl-phenyl)-amide The title compound was prepared from 5-(3-ethoxy-4-trifluoromethyl-phenyl)-7-trifluoromethyl-pyrazolo[1,5-a]pyrimidine-3-carboxylic acid (example C.11) and 3-methanesulfonyl-phenylamine [commercially available as hydrochloride] according to general procedure II. Yellow solid. MS (ISP) 573.2 [(M+H)⁺]; mp 215° C.

Example 69

7-Difluoromethyl-5-(3-ethoxy-4-trifluoromethyl-phenyl)-pyrazolo[1,5-a]pyrimidine-3-carboxylic acid(3-methanesulfonyl-phenyl)-amide The title compound was prepared from 7-difluoromethyl-5-(3-ethoxy-4-trifluoromethyl-phenyl)-pyrazolo[1,5-a]pyrimidine-3-carboxylic acid (example C.12) and 3-methanesulfonyl-phenylamine [commercially available as hydrochloride] according to general procedure II. Yellow solid. MS (ISP) 555.3 [(M+H)⁺]; mp 211° C.

Example 70

7-Difluoromethyl-5-(3-ethoxy-4-trifluoromethyl-phenyl)-pyrazolo[1,5-a]pyrimidine-3-carboxylic acid(3-cyclopropylsulfamoyl-phenyl)-amide The title compound was prepared from 7-difluoromethyl-5-(3-ethoxy-4-trifluoromethyl-phenyl)-pyrazolo[1,5-a]pyrimidine-3-carboxylic acid (example C.12) and 3-amino-N-cyclopropyl-benzenesulfonamide [CAS 459434-39-0] according to general procedure II. Yellow solid. MS (ISP) 594.1 [(M−H)⁻]; mp 213° C.

Example 71

5-(3-Ethoxy-4-trifluoromethyl-phenyl)-7-trifluoromethyl-pyrazolo[1,5-a]pyrimidine-3-carboxylic acid (3-cyclopropylsulfamoyl-phenyl)-amide The title compound was prepared from 5-(3-ethoxy-4-trifluoromethyl-phenyl)-7-trifluoromethyl-pyrazolo[1,5-a]pyrimidine-3-carboxylic acid (example C.11) and 3-amino-N-cyclopropyl-benzenesulfonamide [CAS 459434-39-0] according to general procedure II. Yellow solid. MS (ISP) 612.2 [(M−H)⁻]; mp 225° C.

Example 72

7-Difluoromethyl-5-(4-trifluoromethyl-phenyl)-pyrazolo[1,5-a]pyrimidine-3-carboxylic acid(3-isobutyl-sulfamoyl-phenyl)-amide The title compound was prepared from 7-difluoromethyl-5-(4-trifluoromethyl-phenyl)-pyrazolo[1,5-a]pyrimidine-3-carboxylic acid (example C.1) and 3-amino-N-isobutyl-benzenesulfonamide [CAS 608523-95-1] according to general procedure II. Yellow solid. MS (ISP) 566.2 [(M−H)$^-$]; mp 186° C.

Example 73

7-Difluoromethyl-5-(4-trifluoromethyl-phenyl)-pyrazolo[1,5-a]pyrimidine-3-carboxylic acid [3-(cyclopropylmethyl-sulfamoyl)-phenyl]-amide The title compound was prepared from 7-difluoromethyl-5-(4-trifluoromethyl-phenyl)-pyrazolo[1,5-a]pyrimidine-3-carboxylic acid (example C.1) and 3-amino-N-cyclopropylmethyl-benzenesulfonamide (example B.2) according to general procedure II. Yellow solid. MS (ISP) 564.2 [(M−H)$^-$]; mp 238° C.

Example 74

7-Difluoromethyl-5-(4-trifluoromethyl-phenyl)-pyrazolo[1,5-a]pyrimidine-3-carboxylic acid(3-phenyl-sulfamoyl-phenyl)-amide The title compound was prepared from 7-difluoromethyl-5-(4-trifluoromethyl-phenyl)-pyrazolo[1,5-a]pyrimidine-3-carboxylic acid (example C.1) and 3-amino-N-phenyl-benzenesulfonamide [commercially available] according to general procedure II. Yellow solid. MS (ISP) 586.2 [(M−H)$^-$]; mp 228° C.

Example 75

7-Difluoromethyl-5-(4-trifluoromethyl-phenyl)-pyrazolo[1,5-a]pyrimidine-3-carboxylic acid(3-benzyl-sulfamoyl-phenyl)-amide The title compound was prepared from 7-difluoromethyl-5-(4-trifluoromethyl-phenyl)-pyrazolo[1,5-a]pyrimidine-3-carboxylic acid (example C.1) and 3-amino-N-benzyl-benzenesulfonamide [CAS No. 303780-52-1] according to general procedure II. Light yellow solid. MS (ISP) 600.1 [(M−H)$^-$]; mp 230° C.

Example 76

7-Trifluoromethyl-5-(4-trifluoromethyl-phenyl)-pyrazolo[1,5-a]pyrimidine-3-carboxylic acid(3-phenylsulfamoyl-phenyl)-amide The title compound was prepared from 7-trifluoromethyl-5-(4-trifluoromethyl-phenyl)-pyrazolo[1,5-a]pyrimidine-3-carboxylic acid (example C.2) and 3-amino-N-phenyl-benzenesulfonamide [commercially available] according to general procedure II. Yellow solid. MS (ISP) 604.0 [(M−H)$^-$]; mp 258° C.

Example 77

7-Trifluoromethyl-5-(4-trifluoromethyl-phenyl)-pyrazolo[1,5-a]pyrimidine-3-carboxylic acid(3-benzylsulfamoyl-phenyl)-amide The title compound was prepared from 7-trifluoromethyl-5-(4-trifluoromethyl-phenyl)-pyrazolo[1,5-a]pyrimidine-3-carboxylic acid (example C.2) and 3-amino-N-benzyl-benzenesulfonamide [CAS No. 303780-52-1] according to general procedure II. Yellow solid. MS (ISP) 618.1 [(M−H)$^-$]; mp 227° C.

Example 78

5-[3-(2,2,2-Trifluoro-ethoxy)-4-trifluoromethyl-phenyl]-7-trifluoromethyl-pyrazolo[1,5-a]pyrimidine-3-carboxylic acid(3-sulfamoyl-phenyl)-amide The title compound was prepared from 5-[3-(2,2,2-trifluoroethoxy)-4-trifluoromethyl-phenyl]-7-trifluoromethyl-pyrazolo[1,5-a]pyrimidine-3-carboxylic acid (example C.10) and 3-sulfamoyl-phenylamine [commercially available] according to general procedure II. Yellow solid. MS (ISP) 626.1 [(M−H)$^-$]; mp 233° C.

Example 79

7-Difluoromethyl-5-[3-(2,2,2-trifluoro-ethoxy)-4-trifluoromethyl-phenyl]-pyrazolo[1,5-a]pyrimidine-3-carboxylic acid(3-sulfamoyl-phenyl)-amide The title compound was prepared from 7-difluoromethyl-5-[3-(2,2,2-trifluoroethoxy)-4-trifluoromethyl-phenyl]-pyrazolo[1,5-a]pyrimidine-3-carboxylic acid (example C.13) and 3-sulfamoyl-phenylamine [commercially available] according to general procedure II. Light yellow solid. MS (ISP) 607.9 [(M−H)$^-$]; mp 241° C.

Example 80

5-[3-(2,2,2-Trifluoro-ethoxy)-4-trifluoromethyl-phenyl]-7-trifluoromethyl-pyrazolo[1,5-a]pyrimidine-3-carboxylic acid(3-methanesulfonyl-phenyl)-amide The title compound was prepared from 5-[3-(2,2,2-trifluoro-ethoxy)-4-trifluoromethyl-phenyl]-7-trifluoromethyl-pyrazolo[1,5-a]pyrimidine-3-carboxylic acid (example C.10) and 3-methanesulfonyl-phenylamine [commercially available as hydrochloride] according to general procedure II. Yellow solid. MS (EI) 626.3 [M]; mp 227° C.

Example 81

7-Difluoromethyl-5-[3-(2,2,2-trifluoro-ethoxy)-4-trifluoromethyl-phenyl]-pyrazolo[1,5-a]pyrimidine-3-carboxylic acid(3-methanesulfonyl-phenyl)-amide The title compound was prepared from 7-difluoromethyl-5-[3-(2,2,2-trifluoro-ethoxy)-4-trifluoromethyl-phenyl]-pyrazolo[1,5-a]pyrimidine-3-carboxylic acid (example C.13) and 3-methanesulfonyl-phenylamine [commercially available as hydrochloride] according to general procedure II. Yellow solid. MS (EI) 608.3 [M]; mp 207° C.

Example 82

7-Trifluoromethyl-5-(4-trifluoromethyl-phenyl)-pyrazolo[1,5-a]pyrimidine-3-carboxylic acid[3-(2-hydroxy-ethylsulfamoyl)-phenyl]-amide The title compound was prepared from 7-trifluoromethyl-5-(4-trifluoromethyl-phenyl)-pyrazolo[1,5-a]pyrimidine-3-carboxylic acid (example C.2) and 3-amino-N-(2-hydroxy-ethyl)-benzenesulfonamide [CAS 436095-41-9] according to general procedure II. Yellow solid. MS (ISP) 572.0 [(M−H)⁻]; mp 227° C.

Example 83

7-Difluoromethyl-5-(4-trifluoromethyl-phenyl)-pyrazolo[1,5-a]pyrimidine-3-carboxylic acid [3-(2-hydroxy-ethylsulfamoyl)-phenyl]-amide The title compound was prepared from 7-difluoromethyl-5-(4-trifluoromethyl-phenyl)-pyrazolo[1,5-a]pyrimidine-3-carboxylic acid (example C.1) and 3-amino-N-(2-hydroxy-ethyl)-benzenesulfonamide [CAS 436095-41-9] according to general procedure II. Light yellow solid. MS (ISP) 554.0 [(M−H)⁻]; mp 231° C.

Example 84

5-(4-Chloro-3-methyl-phenyl)-7-difluoromethyl-pyrazolo[1,5-a]pyrimidine-3-carboxylic acid(3-sulfamoyl-phenyl)-amide The title compound was prepared from 5-(4-chloro-3-methyl-phenyl)-7-difluoromethyl-pyrazolo[1,5-a]pyrimidine-3-carboxylic acid (example C.14) and 3-sulfamoyl-phenylamine [commercially available] according to general procedure II. Yellow solid. MS (EI) 491.1 [M]; mp 264° C.

Example 85

5-(4-Chloro-3-methyl-phenyl)-7-difluoromethyl-pyrazolo[1,5-a]pyrimidine-3-carboxylic acid(3-methanesulfonyl-phenyl)-amide The title compound was prepared from 7-difluoromethyl-5-(3-methyl-4-chloro-phenyl)-pyrazolo[1,5-a]pyrimidine-3-carboxylic acid (Example C.14) and 3-methanesulfonyl-phenylamine [commercially available as hydrochloride] according to general procedure II. Yellow solid. MS (ISP) 488.9 [(M−H)⁻]; mp 270° C.

Example 86

7-Difluoromethyl-5-(4-trifluoromethyl-phenyl)-pyrazolo[1,5-a]pyrimidine-3-carboxylic acid(3-trifluoromethanesulfonyl-phenyl)-amide The title compound was prepared from 7-difluoromethyl-5-(4-trifluoromethyl-phenyl)-pyrazolo[1,5-a]pyrimidine-3-carboxylic acid (example C.1) and 3-trifluoromethanesulfonyl-phenylamine [commercially available] according to general procedure II. Yellow solid. MS (ISP) 565.3 [(M+H)⁺]; mp 207° C.

Example 87

7-Trifluoromethyl-5-(4-trifluoromethyl-phenyl)-pyrazolo[1,5-a]pyrimidine-3-carboxylic acid(3-trifluoromethanesulfonyl-phenyl)-amide The title compound was prepared from 7-trifluoromethyl-5-(4-trifluoromethyl-phenyl)-pyrazolo[1,5-a]pyrimidine-3-carboxylic acid (example C.2) and 3-trifluoromethanesulfonyl-phenylamine [commercially available] according to general procedure II. Yellow solid. MS (ISP) 583.3 [(M+H)⁺]; mp 207° C.

Example 88

7-Difluoromethyl-5-(4-trifluoromethyl-phenyl)-pyrazolo[1,5-a]pyrimidine-3-carboxylic acid {3-[(pyridin-4-ylmethyl)-sulfamoyl]-phenyl}-amide The title compound was prepared from 7-difluoromethyl-5-(4-trifluoromethyl-phenyl)-pyrazolo[1,5-a]pyrimidine-3-carboxylic acid (example C.1) and 3-amino-N-pyridin-4-ylmethyl-benzenesulfonamide (example B.3) according to general procedure II. Yellow solid. MS (ISP) 601.2 [(M−H)⁻]; mp 221° C.

Example 89

7-Trifluoromethyl-5-(4-trifluoromethyl-phenyl)-pyrazolo[1,5-a]pyrimidine-3-carboxylic acid{3-[(pyridin-4-ylmethyl)-sulfamoyl]-phenyl}-amide The title compound was prepared from 7-trifluoromethyl-5-(4-trifluoromethyl-phenyl)-pyrazolo[1,5-a]pyrimidine-3-carboxylic acid (example C.2) and 3-amino-N-pyridin-4-ylmethyl-benzenesulfonamide (example B.3) according to general procedure II. Yellow solid. MS (ISP) 619.2 [(M−H)⁻]; mp 251° C.

Example 90

7-Difluoromethyl-5-(4-trifluoromethyl-phenyl)-pyrazolo[1,5-a]pyrimidine-3-carboxylic acid [3-(2-hydroxy-ethanesulfonyl)-phenyl]-amide The title compound was prepared from 7-difluoromethyl-5-(4-trifluoromethyl-phenyl)-pyrazolo[1,5-a]pyrimidine-3-carboxylic acid (example C.1) and 3-(2-hydroxy-ethanesulfonyl)-aniline [commercially available] according to general procedure II. Yellow solid. MS (ISP) 541.4 [(M+H)⁺]; mp 205° C.

Example 91

7-Trifluoromethyl-5-(4-trifluoromethyl-phenyl)-pyrazolo[1,5-a]pyrimidine-3-carboxylic acid[3-(2-hydroxy-ethanesulfonyl)-phenyl]-amide The title compound was prepared from 7-trifluoromethyl-5-(4-trifluoromethyl-phenyl)-pyrazolo[1,5-a]pyrimidine-3-carboxylic acid (example C.1) and 3-(2-hydroxy-ethanesulfonyl)-aniline [commercially available] according to general procedure II. Yellow solid. MS (ISP) 559.4 [(M+H)⁺]; mp 237° C.

Example 92

7-Difluoromethyl-5-(4-trifluoromethyl-phenyl)-pyrazolo[1,5-a]pyrimidine-3-carboxylic acid(3-sulfamoylmethyl-phenyl)-amide The title compound was prepared from 7-difluoromethyl-5-(4-trifluoromethyl-phenyl)-pyrazolo[1,5-a]pyrimidine-3-carboxylic acid (example C.1) and 3-(2-hydroxy-ethanesulfonyl)-aniline [CAS-Nr. 344750-15-8; prepared from commercially available 3-nitro-phenylmethane-sulfonyl chloride] according to general procedure II. Yellow solid. MS (ISP) 524.0 [(M−H)−]; mp 280° C.

Example 93

7-Trifluoromethyl-5-(4-trifluoromethyl-phenyl)-pyrazolo[1,5-a]pyrimidine-3-carboxylic acid(3-sulfamoylmethyl-phenyl)-amide The title compound was prepared from 7-trifluoromethyl-5-(4-trifluoromethyl-phenyl)-pyrazolo[1,5-a]pyrimidine-3-carboxylic acid (example C.2) and 3-(2-hydroxy-ethanesulfonyl)-aniline [CAS-Nr. 344750-15-8; prepared from commercially available 3-nitro-phenylmethane-sulfonyl chloride] according to general procedure II. Yellow solid. MS (ISP) 542.0 [(M−H)−]; mp 298° C.

Example 94

7-Difluoromethyl-5-(4-trifluoromethyl-phenyl)-pyrazolo[1,5-a]pyrimidine-3-carboxylic acid[3-(2,2-dimethyl-propylsulfamoyl)-phenyl]-amide The title compound was prepared from 7-difluoromethyl-5-(4-trifluoromethyl-phenyl)-pyrazolo[1,5-a]pyrimidine-3-carboxylic acid (example C.1) and 3-amino-N-(2,2-dimethyl-propyl)-benzenesulfonamide (example B.4) according to general procedure II. Light yellow solid. MS (ISP) 580.3 [(M−H−]; mp 208° C.

Example 95

7-Difluoromethyl-5-(4-trifluoromethyl-phenyl)-pyrazolo[1,5-a]pyrimidine-3-carboxylic acid(3-tert-butylsulfamoyl-phenyl)-amide The title compound was prepared from 7-difluoromethyl-5-(4-trifluoromethyl-phenyl)-pyrazolo[1,5-a]pyrimidine-3-carboxylic acid (example C.1) and 3-amino-N-tert-butyl-benzenesulfonamide [CAS 608523-94-0] according to general procedure II. Light yellow solid. MS (ISP) 566.2 [(M−H−]; mp 228° C.

Example 96

7-Trifluoromethyl-5-(4-trifluoromethyl-phenyl)-pyrazolo[1,5-a]pyrimidine-3-carboxylic acid[3-(2,2-dimethyl-propylsulfamoyl)-phenyl]-amide The title compound was prepared from 7-trifluoromethyl-5-(4-trifluoromethyl-phenyl)-pyrazolo[1,5-a]pyrimidine-3-carboxylic acid (example C.2) and 3-amino-N-(2,2-dimethyl-propyl)-benzenesulfonamide (example B.4) according to general procedure II. Light yellow solid. MS (ISP) 598.1 [(M−H−]; mp 231° C.

Example 97

7-Trifluoromethyl-5-(4-trifluoromethyl-phenyl)-pyrazolo[1,5-a]pyrimidine-3-carboxylic acid(3-tert-butylsulfamoyl-phenyl)-amide The title compound was prepared from 7-trifluoromethyl-5-(4-trifluoromethyl-phenyl)-pyrazolo[1,5-a]pyrimidine-3-carboxylic acid (example C.2) and 3-amino-N-tert-butyl-benzenesulfonamide [CAS 608523-94-0] according to general procedure II. Light yellow solid. MS (ISP) 584.1 [(M−H−]; mp 232° C.

Example 98

5-(3-Chloro-4-trifluoromethyl-phenyl)-7-difluoromethyl-pyrazolo[1,5-a]pyrimidine-3-carboxylic acid (3-sulfamoyl-phenyl)-amide The title compound was prepared from 5-(3-chloro-4-trifluoromethyl-phenyl)-7-difluoromethyl-pyrazolo[1,5-a]pyrimidine-3-carboxylic acid (example C.15) and 3-sulfamoyl-phenylamine [commercially available] according to general procedure II. Brown solid. MS (ISP) 543.9 [(M−H)−]; mp 272° C.

Example 99

7-Difluoromethyl-5-(3-fluoro-4-trifluoromethyl-phenyl)-pyrazolo[1,5-a]pyrimidine-3-carboxylic acid(3-sulfamoyl-phenyl)-amide The title compound was prepared from 7-difluoromethyl-5-(3-fluoro-4-trifluoromethyl-phenyl)-pyrazolo[1,5-a]pyrimidine-3-carboxylic acid (example C.16) and 3-sulfamoyl-phenylamine [commercially available] according to general procedure II. Yellow solid. MS (ISP) 528.0 [(M−H)−]; mp 262° C.

Example 100

5-(3-Chloro-4-trifluoromethyl-phenyl)-7-trifluoromethyl-pyrazolo[1,5-a]pyrimidine-3-carboxylic acid (3-sulfamoyl-phenyl)-amide The title compound was prepared from 5-(3-chloro-4-trifluoromethyl-phenyl)-7-trifluoromethyl-pyrazolo[1,5-a]pyrimidine-3-carboxylic acid (example C.17) and 3-sulfamoyl-phenylamine [commercially available] according to general procedure II. Yellow solid. MS (ISP) 562.1 [(M+H)+]; mp 287° C.

Example 101

5-(3-Fluoro-4-trifluoromethyl-phenyl)-7-trifluoromethyl-pyrazolo[1,5-a]pyrimidine-3-carboxylic acid (3-sulfamoyl-phenyl)-amide The title compound was prepared from 5-(3-fluororo-4-trifluoromethyl-phenyl)-7-trifluoromethyl-pyrazolo[1,5-a]pyrimidine-3-carboxylic acid (example C.18) and 3-sulfamoyl-phenylamine [commercially available] according to general procedure II. Yellow solid. MS (ISP) 546.1 [(M+H)+]; mp 259° C.

Example 102

5-(3-Chloro-4-trifluoromethyl-phenyl)-7-difluoromethyl-pyrazolo[1,5-a]pyrimidine-3-carboxylic acid (3-methanesulfonyl-phenyl)-amide The title compound was prepared from 5-(3-chloro-4-trifluoromethyl-phenyl)-7-difluoromethyl-pyrazolo[1,5-a]pyrimidine-3-carboxylic acid (example C.15) and 3-methanesulfonyl-phenylamine [commercially available as hydrochloride] according to general procedure II. Light brown solid. MS (ISP) 543.0 [(M+H)+]; mp 228° C.

Example 103

7-Difluoromethyl-5-(3-fluoro-4-trifluoromethyl-phenyl)-pyrazolo[1,5-a]pyrimidine-3-carboxylic acid(3-methanesulfonyl-phenyl)-amide The title compound was prepared from 7-difluoromethyl-5-(3-fluoro-4-trifluoromethyl-phenyl)-pyrazolo[1,5-a]pyrimidine-3-carboxylic acid (example C.16) and 3-methanesulfonyl-phenylamine [commercially available as hydrochloride] according to general procedure II. Light brown solid. MS (ISP) 527.0 [(M+H)+]; mp 238° C.

Example 104

5-(3-Chloro-4-trifluoromethyl-phenyl)-7-trifluoromethyl-pyrazolo[1,5-a]pyrimidine-3-carboxylic acid (3-methanesulfonyl-phenyl)-amide The title compound was prepared from 5-(3-chloro-4-trifluoromethyl-phenyl)-7-trifluoromethyl-pyrazolo[1,5-a]pyrimidine-3-carboxylic acid (example C.17) and 3-methanesulfonyl-phenylamine [commercially available as hydrochloride] according to general procedure II. Yellow solid. MS (ISP) 561.1 [(M+H)$^+$]; mp 268° C.

Example 105

5-(3-Fluoro-4-trifluoromethyl-phenyl)-7-trifluoromethyl-pyrazolo[1,5-a]pyrimidine-3-carboxylic acid (3-methanesulfonyl-phenyl)-amide The title compound was prepared from 5-(3-fluororo-4-trifluoromethyl-phenyl)-7-trifluoromethyl-pyrazolo[1,5-a]pyrimidine-3-carboxylic acid (example C.18) and 3-methanesulfonyl-phenylamine [commercially available as hydrochloride] according to general procedure II. Yellow solid. MS (ISP) 545.1 [(M+H)$^+$]; mp 246° C.

Example 106

7-Difluoromethyl-5-(4-trifluoromethyl-phenyl)-pyrazolo[1,5-a]pyrimidine-3-carboxylic acid {3-[(pyridin-3-ylmethyl)-sulfamoyl]-phenyl}-amide The title compound was prepared from 7-difluoromethyl-5-(4-trifluoromethyl-phenyl)-pyrazolo[1,5-a]pyrimidine-3-carboxylic acid (example C.1) and 3-amino-N-pyridin-3-ylmethyl-benzenesulfonamide (example B.5) according to general procedure II. Yellow solid. MS (ISP) 603.2 [(M+H$^+$]; mp 256° C.

Example 107

7-Trifluoromethyl-5-(4-trifluoromethyl-phenyl)-pyrazolo[1,5-a]pyrimidine-3-carboxylic acid{3-[(pyridin-3-ylmethyl)-sulfamoyl]-phenyl}-amide The title compound was prepared from 7-trifluoromethyl-5-(4-trifluoromethyl-phenyl)-pyrazolo[1,5-a]pyrimidine-3-carboxylic acid (example C.2) and 3-amino-N-pyridin-3-ylmethyl-benzenesulfonamide (example B.5) according to general procedure II. Yellow solid. MS (ISP) 619.2 [(M−H$^-$]; mp 257° C.

Example 108

7-Difluoromethyl-5-(4-trifluoromethyl-phenyl)-pyrazolo[1,5-a]pyrimidine-3-carboxylic acid{3-[(pyridin-2-ylmethyl)-sulfamoyl]-phenyl}-amide The title compound was prepared from 7-difluoromethyl-5-(4-trifluoromethyl-phenyl)-pyrazolo[1,5-a]pyrimidine-3-carboxylic acid (example C.1) and 3-amino-N-pyridin-2-ylmethyl-benzenesulfonamide (example B.6) according to general procedure II. Yellow solid. MS (ISP) 601.1 [(M−H$^-$]; mp 208° C.

Example 109

7-Trifluoromethyl-5-(4-trifluoromethyl-phenyl)-pyrazolo[1,5-a]pyrimidine-3-carboxylic acid{3-[(pyridin-2-ylmethyl)-sulfamoyl]-phenyl}-amide The title compound was prepared from 7-trifluoromethyl-5-(4-trifluoromethyl-phenyl)-pyrazolo[1,5-a]pyrimidine-3-carboxylic acid (example C.2) and 3-amino-N-pyridin-2-ylmethyl-benzenesulfonamide (example B.6) according to general procedure II. Yellow solid. MS (ISP) 619.3 [(M−H$^-$]; mp 229° C.

Example 110

7-Difluoromethyl-5-(4-trifluoromethyl-phenyl)-pyrazolo[1,5-a]pyrimidine-3-carboxylic acid[3-(2-pyridin-4-yl-ethylsulfamoyl)-phenyl]-amide The title compound was prepared from 7-difluoromethyl-5-(4-trifluoromethyl-phenyl)-pyrazolo[1,5-a]pyrimidine-3-carboxylic acid (example C.1) and 3-amino-N-(2-pyridin-4-yl-ethyl)-benzenesulfonamide (example B.7) according to general procedure II. Yellow solid. MS (ISP) 615.3 [(M−H$^-$]; mp 238° C.

Example 111

7-Trifluoromethyl-5-(4-trifluoromethyl-phenyl)-pyrazolo[1,5-a]pyrimidine-3-carboxylic acid[3-(2-pyridin-4-yl-ethylsulfamoyl)-phenyl]-amide The title compound was prepared from 7-trifluoromethyl-5-(4-trifluoromethyl-phenyl)-pyrazolo[1,5-a]pyrimidine-3-carboxylic acid (example C.2) and 3-amino-N-(2-pyridin-4-yl-ethyl)-benzenesulfonamide (example B.7) according to general procedure II. Yellow solid. MS (ISP) 633.0 [(M−H$^-$]; mp 236° C.

Example 112

7-Difluoromethyl-5-(4-trifluoromethyl-phenyl)-pyrazolo[1,5-a]pyrimidine-3-carboxylic acid[3-(2-hydroxy-1,1-dimethyl-ethylsulfamoyl)-phenyl]-amide The title compound was prepared from 7-difluoromethyl-5-(4-trifluoromethyl-phenyl)-pyrazolo[1,5-a]pyrimidine-3-carboxylic acid (example C.1) and 3-amino-N-(2-hydroxy-1,1-dimethyl-ethyl)-benzenesulfonamide (example B.8) according to general procedure II. Orange solid. MS (ISP) 582.0 [(M−H)−]; mp 232° C.

Example 113

7-Trifluoromethyl-5-(4-trifluoromethyl-phenyl)-pyrazolo[1,5-a]pyrimidine-3-carboxylic acid[3-(2-hydroxy-1,1-dimethyl-ethylsulfamoyl)-phenyl]-amide The title compound was prepared from 7-trifluoromethyl-5-(4-trifluoromethyl-phenyl)-pyrazolo[1,5-a]pyrimidine-3-carboxylic acid (example C.2) and 3-amino-N-(2-hydroxy-1,1-dimethyl-ethyl)-benzenesulfonamide (example B.8) according to general procedure II. Yellow solid. MS (ISP) 600.1 [(M−H)−]; mp 227° C.

Example 114

7-Difluoromethyl-5-(4-trifluoromethoxy-phenyl)-pyrazolo[1,5-a]pyrimidine-3-carboxylic acid(3-sulfamoyl-phenyl)-amide The title compound was prepared from 7-difluoromethyl-5-(4-trifluoromethoxy-phenyl)-pyrazolo[1,5-a]pyrimidine-3-carboxylic acid (example C.20) and 3-sulfamoyl-phenylamine [commercially available] according to general procedure II. Yellow solid. MS (ISP) 526.2 [(M−H)−]; mp 231° C.

Example 115

5-(4-Trifluoromethoxy-phenyl)-7-trifluoromethyl-pyrazolo[1,5-a]pyrimidine-3-carboxylic acid(3-sulfamoyl-phenyl)-amide The title compound was prepared from 5-(4-trifluoromethoxy-phenyl)-7-trifluoromethyl-pyrazolo[1,5-a]pyrimidine-3-carboxylic acid (example C.19) and 3-sulfamoyl-phenylamine [commercially available] according to general procedure II. Yellow solid. MS (ISP) 544.2 [(M−H)−]; mp 257° C.

Example 116

7-Difluoromethyl-5-(4-trifluoromethoxy-phenyl)-pyrazolo[1,5-a]pyrimidine-3-carboxylic acid(3-methanesulfonyl-phenyl)-amide The title compound was prepared from 7-difluoromethyl-5-(4-trifluoromethoxy-phenyl)-pyrazolo[1,5-a]pyrimidine-3-carboxylic acid (example C.20) and 3-methanesulfonyl-phenylamine [commercially available as hydrochloride] according to general procedure II. Yellow solid. MS (ISP) 527.2 [(M+H)+]; mp 223° C.

Example 117

5-(4-Trifluoromethoxy-phenyl)-7-trifluoromethyl-pyrazolo[1,5-a]pyrimidine-3-carboxylic acid(3-methanesulfonyl-phenyl)-amide The title compound was prepared from 5-(4-trifluoromethoxy-phenyl)-7-trifluoromethyl-pyrazolo[1,5-a]pyrimidine-3-carboxylic acid (example C.19) and 3-methanesulfonyl-phenylamine [commercially available as hydrochloride] according to general procedure II. Yellow solid. MS (ISP) 545.3 [(M+H)+]; mp 245° C.

Example 118

5-(3,4-Difluoro-phenyl)-7-trifluoromethyl-pyrazolo[1,5-a]pyrimidine-3-carboxylic acid(3-sulfamoyl-phenyl)-amide The title compound was prepared from 5-(3,4-difluoro-phenyl)-7-trifluoromethyl-pyrazolo[1,5-a]pyrimidine-3-carboxylic acid (example C.21) and 3-sulfamoyl-phenylamine [commercially available] according to general procedure II. Yellow solid. MS (ISP) 498.2 [(M+H)+]; mp 275° C.

Example 119

5-(3,4-Difluoro-phenyl)-7-trifluoromethyl-pyrazolo[1,5-a]pyrimidine-3-carboxylic acid(3-methanesulfonyl-phenyl)-amide The title compound was prepared from 5-(3,4-difluoro-phenyl)-7-trifluoromethyl-pyrazolo[1,5-a]pyrimidine-3-carboxylic acid (example C.21) and 3-methanesulfonyl-phenylamine [commercially available as hydrochloride] according to general procedure II. Yellow solid. MS (ISP) 497.1 [(M+H)+]; mp 256° C.

Example 120

5-(4-Chloro-phenyl)-7-trifluoromethyl-pyrazolo[1,5-a]pyrimidine-3-carboxylic acid[3-(2-hydroxy-1,1-dimethyl-ethylsulfamoyl)-phenyl]-amide The title compound was prepared from 5-(4-chloro-phenyl)-7-trifluoromethyl-pyrazolo[1,5-a]pyrimidine-3-carboxylic acid (example C.4) and 3-amino-N-(2-hydroxy-1,1-dimethyl-ethyl)-benzenesulfonamide (example B.8) according to general procedure II. Yellow solid. MS (ISP) 566.2 [(M−H)−]; mp 271° C.

Example 121

5-(3-Chloro-4-trifluoromethyl-phenyl)-7-trifluoromethyl-pyrazolo[1,5-a]pyrimidine-3-carboxylic acid[3-(2-hydroxy-1,1-dimethyl-ethylsulfamoyl)-phenyl]-amide The title compound was prepared from 5-(3-chloro-4-trifluoromethyl-phenyl)-7-trifluoromethyl-pyrazolo[1,5-a]pyrimidine-3-carboxylic acid (example C.17) and 3-amino-N-(2-hydroxy-1,1-dimethyl-ethyl)-benzenesulfonamide (example B.8) according to general procedure II. Yellow solid. MS (ISP) 634.0 [(M−H)−]; mp 251° C.

Example 122

5-[3-(2,2,2-Trifluoro-ethoxy)-4-trifluoromethyl-phenyl]-7-trifluoromethyl-pyrazolo[1,5-a]pyrimidine-3-carboxylic acid[3-(2-hydroxy-1,1-dimethyl-ethylsulfamoyl)-phenyl]-amide The title compound was prepared from 5-[3-(2,2,2-trifluoro-ethoxy)-4-trifluoromethyl-phenyl]-7-trifluoromethyl-pyrazolo[1,5-a]pyrimidine-3-carboxylic acid (example C.10) and 3-amino-N-(2-hydroxy-1,1-dimethyl-ethyl)-benzenesulfonamide (example B.8) according to general procedure II. Yellow solid. MS (ISP) 698.3 [(M−H$^-$]; mp 251° C.

Example 123

5-(3-Methyl-4-trifluoromethyl-phenyl)-7-trifluoromethyl-pyrazolo[1,5-a]pyrimidine-3-carboxylic acid [3-(2-hydroxy-1,1-dimethyl-ethylsulfamoyl)-phenyl]-amide The title compound was prepared from 5-(3-methyl-4-trifluoromethyl-phenyl)-7-trifluoromethyl-pyrazolo[1,5-a]pyrimidine-3-carboxylic acid (example C.8) and 3-amino-N-(2-hydroxy-1,1-dimethyl-ethyl)-benzenesulfonamide (example B.8) according to general procedure II. Yellow solid. MS (ISP) 614.2 [(M−H$^-$]; mp 230° C.

Example 124

5-(3-Ethoxy-4-trifluoromethyl-phenyl)-7-trifluoromethyl-pyrazolo[1,5-a]pyrimidine-3-carboxylic acid [3-(2-hydroxy-1,1-dimethyl-ethylsulfamoyl)-phenyl]-amide The title compound was prepared from 5-(3-ethoxy-4-trifluoromethyl-phenyl)-7-trifluoromethyl-pyrazolo[1,5-a]pyrimidine-3-carboxylic acid (example C.11) and 3-amino-N-(2-hydroxy-1,1-dimethyl-ethyl)-benzenesulfonamide (example B.8) according to general procedure II. Yellow solid. MS (ISP) 646.4 [(M+H$^+$]; mp 268° C.

Example 125

5-(3,4-Dichloro-phenyl)-7-trifluoromethyl-pyrazolo[1,5-a]pyrimidine-3-carboxylic acid[3-(2-hydroxy-1,1-dimethyl-ethylsulfamoyl)-phenyl]-amide The title compound was prepared from 5-(3,4-dichloro-phenyl)-7-trifluoromethyl-pyrazolo[1,5-a]pyrimidine-3-carboxylic acid (example C.9) and 3-amino-N-(2-hydroxy-1,1-dimethyl-ethyl)-benzenesulfonamide (example B.8) according to general procedure II. Light yellow solid. MS (ISP) 599.8 [(M−H$^-$]; mp 269° C.

Example 126

5-(3-Fluoro-4-trifluoromethyl-phenyl)-7-trifluoromethyl-pyrazolo[1,5-a]pyrimidine-3-carboxylic acid [3-(2-hydroxy-1,1-dimethyl-ethylsulfamoyl)-phenyl]-amide The title compound was prepared from 5-(3-fluoro-4-trifluoromethyl-phenyl)-7-trifluoromethyl-pyrazolo[1,5-a]pyrimidine-3-carboxylic acid (example C.18) and 3-amino-N-(2-hydroxy-1,1-dimethyl-ethyl)-benzenesulfonamide (example B.8) according to general procedure II. Light yellow solid. MS (ISP) 620.3 [(M+H$^+$]; mp 221° C.

Example 127

5-(4-Trifluoromethoxy-phenyl)-7-trifluoromethyl-pyrazolo[1,5-a]pyrimidine-3-carboxylic acid[3-(2-hydroxy-1,1-dimethyl-ethylsulfamoyl)-phenyl]-amide The title compound was prepared from 5-(4-trifluoromethoxy-phenyl)-7-trifluoromethyl-pyrazolo[1,5-a]pyrimidine-3-carboxylic acid (example C.19) and 3-amino-N-(2-hydroxy-1,1-dimethyl-ethyl)-benzenesulfonamide (example B.8) according to general procedure II. Yellow solid. MS (ISP) 618.3 [(M+H$^+$]; mp 212° C.

Example 128

5-(4-Chloro-phenyl)-7-difluoromethyl-pyrazolo[1,5-a]pyrimidine-3-carboxylic acid[3-(2-hydroxy-1,1-dimethyl-ethylsulfamoyl)-phenyl]-amide The title compound was prepared from 5-(4-chloro-phenyl)-7-difluoromethyl-pyrazolo[1,5-a]pyrimidine-3-carboxylic acid (example C.3) and 3-amino-N-(2-hydroxy-1,1-dimethyl-ethyl)-benzenesulfonamide (example B.8) according to general procedure II. Light yellow solid. MS (ISP) 550.1 [(M+H$^+$]; mp 229° C.

Example 129

7-Difluoromethyl-5-(3-ethoxy-4-trifluoromethyl-phenyl)-pyrazolo[1,5-a]pyrimidine-3-carboxylic acid[3-(2-hydroxy-1,1-dimethyl-ethylsulfamoyl)-phenyl]-amide The title compound was prepared from 7-difluoromethyl-5-(3-ethoxy-4-trifluoromethyl-phenyl)-pyrazolo[1,5-a]pyrimidine-3-carboxylic acid (example C.12) and 3-amino-N-(2-hydroxy-1,1-dimethyl-ethyl)-benzenesulfonamide (example B.8) according to general procedure II. Light yellow solid. MS (ISP) 626.6 [(M−H$^-$]; mp 250° C.

Example 130

7-Difluoromethyl-5-(4-trifluoromethyl-phenyl)-pyrazolo[1,5-a]pyrimidine-3-carboxylic acid(4-methyl-3-sulfamoyl-phenyl)-amide The title compound was prepared from 7-difluoromethyl-5-(4-trifluoromethyl-phenyl)-pyrazolo[1,5-a]pyrimidine-3-carboxylic acid (example C.1) and 3-amino-6-methyl-benzenesulfonamide [CAS-No. 6973-09-7] according to general procedure II. Yellow solid. MS (ISP) 526.2 [(M+H$^+$]; mp 249° C.

Example 131

7-Trifluoromethyl-5-(4-trifluoromethyl-phenyl)-pyrazolo[1,5-a]pyrimidine-3-carboxylic acid(4-methyl-3-sulfamoyl-phenyl)-amide The title compound was prepared from 7-trifluoromethyl-5-(4-trifluoromethyl-phenyl)-pyrazolo[1,5-a]pyrimidine-3-carboxylic acid (example C.2) and 3-amino-6-methyl-benzenesulfonamide [CAS-No. 6973-09-7] according to general procedure II. Yellow solid. MS (ISP) 544.0 [(M+H)$^+$]; mp 297° C.

Example 132

7-Difluoromethyl-5-(4-trifluoromethyl-phenyl)-pyrazolo[1,5-a]pyrimidine-3-carboxylic acid{3-[bis-(2-hydroxy-ethyl)-sulfamoyl]-phenyl}-amide The title compound was prepared from 7-difluoromethyl-5-(4-trifluoromethyl-phenyl)-pyrazolo[1,5-a]pyrimidine-3-carboxylic acid (example C.1) and N-(2-hydroxy-1-hydroxymethyl-1-methyl-ethyl)-3-nitro-benzenesulfonamide [CAS-No. 6374-97-6; commercially available] according to general procedure II. Yellow solid. MS (ISP) 600.4 [(M+H)$^+$]; mp 208° C.

Example 133

7-Trifluoromethyl-5-(4-trifluoromethyl-phenyl)-pyrazolo[1,5-a]pyrimidine-3-carboxylic acid{3-[bis-(2-hydroxy-ethyl)-sulfamoyl]-phenyl}-amide The title compound was prepared from 7-trifluoromethyl-5-(4-trifluoromethyl-phenyl)-pyrazolo[1,5-a]pyrimidine-3-carboxylic acid (example C.2) and N-(2-hydroxy-1-hydroxymethyl-1-methyl-ethyl)-3-nitro-benzenesulfonamide [CAS-No. 6374-97-6; commercially available] according to general procedure II. Yellow solid. MS (ISP) 618.4 [(M+H)$^+$]; mp 209° C.

Example 134

7-Difluoromethyl-5-(4-trifluoromethyl-phenyl)-pyrazolo[1,5-a]pyrimidine-3-carboxylic acid[3-(2-hydroxy-1-hydroxymethyl-1-methyl-ethylsulfamoyl)-phenyl]-amide The title compound was prepared from 7-difluoromethyl-5-(4-trifluoromethyl-phenyl)-pyrazolo[1,5-a]pyrimidine-3-carboxylic acid (example C.1) and 3-amino-N-(2-hydroxy-1-hydroxymethyl-1-methyl-ethyl)-benzenesulfonamide (example B.9) according to general procedure II. Yellow solid. MS (ISP) 600.4 [(M+H)$^+$]; mp 246° C.

Example 135

7-Trifluoromethyl-5-(4-trifluoromethyl-phenyl)-pyrazolo[1,5-a]pyrimidine-3-carboxylic acid[3-(2-hydroxy-1-hydroxymethyl-1-methyl-ethylsulfamoyl)-phenyl]-amide The title compound was prepared from 7-trifluoromethyl-5-(4-trifluoromethyl-phenyl)-pyrazolo[1,5-a]pyrimidine-3-carboxylic acid (example C.2) and 3-amino-N-(2-hydroxy-1-hydroxymethyl-1-methyl-ethyl)-benzenesulfonamide (example B.9) according to general procedure II. Yellow solid. MS (ISP) 616.2 [(M−H)$^-$]; mp 248° C.

Example 136

7-Trifluoromethyl-5-(4-trifluoromethyl-phenyl)-pyrazolo[1,5-a]pyrimidine-3-carboxylic acid(2-methyl-5-sulfamoyl-phenyl)-amide The title compound was prepared from 7-trifluoromethyl-5-(4-trifluoromethyl-phenyl)-pyrazolo[1,5-a]pyrimidine-3-carboxylic acid (example C.2) and 3-amino-4-methyl-benzenesulfonamide [CAS-No. 6274-28-8; commercially available] according to general procedure II. Yellow solid. MS (ISP) 542.1 [(M−H)$^-$]; mp 310° C.

Example 137

7-Difluoromethyl-5-(4-trifluoromethyl-phenyl)-pyrazolo[1,5-a]pyrimidine-3-carboxylic acid(2-methyl-5-sulfamoyl-phenyl)-amide The title compound was prepared from 7-difluoromethyl-5-(4-trifluoromethyl-phenyl)-pyrazolo[1,5-a]pyrimidine-3-carboxylic acid (example C.1) and 3-amino-4-methyl-benzenesulfonamide [CAS-No. 6274-28-8; commercially available] according to general procedure II. Light brown solid. MS (ISP) 524.0 [(M−H)$^-$]; mp 293° C.

Example 138

7-Trifluoromethyl-5-(4-trifluoromethyl-phenyl)-pyrazolo[1,5-a]pyrimidine-3-carboxylic acid(2-chloro-5-sulfamoyl-phenyl)-amide The title compound was prepared from 7-trifluoromethyl-5-(4-trifluoromethyl-phenyl)-pyrazolo[1,5-a]pyrimidine-3-carboxylic acid (example C.2) and 3-amino-4-chloro-benzenesulfonamide [CAS-No. 29092-34-0; commercially available] according to general procedure II. Light yellow solid. MS (ISP) 563.1 [(M−H)$^-$]; mp 300° C.

Example 139

7-Difluoromethyl-5-(4-trifluoromethyl-phenyl)-pyrazolo[1,5-a]pyrimidine-3-carboxylic acid(2-chloro-5-sulfamoyl-phenyl)-amide The title compound was prepared from 7-difluoromethyl-5-(4-trifluoromethyl-phenyl)-pyrazolo[1,5-a]pyrimidine-3-carboxylic acid (example C.1) and 3-amino-4-chloro-benzenesulfonamide [CAS-No. 29092-34-0; commercially available] according to general procedure II. Light yellow solid. MS (ISP) 545.1 [(M−H)$^-$]; mp 286° C.

Example 140

7-Trifluoromethyl-5-(4-trifluoromethyl-phenyl)-pyrazolo[1,5-a]pyrimidine-3-carboxylic acid[2-chloro-5-(2-hydroxy-1,1-dimethyl-ethylsulfamoyl)-phenyl]-amide The title compound was prepared from 7-trifluoromethyl-5-(4-trifluoromethyl-phenyl)-pyrazolo[1,5-a]pyrimidine-3-carboxylic acid (example C.2) and 3-amino-4-chloro-N-(2-hydroxy-1,1-dimethyl-ethyl)-benzenesulfonamide (example B.10) according to general procedure II. Yellow solid. MS (ISP) 634.0 [(M−H)$^-$]; mp 246° C.

Example 141

7-Difluoromethyl-5-(4-trifluoromethyl-phenyl)-pyrazolo[1,5-a]pyrimidine-3-carboxylic acid[2-chloro-5-(2-hydroxy-1,1-dimethyl-ethylsulfamoyl)-phenyl]-amide The title compound was prepared from 7-difluoromethyl-5-(4-trifluoromethyl-phenyl)-pyrazolo[1,5-a]pyrimidine-3-carboxylic acid (example C.1) and 3-amino-4-chloro-N-(2-hydroxy-1,1-dimethyl-ethyl)-benzenesulfonamide (example B.10) according to general procedure II. Light yellow solid. MS (ISP) 616.2 [(M−H⁻]; mp 234° C.

Example 142

7-Trifluoromethyl-5-(4-trifluoromethyl-phenyl)-pyrazolo[1,5-a]pyrimidine-3-carboxylic acid[5-(2-hydroxy-1,1-dimethyl-ethylsulfamoyl)-2-methyl-phenyl]-amide The title compound was prepared from 7-trifluoromethyl-5-(4-trifluoromethyl-phenyl)-pyrazolo[1,5-a]pyrimidine-3-carboxylic acid (example C.2) and 3-amino-N-(2-hydroxy-1,1-dimethyl-ethyl)-4-methyl-benzenesulfonamide (example B. 11) according to general procedure II. Yellow solid. MS (ISP) 614.2 [(M−H⁻]; mp 240° C.

Example 143

7-Difluoromethyl-5-(4-trifluoromethyl-phenyl)-pyrazolo[1,5-a]pyrimidine-3-carboxylic acid[5-(2-hydroxy-1,1-dimethyl-ethylsulfamoyl)-2-methyl-phenyl]-amide The title compound was prepared from 7-difluoromethyl-5-(4-trifluoromethyl-phenyl)-pyrazolo[1,5-a]pyrimidine-3-carboxylic acid (example C.1) and 3-amino-N-(2-hydroxy-1,1-dimethyl-ethyl)-4-methyl-benzenesulfonamide (example B.11) according to general procedure II. Light yellow solid. MS (ISP) 596.1 [(M−H⁻]; mp 214° C.

Example 144

7-Difluoromethyl-5-(4-trifluoromethyl-phenyl)-pyrazolo[1,5-a]pyrimidine-3-carboxylic acid[3-(2-dimethylamino-ethylsulfamoyl)-phenyl]-amide The title compound was prepared from 7-difluoromethyl-5-(4-trifluoromethyl-phenyl)-pyrazolo[1,5-a]pyrimidine-3-carboxylic acid (example C.1) and 3-amino-N-(2-dimethylamino-ethyl)-benzenesulfonamide (example B.12) according to general procedure II. Yellow solid. MS (ISP) 583.4 [(M+H⁺]; mp 184° C.

Example 145

7-Trifluoromethyl-5-(4-trifluoromethyl-phenyl)-pyrazolo[1,5-a]pyrimidine-3-carboxylic acid[3-(2-dimethylamino-ethylsulfamoyl)-phenyl]-amide The title compound was prepared from 7-trifluoromethyl-5-(4-trifluoromethyl-phenyl)-pyrazolo[1,5-a]pyrimidine-3-carboxylic acid (example C.2) and 3-amino-N-(2-dimethylamino-ethyl)-benzenesulfonamide (example B.12) according to general procedure II. Yellow solid. MS (ISP) 601.3 [(M+H⁺]; mp 224° C.

Example 146

5-(4-Chloro-phenyl)-7-trifluoromethyl-pyrazolo[1,5-a]pyrimidine-3-carboxylic acid[3-(1-hydroxymethyl-cyclopentylsulfamoyl)-phenyl]-amide The title compound was prepared from 5-(4-chloro-phenyl)-7-trifluoromethyl-pyrazolo[1,5-a]pyrimidine-3-carboxylic acid (example C.4) and 3-amino-N-(1-hydroxymethyl-cyclopentyl)-benzenesulfonamide (example B.13) according to general procedure II. Yellow solid. MS (ISP) 594.0 [(M+H)⁺]; mp 253-255° C.

Example 147

5-(4-Chloro-phenyl)-7-trifluoromethyl-pyrazolo[1,5-a]pyrimidine-3-carboxylic acid[3-((S)-2-hydroxymethyl-pyrrolidine-1-sulfonyl)-phenyl]-amide The title compound was prepared from 5-(4-chloro-phenyl)-7-trifluoromethyl-pyrazolo[1,5-a]pyrimidine-3-carboxylic acid (example C.4) and (S)-[1-(3-amino-benzenesulfonyl)-pyrrolidin-2-yl]-methanol (example B.14) according to general procedure II. Pale-yellow solid. MS (ISP) 580.3 [(M+H)⁺]; mp 227-229° C.

Example 148

5-(4-Chloro-phenyl)-pyrazolo[1,5-a]pyrimidine-3-carboxylic acid(3-sulfamoyl-phenyl)-amide The title compound was prepared from 5-(4-chloro-phenyl)-pyrazolo[1,5-a]pyrimidine-3-carboxylic acid (example C.22) and 3-amino-benzenesulfonamide according to general procedure II. Pale-yellow solid. MS (ISP) 428.3 [(M+H)⁺]; mp 345° C.

Example 149

5-(4-Chloro-phenyl)-pyrazolo[1,5-a]pyrimidine-3-carboxylic acid(3-methanesulfonyl-phenyl)-amide The title compound was prepared from 5-(4-chloro-phenyl)-pyrazolo[1,5-a]pyrimidine-3-carboxylic acid (example C.22) and 3-methanesulfonyl-phenylamine according to general procedure II. Pale-yellow solid. MS (ISP) 427.4 [(M+H)⁺]; mp 258-260° C.

Example 150

5-(4-Trifluoromethyl-phenyl)-pyrazolo[1,5-a]pyrimidine-3-carboxylic acid(3-sulfamoyl-phenyl)-amide The title compound was prepared from 5-(4-chloro-phenyl)-7-trifluoromethyl-pyrazolo[1,5-a]pyrimidine-3-carboxylic acid (example C.23) and 3-amino-benzenesulfonamide according to general procedure II. Pale-yellow solid. MS (ISN) 460.1[(M−H)⁻]; mp 318-320° C.

Example 151

5-(4-Trifluoromethyl-phenyl)-pyrazolo[1,5-a]pyrimidine-3-carboxylic acid(3-methanesulfonyl-phenyl)-amide The title compound was prepared from 5-(4-trifluoromethyl-phenyl)-pyrazolo[1,5-a]pyrimidine-3-carboxylic acid (example C.23) and 3-methanesulfonyl-phenylamine according to general procedure II. Pale-yellow solid. MS (ISP) 461.3 [(M+H)$^+$]; mp 254-255° C.

Example 152

5-(4-Chloro-phenyl)-7-methyl-pyrazolo[1,5-a]pyrimidine-3-carboxylic acid(3-sulfamoyl-phenyl)-amide The title compound was prepared from 5-(4-chloro-phenyl)-7-methyl-pyrazolo[1,5-a]pyrimidine-3-carboxylic acid (example C.24) and 3-amino-benzenesulfonamide according to general procedure II. Pale-yellow solid. MS (ISP) 442.4 [(M+H)$^+$]; mp 308-310° C.

Example 153

5-(4-Chloro-phenyl)-7-methyl-pyrazolo[1,5-a]pyrimidine-3-carboxylic acid(3-methanesulfonyl-phenyl)-amide The title compound was prepared from 5-(4-chloro-phenyl)-7-methyl-pyrazolo[1,5-a]pyrimidine-3-carboxylic acid (example C.24) and 3-methanesulfonyl-phenylamine according to general procedure II. Pale-yellow solid. MS (ISP) 441.3 [(M+H)$^+$]; mp 250-251° C.

Example 154

5-(4-Chloro-phenyl)-7-methyl-pyrazolo[1,5-a]pyrimidine-3-carboxylic acid[3-(2-hydroxy-1,1-dimethyl-ethylsulfamoyl)-phenyl]-amide The title compound was prepared from 5-(4-chloro-phenyl)-7-methyl-pyrazolo[1,5-a]pyrimidine-3-carboxylic acid (example C.24) and 3-amino-N-(2-hydroxy-1,1-dimethylethyl)-benzenesulfonamide (example B.8) according to general procedure II. Pale-yellow solid. MS (ISP) 514.5 [(M+H)$^+$].

Example 155

7-Methyl-5-(4-trifluoromethyl-phenyl)-pyrazolo[1,5-a]pyrimidine-3-carboxylic acid(3-sulfamoyl-phenyl)-amide The title compound was prepared from 7-methyl-5-(4-trifluoromethyl-phenyl)-pyrazolo[1,5-a]pyrimidine-3-carboxylic acid (example C.25) and 3-amino-benzenesulfonamide according to general procedure II. Pale-yellow solid. MS (ISP) 476.5 [(M+H)$^+$]; mp 270-272° C.

Example 156

7-Methyl-5-(4-trifluoromethyl-phenyl)-pyrazolo[1,5-a]pyrimidine-3-carboxylic acid(3-methanesulfonyl-phenyl)-amide The title compound was prepared from 7-methyl-5-(4-trifluoromethyl-phenyl)-pyrazolo[1,5-a]pyrimidine-3-carboxylic acid (example C.25) and 3-methanesulfonyl-phenylamine according to general procedure II. Pale-yellow solid. MS (ISP) 475.1 [(M+H)$^+$]; mp 198-200° C.

Example 157

5-(4-Chloro-phenyl)-7-ethyl-pyrazolo[1,5-a]pyrimidine-3-carboxylic acid(3-sulfamoyl-phenyl)-amide The title compound was prepared from 5-(4-chloro-phenyl)-7-ethyl-pyrazolo[1,5-a]pyrimidine-3-carboxylic acid (example C.26) and 3-amino-benzenesulfonamide according to general procedure II. Pale-yellow solid. MS (ISN) 454.3 [(M–H)$^-$]; mp 252-253° C.

Example 158

5-(4-Chloro-phenyl)-7-ethyl-pyrazolo[1,5-a]pyrimidine-3-carboxylic acid(3-methanesulfonyl-phenyl)-amide The title compound was prepared from 5-(4-chloro-phenyl)-7-ethyl-pyrazolo[1,5-a]pyrimidine-3-carboxylic acid (example C.26) and 3-methanesulfonyl-phenylamine according to general procedure II. Pale-yellow solid. MS (ISP) 455.92 [(M+H)$^+$]; mp 230-232° C.

Example 159

5-(4-Chloro-phenyl)-7-ethyl-pyrazolo[1,5-a]pyrimidine-3-carboxylic acid[3-(2-hydroxy-1,1-dimethyl-ethylsulfamoyl)-phenyl]-amide The title compound was prepared from 5-(4-chloro-phenyl)-7-ethyl-pyrazolo[1,5-a]pyrimidine-3-carboxylic acid (example C.26) and 3-amino-N-(2-hydroxy-1,1-dimethyl-ethyl)-benzenesulfonamide (example B.8) according to general procedure II. Pale-yellow solid. MS (ISP) 528.0 [(M+H)$^+$]; mp 239-240° C.

Example 160

5-(4-Chloro-phenyl)-7-propyl-pyrazolo[1,5-a]pyrimidine-3-carboxylic acid(3-sulfamoyl-phenyl)-amide The title compound was prepared from 5-(4-chloro-phenyl)-7-propyl-pyrazolo[1,5-a]pyrimidine-3-carboxylic acid (example C.27) and 3-amino-benzenesulfonamide according to general procedure II. Pale-yellow solid. MS (ISP) 470.5 [(M+H)$^+$]; mp 252-254° C.

Example 161

5-(4-Chloro-phenyl)-7-propyl-pyrazolo[1,5-a]pyrimidine-3-carboxylic acid(3-methanesulfonyl-phenyl)-amide The title compound was prepared from 5-(4-chloro-phenyl)-7-propyl-pyrazolo[1,5-a]pyrimidine-3-carboxylic acid (example C.27) and 3-methanesulfonyl-phenylamine according to general procedure II. Pale-yellow solid. MS (ISP) 469.5 [(M+H)$^+$]; mp 214-217° C.

Example 162

5-(4-Chloro-phenyl)-7-propyl-pyrazolo[1,5-a]pyrimidine-3-carboxylic acid[3-(2-hydroxy-1,1-dimethyl-ethylsulfamoyl)-phenyl]-amide The title compound was prepared from 5-(4-chloro-phenyl)-7-propyl-pyrazolo[1,5-a]pyrimidine-3-carboxylic acid (example C.27) and 3-amino-N-(2-hydroxy-1,1-dimethylethyl)-benzenesulfonamide (example B.8) according to general procedure II. Pale-yellow solid. MS (ISP) 542.3 [(M+H)+]; mp 207-208° C.

Example 163

5-(4-Chloro-phenyl)-7-cyclopropyl-pyrazolo[1,5-a]pyrimidine-3-carboxylic acid(3-sulfamoyl-phenyl)-amide The title compound was prepared from 5-(4-chloro-phenyl)-7-cyclopropyl-pyrazolo[1,5-a]pyrimidine-3-carboxylic acid (example C.28) and 3-amino-benzenesulfonamide according to general procedure II. Pale-yellow solid. MS (ISP) 468.5 [(M+H)+].

Example 164

5-(4-Chloro-phenyl)-7-cyclopropyl-pyrazolo[1,5-a]pyrimidine-3-carboxylic acid(3-methanesulfonyl-phenyl)-amide The title compound was prepared from 5-(4-chloro-phenyl)-7-cyclopropyl-pyrazolo[1,5-a]pyrimidine-3-carboxylic acid (example C.28) and 3-methanesulfonyl-phenylamine according to general procedure II. Pale-yellow solid. MS (ISP) 467.4 [(M+H)+]; mp 235-238° C.

Example 165

5-(4-Chloro-phenyl)-7-cyclopropyl-pyrazolo[1,5-a]pyrimidine-3-carboxylic acid[3-(2-hydroxy-1,1-dimethyl-ethylsulfamoyl)-phenyl]-amide The title compound was prepared from 5-(4-chloro-phenyl)-7-cyclopropyl-pyrazolo[1,5-a]pyrimidine-3-carboxylic acid (example C.28) and 3-amino-N-(2-hydroxy-1,1-dimethyl-ethyl)-benzenesulfonamide (example B.8) according to general procedure II. Pale-yellow solid. MS (ISP) 540.5 [(M+H)+].

Example 166

5-(4-Chloro-phenyl)-7-cyclopropyl-pyrazolo[1,5-a]pyrimidine-3-carboxylic acid(3-tert-butylsulfamoyl-phenyl)-amide The title compound was prepared from 5-(4-chloro-phenyl)-7-cyclopropyl-pyrazolo[1,5-a]pyrimidine-3-carboxylic acid (example C.28) and 3-amino-N-tert-butyl-benzenesulfonamide to general procedure II. Pale-yellow solid. MS (ISP) 524.5 [(M+H)+]; mp 238-239° C.

Example 167

5-(4-Chloro-phenyl)-7-cyclopropyl-pyrazolo[1,5-a]pyrimidine-3-carboxylic acid[3-((S)-2-hydroxymethyl-pyrrolidine-1-sulfonyl)-phenyl]-amide The title compound was prepared from 5-(4-chloro-phenyl)-7-cyclopropyl-pyrazolo[1,5-a]pyrimidine-3-carboxylic acid (example C.28) and (S)-[1-(3-amino-benzenesulfonyl)-pyrrolidin-2-yl]-methanol (example B.13) according to general procedure II. Pale-yellow solid. Mp 180-182° C.

Example 168

5-(4-Chloro-phenyl)-7-cyclopropyl-pyrazolo[1,5-a]pyrimidine-3-carboxylic acid[3-(1-hydroxymethyl-cyclopentylsulfamoyl)-phenyl]-amide The title compound was prepared from 5-(4-chloro-phenyl)-7-cyclopropyl-pyrazolo[1,5-a]pyrimidine-3-carboxylic acid (example C.28) and 3-amino-N-(1-hydroxymethyl-cyclopentyl)-benzenesulfonamide (example B.13) according to general procedure II. Pale-yellow solid. MS (ISP) 566.3 [(M+H)+]; mp 255-257° C.

Example 169

5-(4-Chloro-phenyl)-7-cyclopropyl-pyrazolo[1,5-a]pyrimidine-3-carboxylic acid[5-(2-hydroxy-1,1-dimethyl-ethylsulfamoyl)-2-methyl-phenyl]-amide The title compound was prepared from 5-(4-chloro-phenyl)-7-cyclopropyl-pyrazolo[1,5-a]pyrimidine-3-carboxylic acid (example C.28) and 3-amino-N-(2-hydroxy-1,1-dimethyl-ethyl)-4-methyl-benzenesulfonamide (example B.11) according to general procedure II. Pale-yellow solid. MS (ISP) 554.3 [(M+H)+].

Example 170

7-Cyclopropyl-5-(4-trifluoromethyl-phenyl)-pyrazolo[1,5-a]pyrimidine-3-carboxylic acid(3-sulfamoyl-phenyl)-amide The title compound was prepared from 7-cyclopropyl-5-(4-trifluoromethyl-phenyl)-pyrazolo[1,5-a]pyrimidine-3-carboxylic acid (example C.29) and 3-amino-benzenesulfonamide according to general procedure II. Pale-yellow solid. MS (ISP) 502.3 [(M+H)+]; mp 249-250° C.

Example 171

7-Cyclopropyl-5-(4-trifluoromethyl-phenyl)-pyrazolo[1,5-a]pyrimidine-3-carboxylic acid(3-methanesulfonyl-phenyl)-amide The title compound was prepared from 7-cyclopropyl-5-(4-trifluoromethyl-phenyl)-pyrazolo[1,5-a]pyrimidine-3-carboxylic acid (example C.29) and 3-methanesulfonyl-phenylamine according to general procedure II. Pale-yellow solid. MS (ISP) 501.3 [(M+H)+]; mp 231-234° C.

Example 172

7-Cyclopropyl-5-(4-trifluoromethyl-phenyl)-pyrazolo[1,5-a]pyrimidine-3-carboxylic acid[3-(2-hydroxy-1,1-dimethyl-ethylsulfamoyl)-phenyl]-amide The title compound was prepared from 7-cyclopropyl-5-(4-trifluoromethyl-phenyl)-pyrazolo[1,5-a]pyrimidine-3-carboxylic acid (example C.29) and 3-amino-N-(2-hydroxy-1,1-dimethyl-ethyl)-benzenesulfonamide (example B.8) according to general procedure II. Pale-yellow solid. MS (ISP) 574.5 [(M+H)+]; mp 228-230° C.

Example 173

7-Cyclopropyl-5-(4-trifluoromethyl-phenyl)-pyrazolo[1,5-a]pyrimidine-3-carboxylic acid(3-tert-butylsulfamoyl-phenyl)-amide The title compound was prepared from 7-cyclopropyl-5-(4-trifluoromethyl-phenyl)-pyrazolo[1,5-a]pyrimidine-3-carboxylic acid (example C.29) and 3-amino-N-tert-butyl-benzenesulfonamide according to general procedure II. Pale-yellow solid. MS (ISP) 558.2 [(M+H)$^+$]; mp 258-259° C.

Example 174

7-Cyclopropyl-5-(4-trifluoromethyl-phenyl)-pyrazolo[1,5-a]pyrimidine-3-carboxylic acid[5-(2-hydroxy-1,1-dimethyl-ethylsulfamoyl)-2-methyl-phenyl]-amide The title compound was prepared from 7-cyclopropyl-5-(4-trifluoromethyl-phenyl)-pyrazolo[1,5-a]pyrimidine-3-carboxylic acid (example C.29) and 3-amino-N-(2-hydroxy-1,1-dimethyl-ethyl)-4-methyl-benzenesulfonamide (example B. 11) according to general procedure II. Pale-yellow solid. Mp 232-233° C.

Example 175

7-Chloro-5-(4-chloro-phenyl)-pyrazolo[1,5-a]pyrimidine-3-carboxylic acid(3-methanesulfonyl-phenyl)-amide The title compound was prepared from 7-chloro-5-(4-chloro-phenyl)-pyrazolo[1,5-a]pyrimidine-3-carbonyl chloride and 3-methanesulfonyl-phenylamine according to general procedure II. Pale-yellow solid. MS (ISP) 461.3 [(M+H)$^+$]; mp 253-255° C.

The starting material was prepared in the following way:

7-Chloro-5-(4-chloro-phenyl)-pyrazolo[1,5-a]pyrimidine-3-carbonyl chloride

A mixture of ethyl 5-(4-chloro-phenyl)-7-hydroxy-pyrazolo[1,5-a]pyrimidine-3-carboxylate (1.59 g, 5.0 mmol) (example C.22, step a) in dimethyl sulfoxide (30 mL)/2N NaOH (10 mL) was heated to 80° C. for 1 h, a white precipitate being formed. Upon addition of water (100 mL) to the cooled mixture a clear solution was formed which was firstly washed with diethyl ether and subsequently acidified to pH 2 by the addition of 3N HCl. The white precipitate was isolated by filtration and dried to give 5-(4-chloro-phenyl)-7-hydroxy-pyrazolo[1,5-a]pyrimidine-3-carbonylic acid (1.44 g, 99%). White solid. MS (ISN) 288.0 [(M−H)$^-$]; mp 258° C.

This material was heated together with phosphorous oxychloride (4.0 mL, 0.15 mol), and N,N-dimethylaniline (0.19 mL, 2 mmol) to 100° C. for 2 h. The mixture was evaporated in vacuo and the residue was partitioned between water and dichloromethane. The organic phase was dried (Na$_2$SO$_4$) and evaporated in vacuo to give the crude title compound (1.6 g) as a pale-yellow solid.

Example 176

5-(4-Chloro-phenyl)-7-methoxy-pyrazolo[1,5-a]pyrimidine-3-carboxylic acid(3-methanesulfonyl-phenyl)-amide The title compound was prepared by stirring 7-chloro-5-(4-chloro-phenyl)-pyrazolo[1,5-a]pyrimidine-3-carboxylic acid(3-methanesulfonyl-phenyl)-amide (example 175) (46 mg) with a solution of sodium methoxide (11 mg) in methanol (1.5 mL) for 2 h at 50° C., followed by precipitation of the product by the addition of water (10 mL). Pale-yellow solid. MS (ISP) 457.5 [(M+H)$^+$]; mp 265° C.

Preparation of Pharmaceutical Compositions Comprising Compounds of the Invention:

Example I

Tablets of the following composition are produced in a conventional manner:

|  | mg/Tablet |
|---|---|
| Active ingredient | 100 |
| Powdered. lactose | 95 |
| White corn starch | 35 |
| Polyvinylpyrrolidone | 8 |
| Na carboxymethylstarch | 10 |
| Magnesium stearate | 2 |
| Tablet weight | 250 |

Example II

Tablets of the following composition are produced in a conventional manner:

|  | mg/Tablet |
|---|---|
| Active ingredient | 200 |
| Powdered. lactose | 100 |
| White corn starch | 64 |
| Polyvinylpyrrolidone | 12 |
| Na carboxymethylstarch | 20 |
| Magnesium stearate | 4 |
| Tablet weight | 400 |

Example III

Capsules of the following composition are produced:

|  | mg/Capsule |
|---|---|
| Active ingredient | 50 |
| Crystalline. lactose | 60 |
| Microcrystalline cellulose | 34 |
| Talc | 5 |
| Magnesium stearate | 1 |
| Capsule fill weight | 150 |

The active ingredient having a suitable particle size, the crystalline lactose and the microcrystalline cellulose are homogeneously mixed with one another, sieved and thereafter talc and magnesium stearate are admixed. The final mixture is filled into hard gelatine capsules of suitable size.

The invention claimed is:

1. A compound according to formula (I)

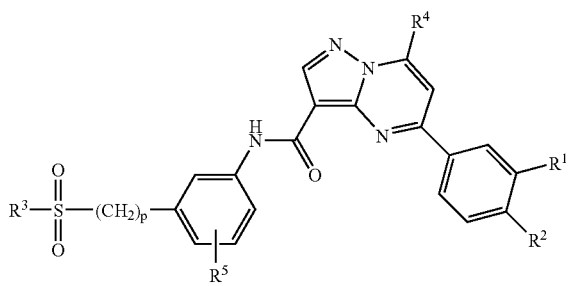

wherein
p is 0 or 1;
R¹ and R² are each independently H; halogen; lower alkyl optionally substituted by lower alkoxy; lower alkoxy optionally substituted by one or more halogen; or $CF_3$;
R³ is lower alkyl; hydroxy-lower alkyl; or $NR^aR^b$;
$R^a$ and $R^b$ are each independently selected from the group consisting of:
H;
lower alkyl optionally substituted by one or more hydroxy, fluoro, cycloalkyl, aryl, heteroaryl or $NR^cR^d$
wherein $R^c$ and $R^d$ are independently selected from H or lower alkyl;
cycloalkyl;
aryl; and
heteroaryl;
or $R^a$ and $R^b$ together with the nitrogen atom to which they are attached form an optionally substituted 5 or 6 membered heterocyclic ring;
R⁴ is H, Cl, lower alkoxy, cycloalkyl or straight lower alkyl which is optionally substituted by one or more F; and
R⁵ is H; halogen or lower alkyl;
or a pharmaceutically acceptable salt thereof;
with the exception of the compounds:
pyrazolo[1,5-a]pyrimidine-3-carboxamide, 7-(difluoromethyl)-5-(4-methylphenyl)-N-[3-(4-morpholinylsulfonyl)phenyl];
pyrazolo[1,5-a]pyrimidine-3-carboxamide, 7-(difluoromethyl)-N-[3-(4-morpholinylsulfonyl)phenyl]-5-phenyl; and
pyrazolo[1,5-a]pyrimidine-3-carboxamide, 7-(difluoromethyl)-5-(4-methoxyphenyl)-N-[3-(4-morpholinylsulphonyl)phenyl].

2. The compound of formula I in accordance with claim 1 wherein R¹ and R² are each independently selected from the group consisting of H, Cl, Me, $CF_3$, MeO, EtO and $CF_3CH_2O$—.

3. The compound of formula I in accordance with claim 1 wherein:
p is 0 or 1;
R¹ and R² are each independently selected from the group consisting of H; halogen; lower alkyl optionally substituted by lower alkoxy; lower alkoxy optionally substituted by one or more halogen; or $CF_3$;
R³ is selected from the group consisting of lower alkyl; hydroxy-lower alkyl; and $NR^aR^b$, wherein
$R^a$ and $R^b$ are each independently selected from the group consisting of:
H;
lower alkyl optionally substituted by one or more fluoro, hydroxy, cycloalkyl, aryl, heteroaryl, or $NR^cR^d$,
wherein $R^c$ and $R^d$ are each independently selected from H or lower alkyl;
cycloalkyl;
aryl; and
heteroaryl;
or $R^a$ and $R^b$ together with the nitrogen atom to which they are attached form a 4-morpholinyl; 1-pyrrolidinyl or 1-piperazinyl group;
R⁴ is H, cyclopropyl or straight lower alkyl, which is optionally substituted by one or more F; and
R⁵ is H; halogen or lower alkyl.

4. The compound of formula I in accordance with claim 3 wherein R³ is lower alkyl.

5. The compound of formula I in accordance with claim 4 wherein said compound is selected from the group consisting of:
7-Difluoromethyl-5-(4-trifluoromethyl-phenyl)-pyrazolo[1,5-a]pyrimidine-3-carboxylic acid(3-methanesulfonyl-phenyl)-amide;
7-Trifluoromethyl-5-(4-trifluoromethyl-phenyl)-pyrazolo[1,5-a]pyrimidine-3-carboxylic acid(3-methanesulfonyl-phenyl)-amide;
5-(4-Chloro-phenyl)-7-trifluoromethyl-pyrazolo[1,5-a]pyrimidine-3-carboxylic acid(3-methanesulfonyl-phenyl)-amide;
5-(3,4-Dichloro-phenyl)-7-difluoromethyl-pyrazolo[1,5-a]pyrimidine-3-carboxylic acid(3-methanesulfonyl-phenyl)-amide;
5-(3,4-Dichloro-phenyl)-7-trifluoromethyl-pyrazolo[1,5-a]pyrimidine-3-carboxylic acid(3-methanesulfonyl-phenyl)-amide;
7-Difluoromethyl-5-(3-methyl-4-trifluoromethyl-phenyl)-pyrazolo[1,5-a]pyrimidine-3-carboxylic acid(3-methanesulfonyl-phenyl)-amide;
5-(3-Methyl-4-trifluoromethyl-phenyl)-7-trifluoromethyl-pyrazolo[1,5-a]pyrimidine-3-carboxylic acid(3-methanesulfonyl-phenyl)-amide;
5-(3-Ethoxy-4-trifluoromethyl-phenyl)-7-trifluoromethyl-pyrazolo[1,5-a]pyrimidine-3-carboxylic acid(3-methanesulfonyl-phenyl)-amide;
7-Difluoromethyl-5-(3-ethoxy-4-trifluoromethyl-phenyl)-pyrazolo[1,5-a]pyrimidine-3-carboxylic acid(3-methanesulfonyl-phenyl)-amide; and
5-[3-(2,2,2-Trifluoro-ethoxy)-4-trifluoromethyl-phenyl]-7-trifluoromethyl-pyrazolo[1,5-a]pyrimidine-3-carboxylic acid(3-methanesulfonyl-phenyl)-amide.

6. The compound of formula I in accordance with claim 4 wherein said compound is selected from the group consisting of:
7-Difluoromethyl-5-[3-(2,2,2-trifluoro-ethoxy)-4-trifluoromethyl-phenyl]-pyrazolo[1,5-a]pyrimidine-3-carboxylic acid(3-methanesulfonyl-phenyl)-amide;
5-(4-Chloro-3-methyl-phenyl)-7-difluoromethyl-pyrazolo[1,5-a]pyrimidine-3-carboxylic acid(3-methanesulfonyl-phenyl)-amide;
5-(3-Fluoro-4-trifluoromethyl-phenyl)-7-trifluoromethyl-pyrazolo[1,5-a]pyrimidine-3-carboxylic acid(3-sulfamoyl-phenyl)-amide;

5-(3-Chloro-4-trifluoromethyl-phenyl)-7-difluoromethyl-pyrazolo[1,5-a]pyrimidine-3-carboxylic acid(3-methanesulfonyl-phenyl)-amide;

7-Difluoromethyl-5-(3-fluoro-4-trifluoromethyl-phenyl)-pyrazolo[1,5-a]pyrimidine-3-carboxylic acid(3-methanesulfonyl-phenyl)-amide;

5-(3-Chloro-4-trifluoromethyl-phenyl)-7-trifluoromethyl-pyrazolo[1,5-a]pyrimidine-3-carboxylic acid(3-methanesulfonyl-phenyl)-amide;

5-(3-Fluoro-4-trifluoromethyl-phenyl)-7-trifluoromethyl-pyrazolo[1,5-a]pyrimidine-3-carboxylic acid(3-methanesulfonyl-phenyl)-amide;

7-Difluoromethyl-5-(4-trifluoromethoxy-phenyl)-pyrazolo[1,5-a]pyrimidine-3-carboxylic acid(3-methanesulfonyl-phenyl)-amide;

5-(4-Trifluoromethoxy-phenyl)-7-trifluoromethyl-pyrazolo[1,5-a]pyrimidine-3-carboxylic acid(3-methanesulfonyl-phenyl)-amide; and 5-(3,4-Difluoro-phenyl)-7-trifluoromethyl-pyrazolo[1,5-a]pyrimidine-3-carboxylic acid(3-methanesulfonyl-phenyl)-amide.

7. The compound of formula I in accordance with claim 1 wherein said compound is selected from the group consisting of:

5-(4-Chloro-phenyl)-pyrazolo[1,5-a]pyrimidine-3-carboxylic acid(3-methanesulfonyl-phenyl)-amide;

5-(4-Trifluoromethyl-phenyl)-pyrazolo[1,5-a]pyrimidine-3-carboxylic acid(3-methanesulfonyl-phenyl)-amide;

5-(4-Chloro-phenyl)-7-methyl-pyrazolo[1,5-a]pyrimidine-3-carboxylic acid(3-methanesulfonyl-phenyl)-amide;

7-Methyl-5-(4-trifluoromethyl-phenyl)-pyrazolo[1,5-a]pyrimidine-3-carboxylic acid (3-methanesulfonyl-phenyl)-amide;

5-(4-Chloro-phenyl)-7-ethyl-pyrazolo[1,5-a]pyrimidine-3-carboxylic acid(3-methanesulfonyl-phenyl)-amide;

5-(4-Chloro-phenyl)-7-propyl-pyrazolo[1,5-a]pyrimidine-3-carboxylic acid(3-methanesulfonyl-phenyl)-amide;

5-(4-Chloro-phenyl)-7-cyclopropyl-pyrazolo[1,5-a]pyrimidine-3-carboxylic acid(3-methanesulfonyl-phenyl)-amide;

7-Cyclopropyl-5-(4-trifluoromethyl-phenyl)-pyrazolo[1,5-a]pyrimidine-3-carboxylic acid(3-methanesulfonyl-phenyl)-amide;

7-Chloro-5-(4-chloro-phenyl)-pyrazolo[1,5-a]pyrimidine-3-carboxylic acid(3-methanesulfonyl-phenyl)-amide; and 5-(4-Chloro-phenyl)-7-methoxy-pyrazolo[1,5-a]pyrimidine-3-carboxylic acid(3-methanesulfonyl-phenyl)-amide.

8. The compound of formula I in accordance with claim 3 wherein $R^3$ is hydroxy-lower alkyl.

9. The compound of formula I in accordance with claim 1 wherein said compound is selected from the group consisting of:

7-Trifluoromethyl-5-(4-trifluoromethyl-phenyl)-pyrazolo[1,5-a]pyrimidine-3-carboxylic acid(3-sulfamoylmethyl-phenyl)-amide; and 7-Difluoromethyl-5-(4-trifluoromethyl-phenyl)-pyrazolo[1,5-a]pyrimidine-3-carboxylic acid(3-sulfamoylmethyl-phenyl)-amide.

10. The compound of formula I in accordance with claim 3 wherein $R^3$ is $NR^aR^b$; wherein $R^a$ and $R^b$ are independently selected from:

H;

lower alkyl optionally substituted by one or more hydroxy, fluoro, cycloalkyl, aryl, heteroaryl or $NR^cR^d$, wherein $R^c$ and $R^d$ are independently selected from H or lower alkyl;

cycloalkyl;

aryl; and heteroaryl.

11. The compound of formula I in accordance with claim 10 wherein said compound is selected from the group consisting of:

7-Trifluoromethyl-5-(4-trifluoromethyl-phenyl)-pyrazolo[1,5-a]pyrimidine-3-carboxylic acid(3-sulfamoyl-phenyl)-amide;

5-(3-Ethoxy-4-trifluoromethyl-phenyl)-7-trifluoromethyl-pyrazolo[1,5-a]pyrimidine-3-carboxylic acid(3-sulfamoyl-phenyl)-amide;

7-Difluoromethyl-5-(3-ethoxy-4-trifluoromethyl-phenyl)-pyrazolo[1,5-a]pyrimidine-3-carboxylic acid(3-sulfamoyl-phenyl)-amide;

7-Difluoromethyl-5-(3-methyl-4-trifluoromethyl-phenyl)-pyrazolo[1,5-a]pyrimidine-3-carboxylic acid(3-sulfamoyl-phenyl)-amide;

5-(3-Methyl-4-trifluoromethyl-phenyl)-7-trifluoromethyl-pyrazolo[1,5-a]pyrimidine-3-carboxylic acid(3-sulfamoyl-phenyl)-amide;

5-(3,4-Dichloro-phenyl)-7-difluoromethyl-pyrazolo[1,5-a]pyrimidine-3-carboxylic acid(3-sulfamoyl-phenyl)-amide;

5-(3,4-Dichloro-phenyl)-7-trifluoromethyl-pyrazolo[1,5-a]pyrimidine-3-carboxylic acid(3-sulfamoyl-phenyl)-amide;

5-(4-Chloro-phenyl)-7-difluoromethyl-pyrazolo[1,5-a]pyrimidine-3-carboxylic acid(3-sulfamoyl-phenyl)-amide;

5-(4-Chloro-3-methyl-phenyl)-7-trifluoromethyl-pyrazolo[1,5-a]pyrimidine-3-carboxylic acid(3-sulfamoyl-phenyl)-amide; and 7-Difluoromethyl-5-(4-trifluoromethyl-phenyl)-pyrazolo[1,5-a]pyrimidine-3-carboxylic acid(3-sulfamoyl-phenyl)-amide.

12. The compound of formula I in accordance with claim 1 wherein said compound is selected from the group consisting of:

5-(4-Chloro-phenyl)-7-trifluoromethyl-pyrazolo[1,5-a]pyrimidine-3-carboxylic acid(3-sulfamoyl-phenyl)-amide;

5-[3-(2,2,2-Trifluoro-ethoxy)-4-trifluoromethyl-phenyl]-7-trifluoromethyl-pyrazolo[1,5-a]pyrimidine-3-carboxylic acid(3-sulfamoyl-phenyl)-amide;

7-Difluoromethyl-5-[3-(2,2,2-trifluoro-ethoxy)-4-trifluoromethyl-phenyl]-pyrazolo[1,5-a]pyrimidine-3-carboxylic acid(3-sulfamoyl-phenyl)-amide;

5-(4-Chloro-3-methyl-phenyl)-7-difluoromethyl-pyrazolo[1,5-a]pyrimidine-3-carboxylic acid(3-sulfamoyl-phenyl)-amide;

7-Trifluoromethyl-5-(4-trifluoromethyl-phenyl)-pyrazolo[1,5-a]pyrimidine-3-carboxylic acid[3-(2-hydroxy-ethanesulfonyl)-phenyl]-amide;

7-Difluoromethyl-5-(4-trifluoromethyl-phenyl)-pyrazolo[1,5-a]pyrimidine-3-carboxylic acid[3-(2-hydroxy-ethanesulfonyl)-phenyl]-amide;

7-Trifluoromethyl-5-(4-trifluoromethyl-phenyl)-pyrazolo[1,5-a]pyrimidine-3-carboxylic acid(3-ethylsulfamoyl-phenyl)-amide;

7-Trifluoromethyl-5-(4-trifluoromethyl-phenyl)-pyrazolo[1,5-a]pyrimidine-3-carboxylic acid(3-dimethylsulfamoyl-phenyl)-amide;

5-(4-Chloro-3-methyl-phenyl)-7-trifluoromethyl-pyrazolo[1,5-a]pyrimidine-3-carboxylic acid[3-(4-methyl-piperazine-1-sulfonyl)-phenyl]-amide; and 7-Difluoromethyl-5-(4-trifluoromethyl-phenyl)-pyrazolo[1,5-a]pyrimidine-3-carboxylic acid(3-ethylsulfamoyl-phenyl)-amide.

13. The compound of formula I in accordance with claim 10 wherein said compound is selected from the group consisting of:

7-Difluoromethyl-5-(4-trifluoromethyl-phenyl)-pyrazolo[1,5-a]pyrimidine-3-carboxylic acid(3-dimethylsulfamoyl-phenyl)-amide;

7-Difluoromethyl-5-(4-trifluoromethyl-phenyl)-pyrazolo[1,5-a]pyrimidine-3-carboxylic acid(3-methylsulfamoyl-phenyl)-amide;

7-Difluoromethyl-5-(4-trifluoromethyl-phenyl)-pyrazolo[1,5-a]pyrimidine-3-carboxylic acid(3-cyclopropylsulfamoyl-phenyl)-amide;

7-Difluoromethyl-5-(4-trifluoromethyl-phenyl)-pyrazolo[1,5-a]pyrimidine-3-carboxylic acid(3-isopropylsulfamoyl-phenyl)-amide;

7-Trifluoromethyl-5-(4-trifluoromethyl-phenyl)-pyrazolo[1,5-a]pyrimidine-3-carboxylic acid(3-methylsulfamoyl-phenyl)-amide;

7-Trifluoromethyl-5-(4-trifluoromethyl-phenyl)-pyrazolo[1,5-a]pyrimidine-3-carboxylic acid(3-isopropylsulfamoyl-phenyl)-amide;

7-Difluoromethyl-5-(4-trifluoromethyl-phenyl)-pyrazolo[1,5-a]pyrimidine-3-carboxylic acid[3-(2,2,2-trifluoro-ethylsulfamoyl)-phenyl]-amide;

7-Trifluoromethyl-5-(4-trifluoromethyl-phenyl)-pyrazolo[1,5-a]pyrimidine-3-carboxylic acid[3-(2,2,2-trifluoro-ethylsulfamoyl)-phenyl]-amide;

5-(3-Methyl-4-trifluoromethyl-phenyl)-7-trifluoromethyl-pyrazolo[1,5-a]pyrimidine-3-carboxylic acid(3-cyclopropylsulfamoyl-phenyl)-amide; and 5-(3,4-Dichloro-phenyl)-7-trifluoromethyl-pyrazolo[1,5-a]pyrimidine-3-carboxylic acid(3-cyclopropylsulfamoyl-phenyl)-amide.

14. The compound of formula I in accordance with claim 10 wherein said compound is selected from the group consisting of:

5-(4-Chloro-phenyl)-7-trifluoromethyl-pyrazolo[1,5-a]pyrimidine-3-carboxylic acid(3-cyclopropylsulfamoyl-phenyl)-amide;

5-(4-Chloro-3-methyl-phenyl)-7-trifluoromethyl-pyrazolo[1,5-a]pyrimidine-3-carboxylic acid(3-cyclopropylsulfamoyl-phenyl)-amide;

7-Difluoromethyl-5-(3-methyl-4-trifluoromethyl-phenyl)-pyrazolo[1,5-a]pyrimidine-3-carboxylic acid(3-cyclopropylsulfamoyl-phenyl)-amide;

5-(3,4-Dichloro-phenyl)-7-difluoromethyl-pyrazolo[1,5-a]pyrimidine-3-carboxylic acid(3-cyclopropylsulfamoyl-phenyl)-amide;

5-(4-Chloro-phenyl)-7-difluoromethyl-pyrazolo[1,5-a]pyrimidine-3-carboxylic acid(3-cyclopropylsulfamoyl-phenyl)-amide;

7-Trifluoromethyl-5-(4-trifluoromethyl-phenyl)-pyrazolo[1,5-a]pyrimidine-3-carboxylic acid(3-isobutylsulfamoyl-phenyl)-amide;

7-Difluoromethyl-5-(4-trifluoromethyl-phenyl)-pyrazolo[1,5-a]pyrimidine-3-carboxylic acid[3-(cyclopropylmethyl-sulfamoyl)-phenyl]-amide;

7-Difluoromethyl-5-(3-ethoxy-4-trifluoromethyl-phenyl)-pyrazolo[1,5-a]pyrimidine-3-carboxylic acid(3-cyclopropylsulfamoyl-phenyl)-amide;

5-(3-Ethoxy-4-trifluoromethyl-phenyl)-7-trifluoromethyl-pyrazolo[1,5-a]pyrimidine-3-carboxylic acid(3-cyclopropylsulfamoyl-phenyl)-amide; and 7-Difluoromethyl-5-(4-trifluoromethyl-phenyl)-pyrazolo[1,5-a]pyrimidine-3-carboxylic acid(3-isobutylsulfamoyl-phenyl)-amide.

15. The compound of formula I in accordance with claim 1 wherein said compound is selected from the group consisting of:

7-Difluoromethyl-5-(4-trifluoromethyl-phenyl)-pyrazolo[1,5-a]pyrimidine-3-carboxylic acid[3-(cyclopropylmethyl-sulfamoyl)-phenyl]-amide;

7-Difluoromethyl-5-(4-trifluoromethyl-phenyl)-pyrazolo[1,5-a]pyrimidine-3-carboxylic acid(3-benzylsulfamoyl-phenyl)-amide;

7-Trifluoromethyl-5-(4-trifluoromethyl-phenyl)-pyrazolo[1,5-a]pyrimidine-3-carboxylic acid(3-phenylsulfamoyl-phenyl)-amide;

7-Trifluoromethyl-5-(4-trifluoromethyl-phenyl)-pyrazolo[1,5-a]pyrimidine-3-carboxylic acid(3-benzylsulfamoyl-phenyl)-amide;

7-Trifluoromethyl-5-(4-trifluoromethyl-phenyl)-pyrazolo[1,5-a]pyrimidine-3-carboxylic acid[3-(2-hydroxy-ethylsulfamoyl)-phenyl]-amide;

7-Difluoromethyl-5-(4-trifluoromethyl-phenyl)-pyrazolo[1,5-a]pyrimidine-3-carboxylic acid[3-(2-hydroxy-ethylsulfamoyl)-phenyl]-amide;

7-Trifluoromethyl-5-(4-trifluoromethyl-phenyl)-pyrazolo[1,5-a]pyrimidine-3-carboxylic acid(3-trifluoromethanesulfonyl-phenyl)-amide;

7-Difluoromethyl-5-(4-trifluoromethyl-phenyl)-pyrazolo[1,5-a]pyrimidine-3-carboxylic acid(3-trifluoromethanesulfonyl-phenyl)-amide;

7-Difluoromethyl-5-(4-trifluoromethyl-phenyl)-pyrazolo[1,5-a]pyrimidine-3-carboxylic acid[3-(2,2-dimethyl-propylsulfamoyl)-phenyl]-amide; and 7-Difluoromethyl-5-(4-trifluoromethyl-phenyl)-pyrazolo[1,5-a]pyrimidine-3-carboxylic acid(3-tert-butylsulfamoyl-phenyl)-amide.

16. The compound of formula I in accordance with claim 10 wherein said compound is selected from the group consisting of:

7-Trifluoromethyl-5-(4-trifluoromethyl-phenyl)-pyrazolo[1,5-a]pyrimidine-3-carboxylic acid[3-(2,2-dimethyl-propylsulfamoyl)-phenyl]-amide;

7-Trifluoromethyl-5-(4-trifluoromethyl-phenyl)-pyrazolo[1,5-a]pyrimidine-3-carboxylic acid(3-tert-butylsulfamoyl-phenyl)-amide;

5-(3-Chloro-4-trifluoromethyl-phenyl)-7-difluoromethyl-pyrazolo[1,5-a]pyrimidine-3-carboxylic acid(3-sulfamoyl-phenyl)-amide;

7-Difluoromethyl-5-(3-fluoro-4-trifluoromethyl-phenyl)-pyrazolo[1,5-a]pyrimidine-3-carboxylic acid(3-sulfamoyl-phenyl)-amide;

5-(3-Chloro-4-trifluoromethyl-phenyl)-7-trifluoromethyl-pyrazolo[1,5-a]pyrimidine-3-carboxylic acid(3-sulfamoyl-phenyl)-amide;

7-Difluoromethyl-5-(4-trifluoromethyl-phenyl)-pyrazolo[1,5-a]pyrimidine-3-carboxylic acid{3-[(pyridin-3-ylmethyl)-sulfamoyl]-phenyl}-amide;

7-Trifluoromethyl-5-(4-trifluoromethyl-phenyl)-pyrazolo[1,5-a]pyrimidine-3-carboxylic acid{3-[(pyridin-3-ylmethyl)-sulfamoyl]-phenyl}-amide;

7-Difluoromethyl-5-(4-trifluoromethyl-phenyl)-pyrazolo[1,5-a]pyrimidine-3-carboxylic acid{3-[(pyridin-2-ylmethyl)-sulfamoyl]-phenyl}-amide;

7-Trifluoromethyl-5-(4-trifluoromethyl-phenyl)-pyrazolo[1,5-a]pyrimidine-3-carboxylic acid{3-[(pyridin-2-ylmethyl)-sulfamoyl]-phenyl}-amide; and 7-Difluoromethyl-5-(4-trifluoromethyl-phenyl)-pyrazolo[1,5-a]pyrimidine-3-carboxylic acid[3-(2-pyridin-4-yl-ethylsulfamoyl)-phenyl]-amide.

17. The compound of formula I in accordance with claim 10 wherein said compound is selected from the group consisting of:

7-Trifluoromethyl-5-(4-trifluoromethyl-phenyl)-pyrazolo[1,5-a]pyrimidine-3-carboxylic acid[3-(2-pyridin-4-yl-ethylsulfamoyl)-phenyl]-amide;

7-Difluoromethyl-5-(4-trifluoromethyl-phenyl)-pyrazolo[1,5-a]pyrimidine-3-carboxylic acid[3-(2-hydroxy-1,1-dimethyl-ethylsulfamoyl)-phenyl]-amide;

7-Trifluoromethyl-5-(4-trifluoromethyl-phenyl)-pyrazolo[1,5-a]pyrimidine-3-carboxylic acid[3-(2-hydroxy-1,1-dimethyl-ethylsulfamoyl)-phenyl]-amide;

7-Difluoromethyl-5-(4-trifluoromethoxy-phenyl)-pyrazolo[1,5-a]pyrimidine-3-carboxylic acid(3-sulfamoyl-phenyl)-amide;

5-(4-Trifluoromethoxy-phenyl)-7-trifluoromethyl-pyrazolo[1,5-a]pyrimidine-3-carboxylic acid(3-sulfamoyl-phenyl)-amide;

5-(3,4-Difluoro-phenyl)-7-trifluoromethyl-pyrazolo[1,5-a]pyrimidine-3-carboxylic acid(3-sulfamoyl-phenyl)-amide;

5-(4-Chloro-phenyl)-7-trifluoromethyl-pyrazolo[1,5-a]pyrimidine-3-carboxylic acid[3-(2-hydroxy-1,1-dimethyl-ethylsulfamoyl)-phenyl]-amide;

5-(3-Chloro-4-trifluoromethyl-phenyl)-7-trifluoromethyl-pyrazolo[1,5-a]pyrimidine-3-carboxylic acid[3-(2-hydroxy-1,1-dimethyl-ethylsulfamoyl)-phenyl]-amide;

5-[3-(2,2,2-Trifluoro-ethoxy)-4-trifluoromethyl-phenyl]-7-trifluoromethyl-pyrazolo[1,5-a]pyrimidine-3-carboxylic acid[3-(2-hydroxy-1,1-dimethyl-ethylsulfamoyl)-phenyl]-amide; and 5-(3-Methyl-4-trifluoromethyl-phenyl)-7-trifluoromethyl-pyrazolo[1,5-a]pyrimidine-3-carboxylic acid[3-(2-hydroxy-1,1-dimethyl-ethylsulfamoyl)-phenyl]-amide.

18. The compound of formula I in accordance with claim 10 wherein said compound is selected from the group consisting of:

5-(3-Ethoxy-4-trifluoromethyl-phenyl)-7-trifluoromethyl-pyrazolo[1,5-a]pyrimidine-3-carboxylic acid[3-(2-hydroxy-1,1-dimethyl-ethylsulfamoyl)-phenyl]-amide;

5-(3,4-Dichloro-phenyl)-7-trifluoromethyl-pyrazolo[1,5-a]pyrimidine-3-carboxylic acid[3-(2-hydroxy-1,1-dimethyl-ethylsulfamoyl)-phenyl]-amide;

5-(3-Fluoro-4-trifluoromethyl-phenyl)-7-trifluoromethyl-pyrazolo[1,5-a]pyrimidine-3-carboxylic acid[3-(2-hydroxy-1,1-dimethyl-ethylsulfamoyl)-phenyl]-amide;

5-(4-Trifluoromethoxy-phenyl)-7-trifluoromethyl-pyrazolo[1,5-a]pyrimidine-3-carboxylic acid[3-(2-hydroxy-1,1-dimethyl-ethylsulfamoyl)-phenyl]-amide;

5-(4-Chloro-phenyl)-7-difluoromethyl-pyrazolo[1,5-a]pyrimidine-3-carboxylic acid[3-(2-hydroxy-1,1-dimethyl-ethylsulfamoyl)-phenyl]-amide;

7-Difluoromethyl-5-(3-ethoxy-4-trifluoromethyl-phenyl)-pyrazolo[1,5-a]pyrimidine-3-carboxylic acid[3-(2-hydroxy-1,1-dimethyl-ethylsulfamoyl)-phenyl]-amide;

7-Difluoromethyl-5-(4-trifluoromethyl-phenyl)-pyrazolo[1,5-a]pyrimidine-3-carboxylic acid(4-methyl-3-sulfamoyl-phenyl)-amide;

7-Trifluoromethyl-5-(4-trifluoromethyl-phenyl)-pyrazolo[1,5-a]pyrimidine-3-carboxylic acid(4-methyl-3-sulfamoyl-phenyl)-amide;

7-Difluoromethyl-5-(4-trifluoromethyl-phenyl)-pyrazolo[1,5-a]pyrimidine-3-carboxylic acid{3-[bis-(2-hydroxy-ethyl)-sulfamoyl]-phenyl}-amide; and 7-Trifluoromethyl-5-(4-trifluoromethyl-phenyl)-pyrazolo[1,5-a]pyrimidine-3-carboxylic acid{3-[bis-(2-hydroxy-ethyl)-sulfamoyl]-phenyl}-amide.

19. The compound of formula I in accordance with claim 10 wherein said compound is selected from the group consisting of:

7-Difluoromethyl-5-(4-trifluoromethyl-phenyl)-pyrazolo[1,5-a]pyrimidine-3-carboxylic acid[3-(2-hydroxy-1-hydroxymethyl-1-methyl-ethylsulfamoyl)-phenyl]-amide;

7-Trifluoromethyl-5-(4-trifluoromethyl-phenyl)-pyrazolo[1,5-a]pyrimidine-3-carboxylic acid[3-(2-hydroxy-1-hydroxymethyl-1-methyl-ethylsulfamoyl)-phenyl]-amide;

7-Trifluoromethyl-5-(4-trifluoromethyl-phenyl)-pyrazolo[1,5-a]pyrimidine-3-carboxylic acid(2-methyl-5-sulfamoyl-phenyl)-amide;

7-Difluoromethyl-5-(4-trifluoromethyl-phenyl)-pyrazolo[1,5-a]pyrimidine-3-carboxylic acid(2-methyl-5-sulfamoyl-phenyl)-amide;

7-Trifluoromethyl-5-(4-trifluoromethyl-phenyl)-pyrazolo[1,5-a]pyrimidine-3-carboxylic acid(2-chloro-5-sulfamoyl-phenyl)-amide;

7-Difluoromethyl-5-(4-trifluoromethyl-phenyl)-pyrazolo[1,5-a]pyrimidine-3-carboxylic acid(2-chloro-5-sulfamoyl-phenyl)-amide;

7-Trifluoromethyl-5-(4-trifluoromethyl-phenyl)-pyrazolo[1,5-a]pyrimidine-3-carboxylic acid[2-chloro-5-(2-hydroxy-1,1-dimethyl-ethylsulfamoyl)-phenyl]-amide;

7-Difluoromethyl-5-(4-trifluoromethyl-phenyl)-pyrazolo[1,5-a]pyrimidine-3-carboxylic acid[2-chloro-5-(2-hydroxy-1,1-dimethyl-ethylsulfamoyl)-phenyl]-amide;

7-Trifluoromethyl-5-(4-trifluoromethyl-phenyl)-pyrazolo[1,5-a]pyrimidine-3-carboxylic acid[5-(2-hydroxy-1,1-dimethyl-ethylsulfamoyl)-2-methyl-phenyl]-amide; and 7-Difluoromethyl-5-(4-trifluoromethyl-phenyl)-pyrazolo[1,5-a]pyrimidine-3-carboxylic acid[5-(2-hydroxy-1,1-dimethyl-ethylsulfamoyl)-2-methyl-phenyl]-amide.

20. The compound of formula I in accordance with claim 10 wherein said compound is selected from the group consisting of:

7-Difluoromethyl-5-(4-trifluoromethyl-phenyl)-pyrazolo[1,5-a]pyrimidine-3-carboxylic acid[3-(2-dimethylamino-ethylsulfamoyl)-phenyl]-amide;

7-Trifluoromethyl-5-(4-trifluoromethyl-phenyl)-pyrazolo[1,5-a]pyrimidine-3-carboxylic acid[3-(2-dimethylamino-ethylsulfamoyl)-phenyl]-amide;

5-(4-Chloro-phenyl)-7-trifluoromethyl-pyrazolo[1,5-a]pyrimidine-3-carboxylic acid[3-(1-hydroxymethyl-cyclopentylsulfamoyl)-phenyl]-amide;

5-(4-Chloro-phenyl)-pyrazolo[1,5-a]pyrimidine-3-carboxylic acid(3-sulfamoyl-phenyl)-amide;

5-(4-Trifluoromethyl-phenyl)-pyrazolo[1,5-a]pyrimidine-3-carboxylic acid(3-sulfamoyl-phenyl)-amide;

5-(4-Chloro-phenyl)-7-methyl-pyrazolo[1,5-a]pyrimidine-3-carboxylic acid(3-sulfamoyl-phenyl)-amide;

5-(4-Chloro-phenyl)-7-methyl-pyrazolo[1,5-a]pyrimidine-3-carboxylic acid[3-(2-hydroxy-1,1-dimethyl-ethylsulfamoyl)-phenyl]-amide;

7-Methyl-5-(4-trifluoromethyl-phenyl)-pyrazolo[1,5-a]pyrimidine-3-carboxylic acid(3-sulfamoyl-phenyl)-amide;

5-(4-Chloro-phenyl)-7-ethyl-pyrazolo[1,5-a]pyrimidine-3-carboxylic acid(3-sulfamoyl-phenyl)-amide; and 5-(4-Chloro-phenyl)-7-ethyl-pyrazolo[1,5-a]pyrimidine-3-carboxylic acid[3-(2-hydroxy-1,1-dimethyl-ethylsulfamoyl)-phenyl]-amide.

21. The compound of formula I in accordance with claim 10 wherein said compound is selected from the group consisting of:

5-(4-Chloro-phenyl)-7-propyl-pyrazolo[1,5-a]pyrimidine-3-carboxylic acid(3-sulfamoyl-phenyl)-amide;

5-(4-Chloro-phenyl)-7-propyl-pyrazolo[1,5-a]pyrimidine-3-carboxylic acid[3-(2-hydroxy-1,1-dimethyl-ethylsulfamoyl)-phenyl]-amide;

5-(4-Chloro-phenyl)-7-cyclopropyl-pyrazolo[1,5-a]pyrimidine-3-carboxylic acid(3-sulfamoyl-phenyl)-amide;

5-(4-Chloro-phenyl)-7-cyclopropyl-pyrazolo[1,5-a]pyrimidine-3-carboxylic acid[3-(2-hydroxy-1,1-dimethyl-ethylsulfamoyl)-phenyl]-amide;

5-(4-Chloro-phenyl)-7-cyclopropyl-pyrazolo[1,5-a]pyrimidine-3-carboxylic acid(3-tert-butylsulfamoyl-phenyl)-amide;

5-(4-Chloro-phenyl)-7-cyclopropyl-pyrazolo[1,5-a]pyrimidine-3-carboxylic acid[3-(1-hydroxymethyl-cyclopentylsulfamoyl)-phenyl]-amide;

5-(4-Chloro-phenyl)-7-cyclopropyl-pyrazolo[1,5-a]pyrimidine-3-carboxylic acid[5-(2-hydroxy-1,1-dimethyl-ethylsulfamoyl)-2-methyl-phenyl]-amide;

7-Cyclopropyl-5-(4-trifluoromethyl-phenyl)-pyrazolo[1,5-a]pyrimidine-3-carboxylic acid(3-sulfamoyl-phenyl)-amide;

7-Cyclopropyl-5-(4-trifluoromethyl-phenyl)-pyrazolo[1,5-a]pyrimidine-3-carboxylic acid[3-(2-hydroxy-1,1-dimethyl-ethylsulfamoyl)-phenyl]-amide;

7-Cyclopropyl-5-(4-trifluoromethyl-phenyl)-pyrazolo[1,5-a]pyrimidine-3-carboxylic acid(3-tert-butylsulfamoyl-phenyl)-amide; and 7-Cyclopropyl-5-(4-trifluoromethyl-phenyl)-pyrazolo[1,5-a]pyrimidine-3-carboxylic acid[5-(2-hydroxy-1,1-dimethyl-ethylsulfamoyl)-2-methyl-phenyl]-amide.

22. The compound of formula I in accordance with claim 3 wherein $R^3$ is 4-morpholinyl.

23. The compound of formula I in accordance with claim 22 wherein said compound is selected from the group consisting of:

7-Trifluoromethyl-5-(4-trifluoromethyl-phenyl)-pyrazolo[1,5-a]pyrimidine-3-carboxylic acid[3-(morpholine-4-sulfonyl)-phenyl]-amide;

7-Difluoromethyl-5-(4-trifluoromethyl-phenyl)-pyrazolo[1,5-a]pyrimidine-3-carboxylic acid[3-(morpholine-4-sulfonyl)-phenyl]-amide;

5-(4-Chloro-phenyl)-7-difluoromethyl-pyrazolo[1,5-a]pyrimidine-3-carboxylic acid[3-(morpholine-4-sulfonyl)-phenyl]-amide;

5-(4-Chloro-phenyl)-7-trifluoromethyl-pyrazolo[1,5-a]pyrimidine-3-carboxylic acid[3-(morpholine-4-sulfonyl)-phenyl]-amide;

7-Difluoromethyl-5-(3-methyl-4-trifluoromethyl-phenyl)-pyrazolo[1,5-a]pyrimidine-3-carboxylic acid[3-(morpholine-4-sulfonyl)-phenyl]-amide;

5-(4-Chloro-3-methyl-phenyl)-7-trifluoromethyl-pyrazolo[1,5-a]pyrimidine-3-carboxylic acid[3-(morpholine-4-sulfonyl)-phenyl]-amide;

5-(3,4-Dichloro-phenyl)-7-difluoromethyl-pyrazolo[1,5-a]pyrimidine-3-carboxylic acid[3-(morpholine-4-sulfonyl)-phenyl]-amide;

5-(3,4-Dichloro-phenyl)-7-trifluoromethyl-pyrazolo[1,5-a]pyrimidine-3-carboxylic acid[3-(morpholine-4-sulfonyl)-phenyl]-amide;

5-(3-Methyl-4-trifluoromethyl-phenyl)-7-trifluoromethyl-pyrazolo[1,5-a]pyrimidine-3-carboxylic acid[3-(morpholine-4-sulfonyl)-phenyl]-amide; and 5-(3-Ethoxy-4-trifluoromethyl-phenyl)-7-trifluoromethyl-pyrazolo[1,5-a]pyrimidine-3-carboxylic acid[3-(morpholine-4-sulfonyl)-phenyl]-amide.

24. The compound of formula I in accordance with claim 3 wherein $R^3$ is pyrrolidine.

25. The compound of formula I in accordance with claim 24 wherein said compound is selected from the group consisting of:

7-Trifluoromethyl-5-(4-trifluoromethyl-phenyl)-pyrazolo[1,5-a]pyrimidine-3-carboxylic acid[3-(pyrrolidine-1-sulfonyl)-phenyl]-amide;

5-(4-Chloro-phenyl)-7-trifluoromethyl-pyrazolo[1,5-a]pyrimidine-3-carboxylic acid[3-(pyrrolidine-1-sulfonyl)-phenyl]-amide;

7-Difluoromethyl-5-(3-methyl-4-trifluoromethyl-phenyl)-pyrazolo[1,5-a]pyrimidine-3-carboxylic acid[3-(pyrrolidine-1-sulfonyl)-phenyl]-amide;

5-(4-Chloro-3-methyl-phenyl)-7-trifluoromethyl-pyrazolo[1,5-a]pyrimidine-3-carboxylic acid[3-(pyrrolidine-1-sulfonyl)-phenyl]-amide;

5-(4-Chloro-phenyl)-7-trifluoromethyl-pyrazolo[1,5-a]pyrimidine-3-carboxylic acid[3-((S)-2-hydroxymethyl-pyrrolidine-1-sulfonyl)-phenyl]-amide; and 5-(4-Chloro-phenyl)-7-cyclopropyl-pyrazolo[1,5-a]pyrimidine-3-carboxylic acid[3-((S)-2-hydroxymethyl-pyrrolidine-1-sulfonyl)-phenyl]-amide.

26. A pharmaceutical composition comprising a compound of formula I

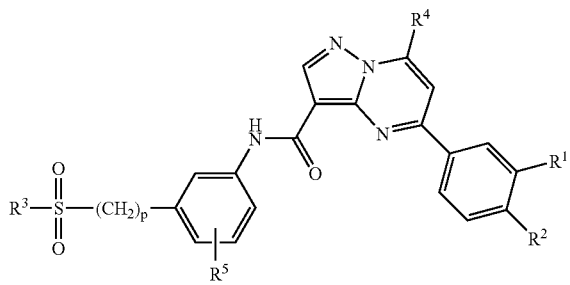

(I)

wherein p is 0 or 1;

$R^1$ and $R^2$ are each independently H; halogen; lower alkyl optionally substituted by lower alkoxy; lower alkoxy optionally substituted by one or more halogen; or $CF_3$;

$R^3$ is lower alkyl; hydroxy-lower alkyl; or $NR^aR^b$;

$R^a$ and $R^b$ are each independently selected from the group consisting of:
H;
lower alkyl optionally substituted by one or more hydroxy, fluoro, cycloalkyl, aryl, heteroaryl or $NR^cR^d$
wherein $R^c$ and $R^d$ are independently selected from H or lower alkyl;
cycloalkyl;
aryl; and
heteroaryl;
or $R^a$ and $R^b$ together with the nitrogen atom to which they are attached form an optionally substituted 5 or 6 membered heterocyclic ring;
$R^4$ is H, Cl, lower alkoxy, cycloalkyl or straight lower alkyl which is optionally substituted by one or more F; and $R^5$ is H; halogen or lower alkyl;
or a pharmaceutically acceptable salt thereof;
with the exception of the compounds:
pyrazolo[1,5-a]pyrimidine-3-carboxamide, 7-(difluoromethyl)-5-(4-methylphenyl)-N-[3-(4-morpholinylsulfonyl)phenyl];
pyrazolo[1,5-a]pyrimidine-3-carboxamide, 7-(difluoromethyl)-N-[3-(4-morphonlinylsulfonyl)phenyl]-5-phenyl; and
pyrazolo[1,5-a]pyrimidine-3-carboxamide, 7-(difluoromethyl)-5-(4-methoxyphenyl)-N-[3-(4-morpholinylsulphonyl)phenyl]
and a pharmaceutically acceptable carrier.

* * * * *